(12) United States Patent  
Simo et al.

(10) Patent No.: US 8,921,411 B2  
(45) Date of Patent: Dec. 30, 2014

(54) SOLID STATE FORMS OF CABAZITAXEL AND PROCESSES FOR PREPARATION THEREOF

(71) Applicant: Plus Chemicals SA, Paradiso (CH)

(72) Inventors: Ondrej Simo, Trnava (SK); Pavel Vraspir, Rymarov (CZ); Tomas Holas, Chlebicov (CZ); Alexandr Jegorov, Dobrá Voda (CZ); Roman Gabriel, Olomouc (CZ)

(73) Assignee: Plus Chemicals SA, Paradiso (CH)

( * ) Notice: Subject to any disclaimer, the term of this patent is extended or adjusted under 35 U.S.C. 154(b) by 0 days.

(21) Appl. No.: 13/932,147

(22) Filed: Jul. 1, 2013

(65) Prior Publication Data

US 2014/0011865 A1     Jan. 9, 2014

Related U.S. Application Data

(63) Continuation of application No. PCT/US2012/033061, filed on Apr. 11, 2012.

(60) Provisional application No. 61/474,572, filed on Apr. 12, 2011, provisional application No. 61/517,954, filed on Apr. 27, 2011, provisional application No. 61/486,894, filed on May 17, 2011, provisional application No. 61/598,473, filed on Feb. 14, 2012, provisional application No. 61/607,875, filed on Mar. 7, 2012.

(51) Int. Cl.  
*C07D 305/14*     (2006.01)

(52) U.S. Cl.  
CPC .................. *C07D 305/14* (2013.01)  
USPC .......................................... 514/449; 549/510

(58) Field of Classification Search  
CPC ........................ A61K 31/337; C07D 305/14  
USPC .......................................... 514/449; 549/510  
See application file for complete search history.

(56) References Cited

U.S. PATENT DOCUMENTS 5,847,170 A * 12/1998 Bouchard et al. ............. 549/510  
5,889,043 A     3/1999 Bouchard et al.  
6,040,466 A     3/2000 Bouchard et al.

(Continued)

FOREIGN PATENT DOCUMENTS

CN     102503913 A     6/2012  
CN     102659722 A     9/2012

(Continued)

OTHER PUBLICATIONS

International Search Report and Written Opinion of the International Searching Authority for International Application No. PCT/US2012/033061, mailed on Jul. 27, 2012.

(Continued)

*Primary Examiner* — Savitha Rao  
*Assistant Examiner* — Angela Brown-Pettigrew  
(74) *Attorney, Agent, or Firm* — Baker & Hostetler LLP

(57) ABSTRACT

The invention relates to solid state forms of Cabazitaxel, and processes for preparation, via novel synthetic intermediates, thereof, and formulations comprising one or more of the solid state forms of Cabazitaxel. The present invention further provides pharmaceutical compositions comprising one or more of the solid state forms of Cabazitaxel, and a method of treating hormone-refractory prostate cancer.

26 Claims, 37 Drawing Sheets shows a powder X-ray diffraction pattern ("Powder XRD") for crystalline Cabazitaxel form I. The peak marked "Si" corresponds to the silicon internal standard.

(56) References Cited

U.S. PATENT DOCUMENTS

| | | | |
|---|---|---|---|
| 6,232,477 B1 | 5/2001 | Bouchard et al. | |
| 6,331,635 B1 | 12/2001 | Bouchard et al. | |
| 6,372,780 B2 | 4/2002 | Bouchard et al. | |
| 6,387,946 B1 | 5/2002 | Bouchard et al. | |
| 6,593,482 B2 | 7/2003 | Bouchard et al. | |
| 7,241,907 B2 | 7/2007 | Didier et al. | |
| 2005/0065138 A1 | 3/2005 | Didier et al. | |
| 2011/0144362 A1* | 6/2011 | Billot et al. | 549/541 |

FOREIGN PATENT DOCUMENTS

| | | | |
|---|---|---|---|
| CN | 102675257 A | 9/2012 | |
| CN | 102746258 A | 10/2012 | |
| CN | 102887877 A | 1/2013 | |
| CN | 102898406 A | 1/2013 | |
| EP | 817779 | 3/1996 | |
| EP | 817780 | 3/1996 | |
| EP | 1667986 A1 | 6/2006 | |
| EP | 2247582 A1 | 11/2010 | |
| WO | 96/30355 | 10/1996 | |
| WO | 96/30356 | 10/1996 | |
| WO | 2005/028462 A1 | 3/2005 | |
| WO | 2009/115655 A2 | 9/2009 | |
| WO | 2013/034979 A2 | 3/2013 | |

OTHER PUBLICATIONS

Dr. Deepali, Third party observations, 24 Pages, published on—Feb. 13, 2013 & Oct. 16, 2013 Publisher—European patent office; Place of publication: European patent register online.

Dr. Deepali, Third party observations, 24 Pages, published on Feb. 13, 2013 & Oct. 16, 2013 Publisher—European patent office; Place of publication: European patent register online.

Sanofi, "Reply to communication from the Examining Division", 3 pages, Apr. 6, 2012, EPO-Munich and is available online through the following link, https://register.epo.org/application?documentId=ETAOX3683875754&number=EP04787385&lng=en&npl=false.

* cited by examiner

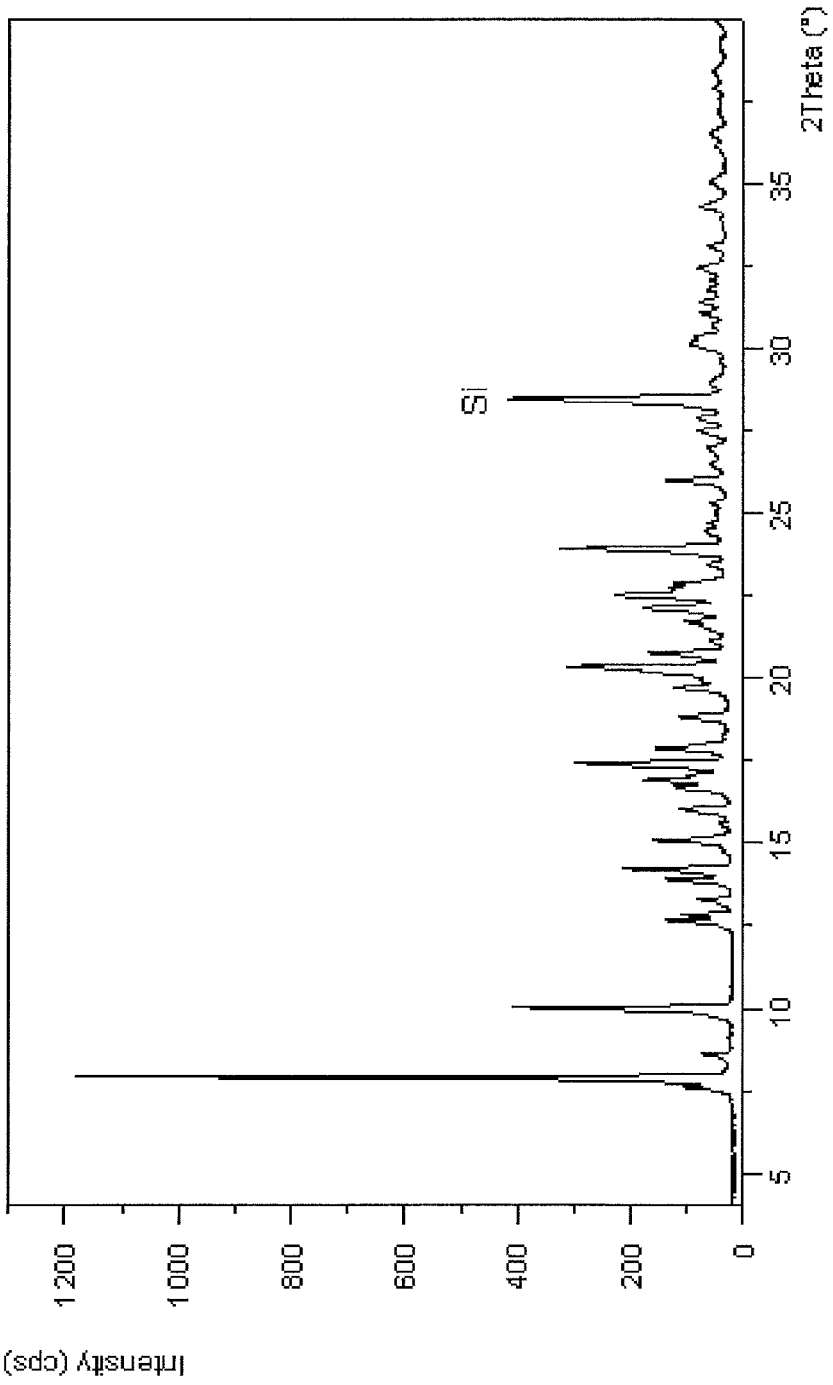

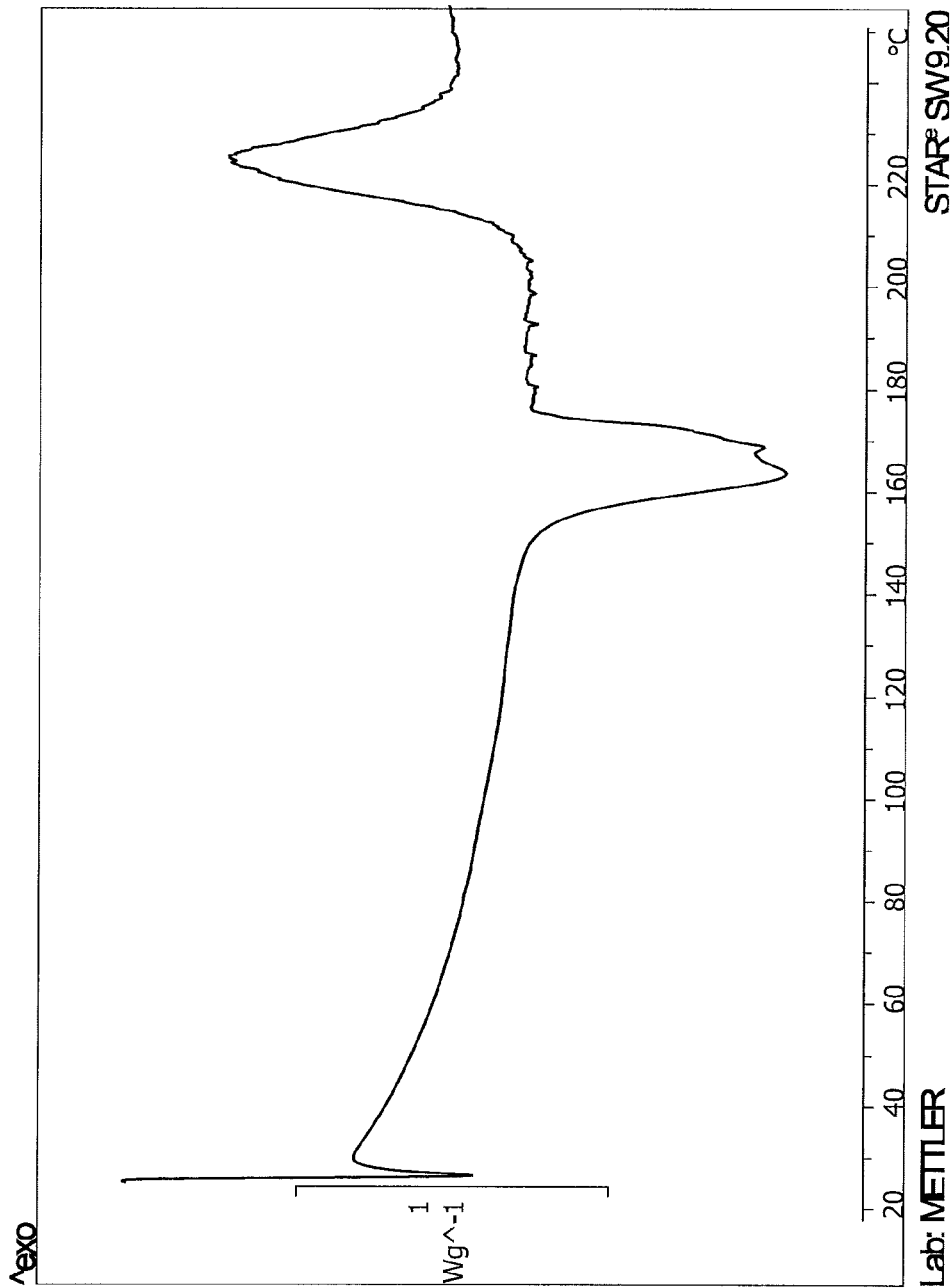
Figure 2 shows a Differential Scanning Calorimetry ("DSC") thermogram for crystalline Cabazitaxel form I.

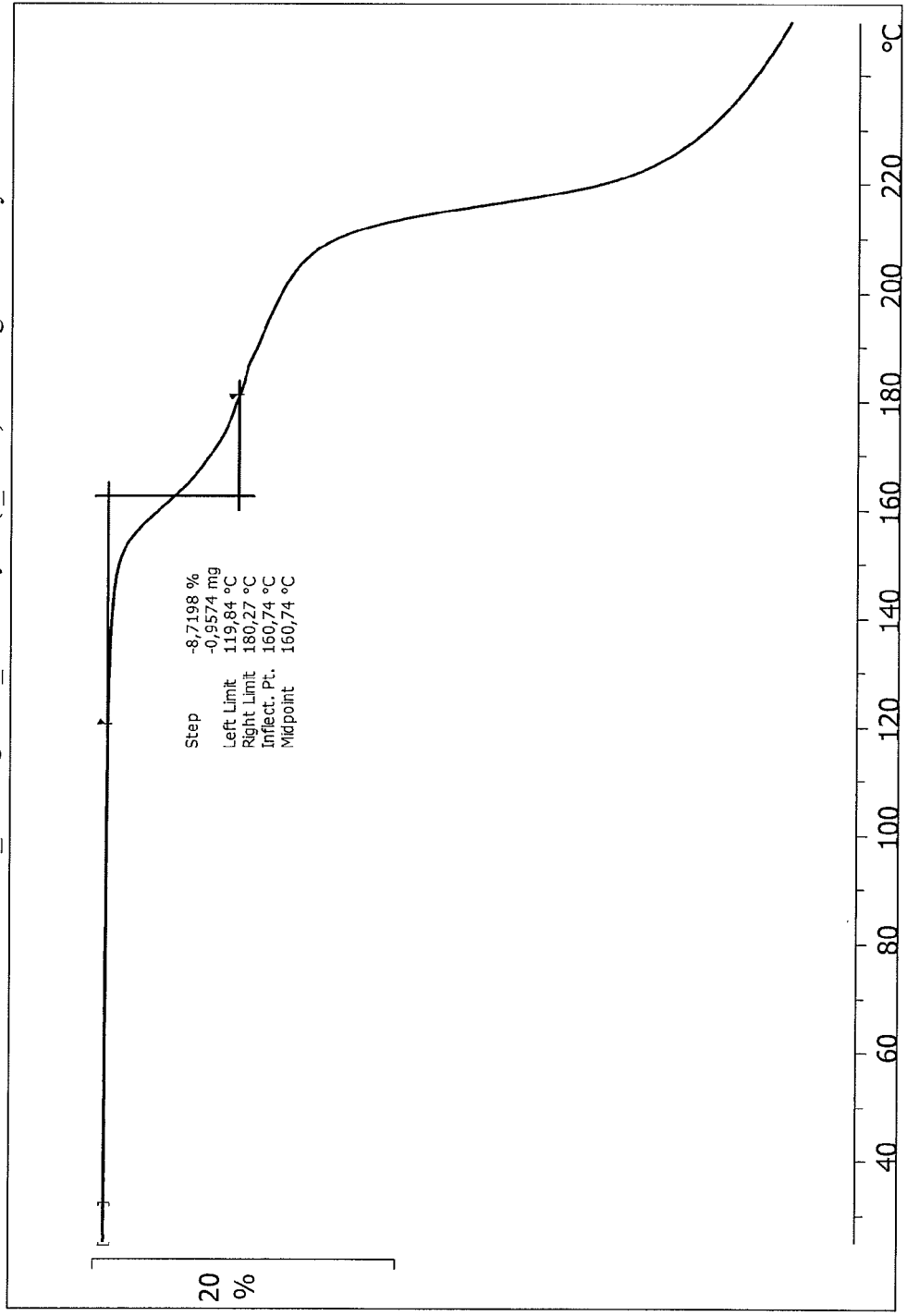
Figure 3 shows a Thermogravimetric analysis ("TGA") thermogram for crystalline Cabazitaxel form I.

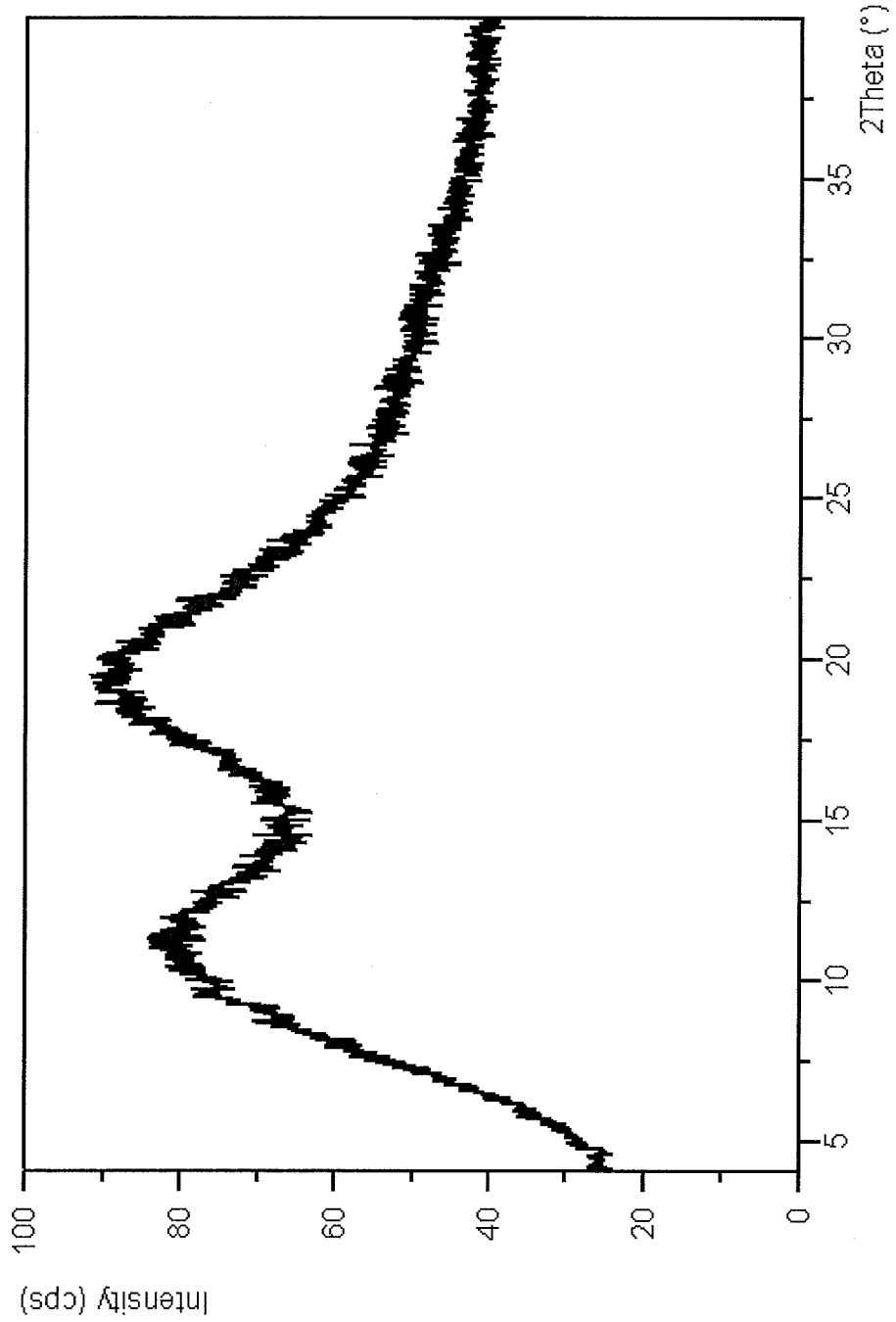

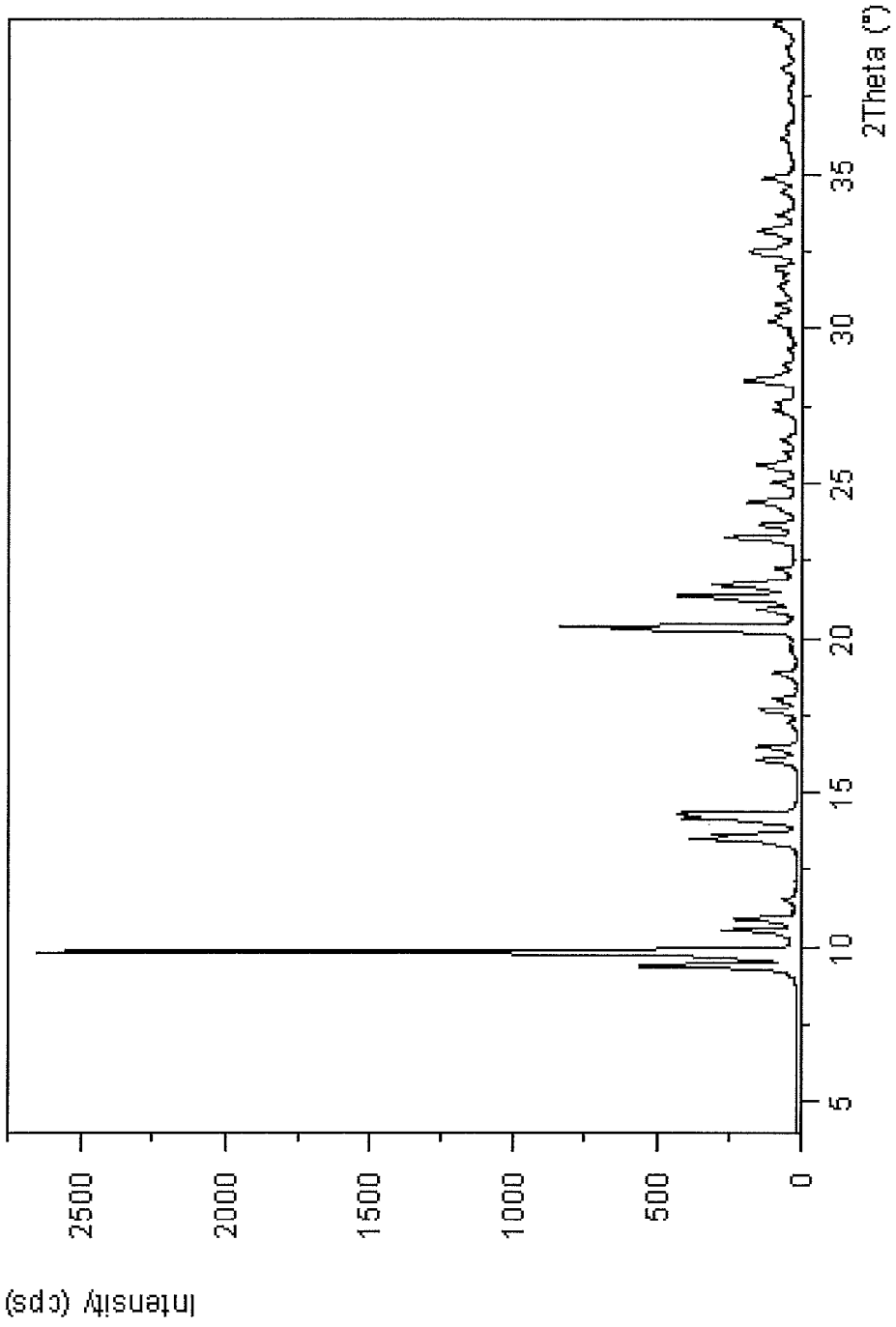

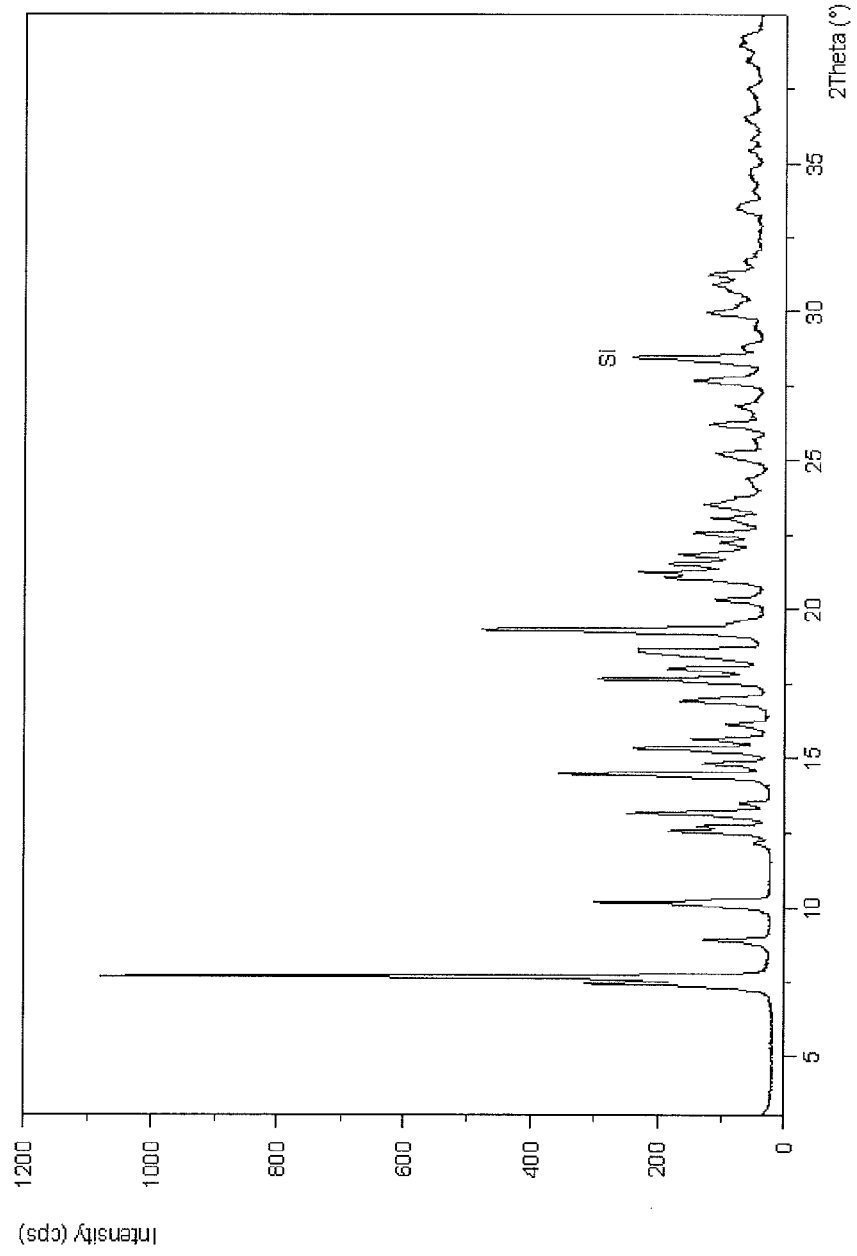
Figure 6 shows a powder X-ray diffraction pattern for crystalline Cabazitaxel form II. The peak marked "Si" corresponds to the silicon internal standard.

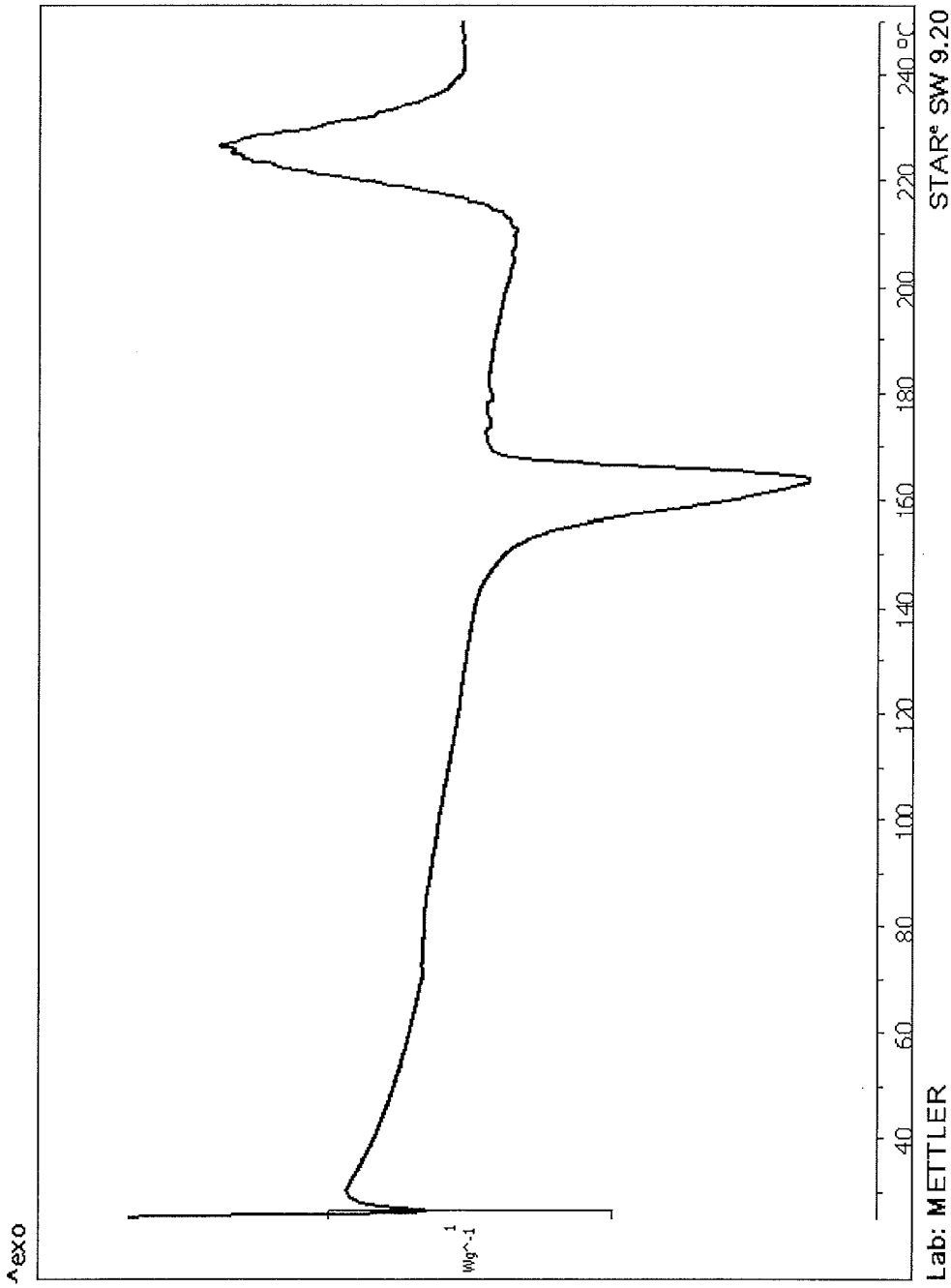

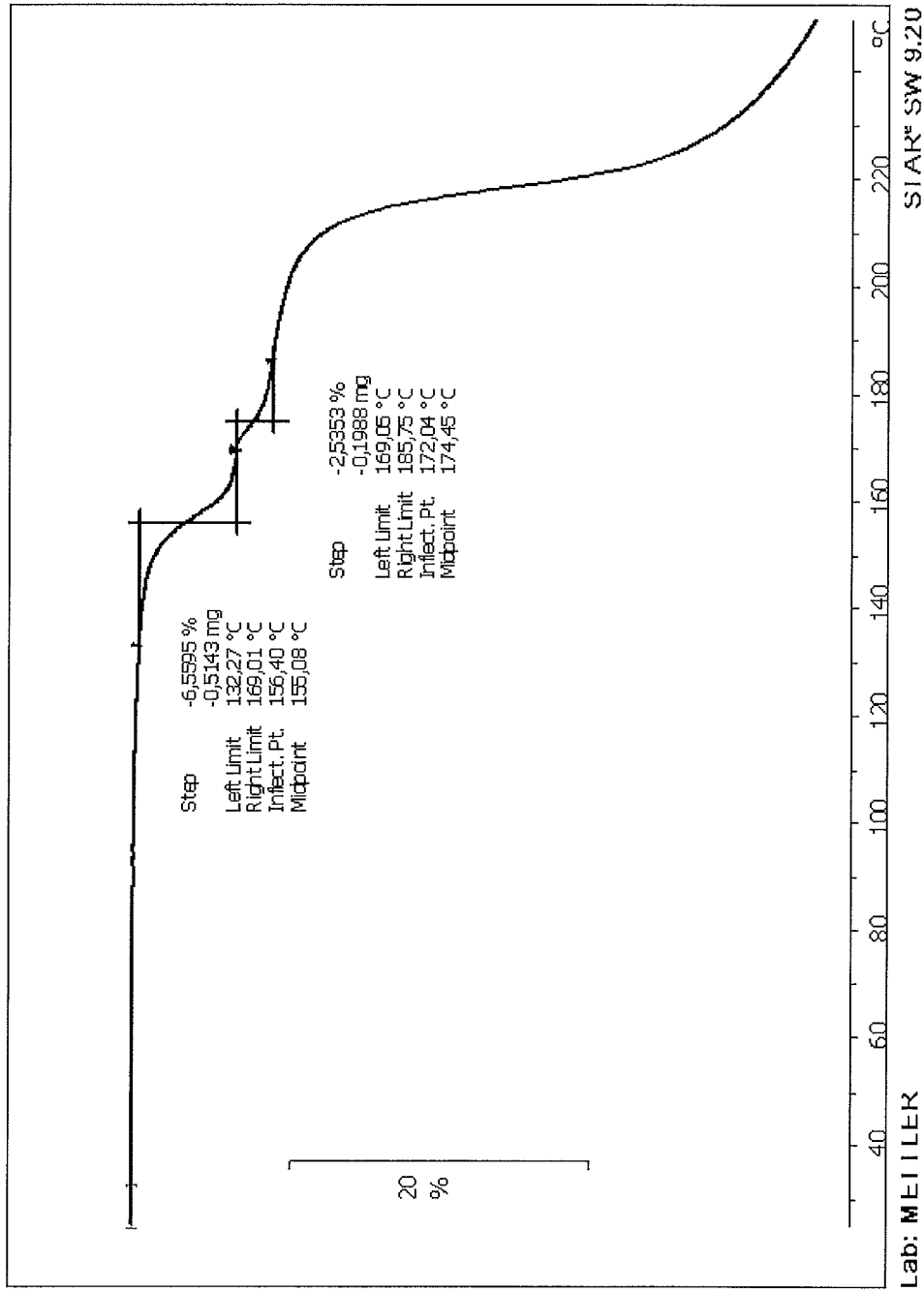
Figure 8 shows a Thermogravimetric analysis ("TGA") thermogram for crystalline Cabazitaxel form II.

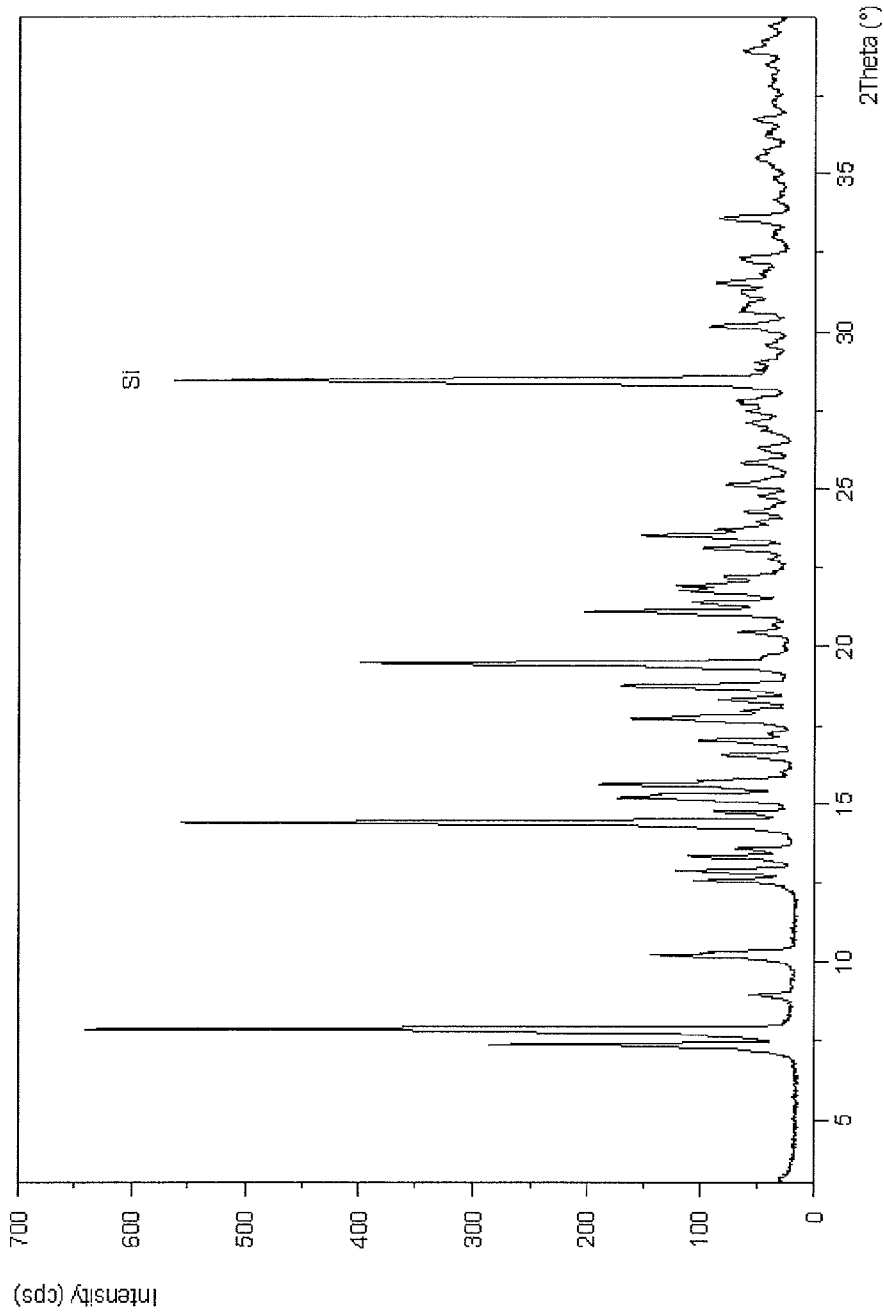
Figure 9 shows a powder X-ray diffraction pattern for crystalline Cabazitaxel form III. The peak marked "Si" corresponds to the silicon internal standard.

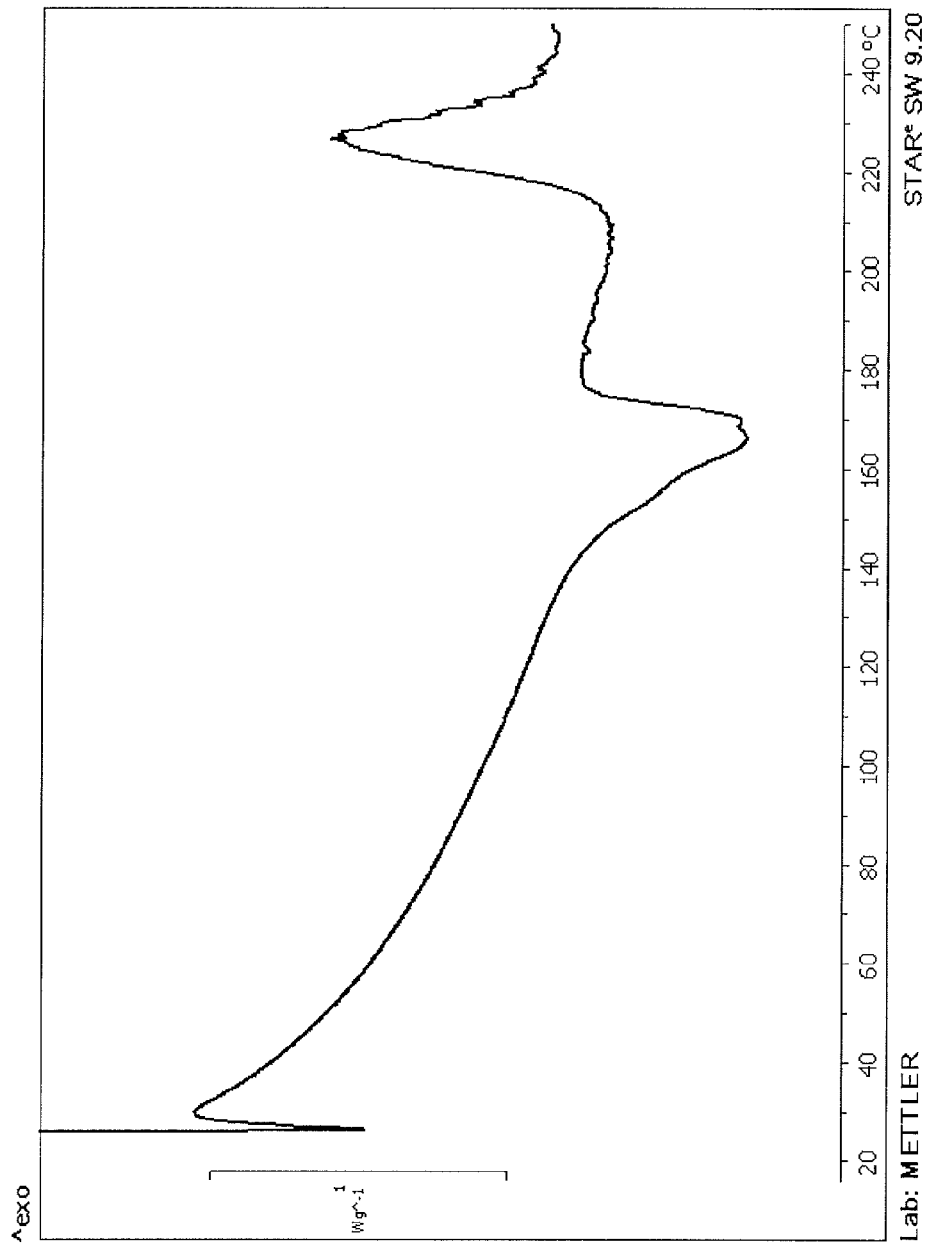
Figure 10 shows a Differential Scanning Calorimetry ("DSC") thermogram for crystalline Cabazitaxel form III.

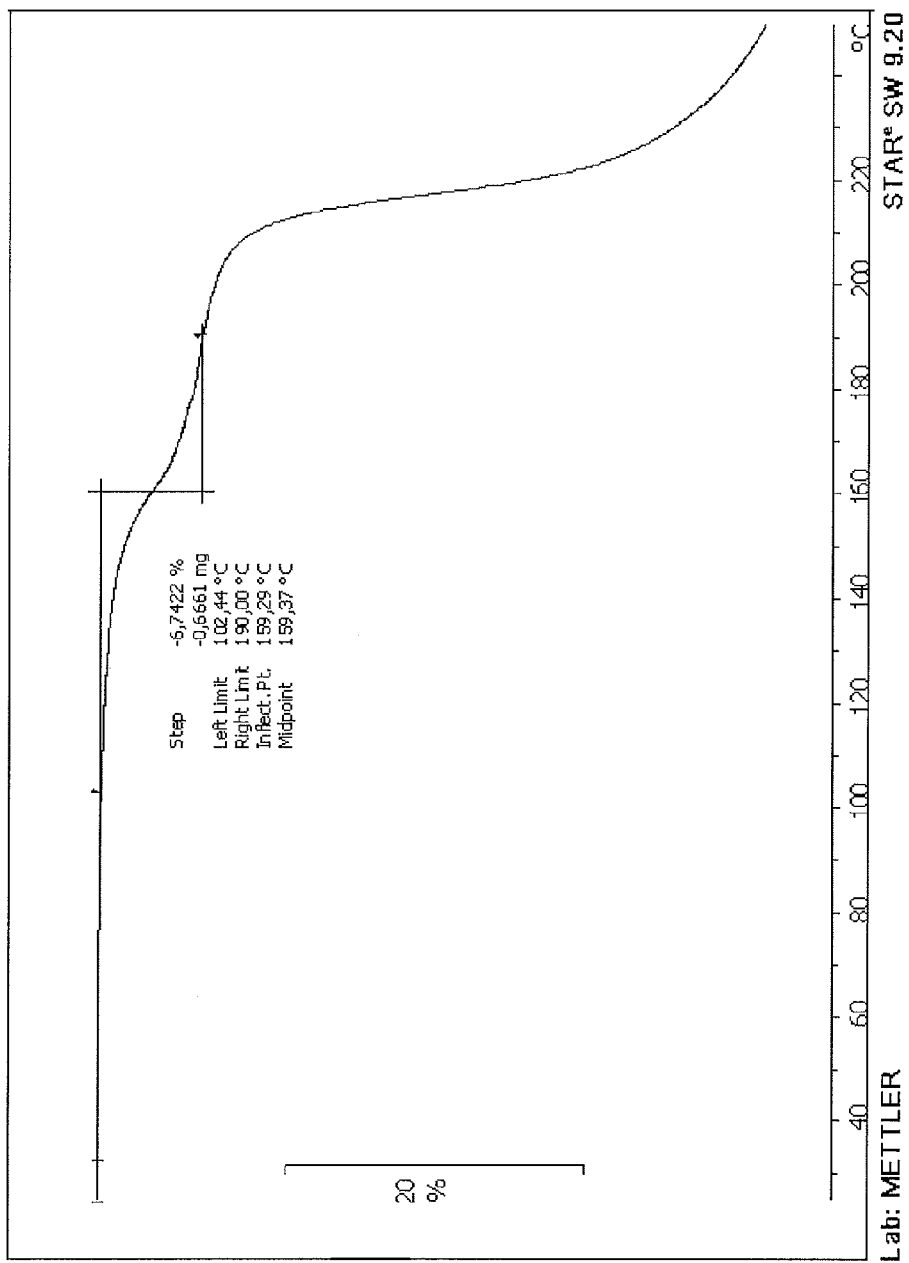
Figure 11 shows a Thermogravimetric analysis ("TGA") thermogram for crystalline Cabazitaxel form III.

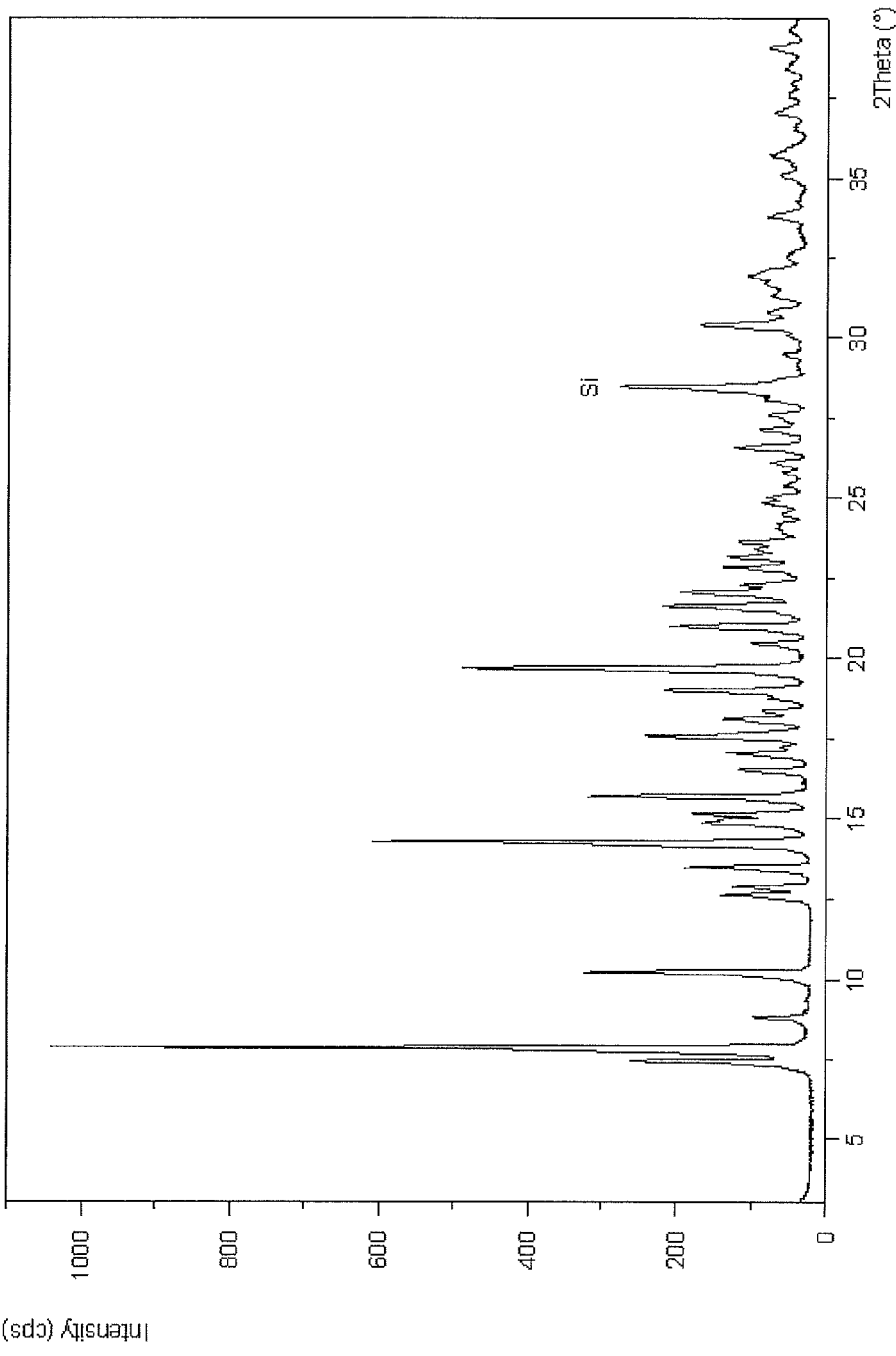
Figure 12 shows a powder X-ray diffraction pattern for crystalline Cabazitaxel form IV. The peak marked "Si" corresponds to the silicon internal standard.

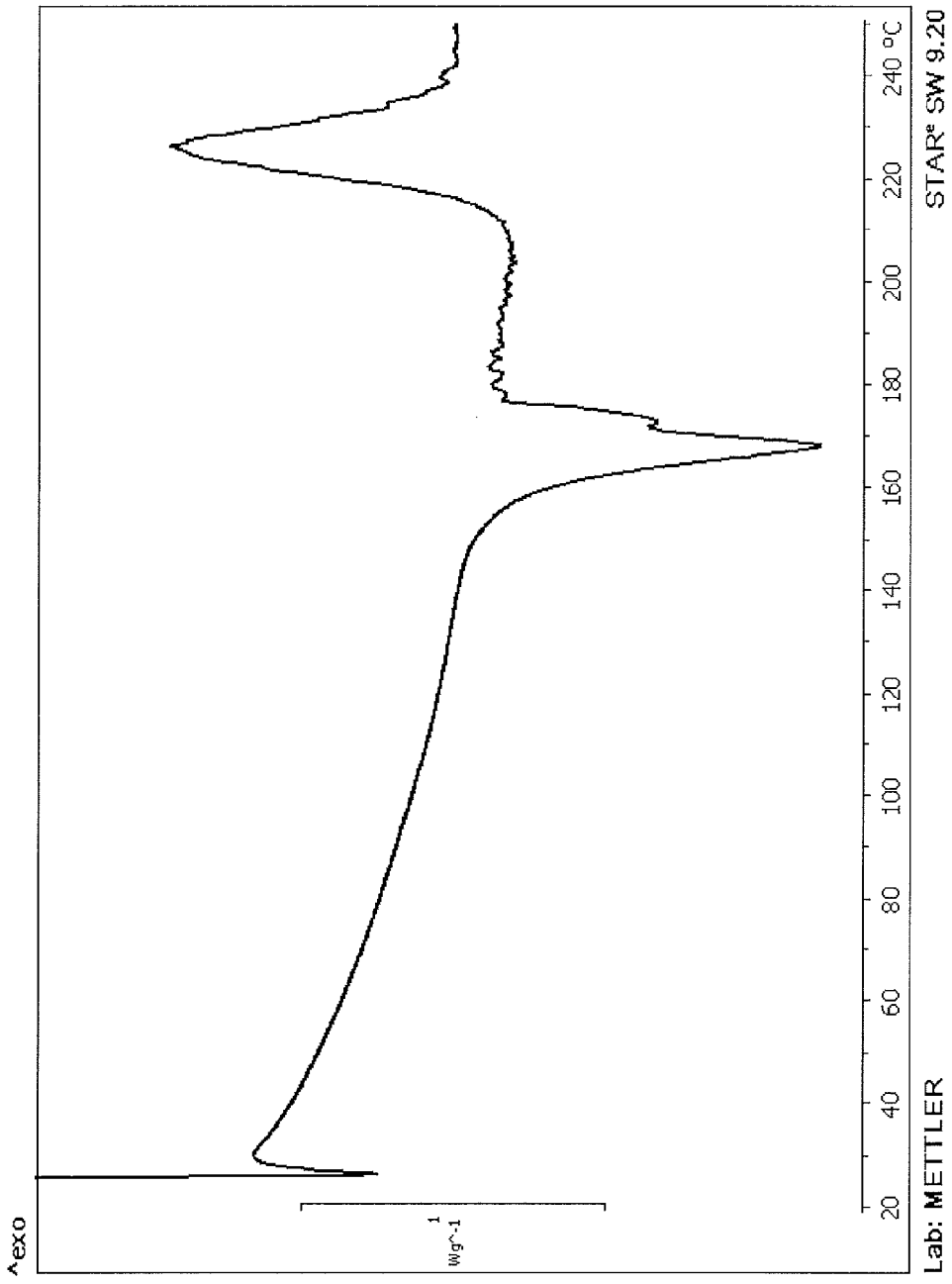
Figure 13 shows a Differential Scanning Calorimetry ("DSC") thermogram for crystalline Cabazitaxel form IV.

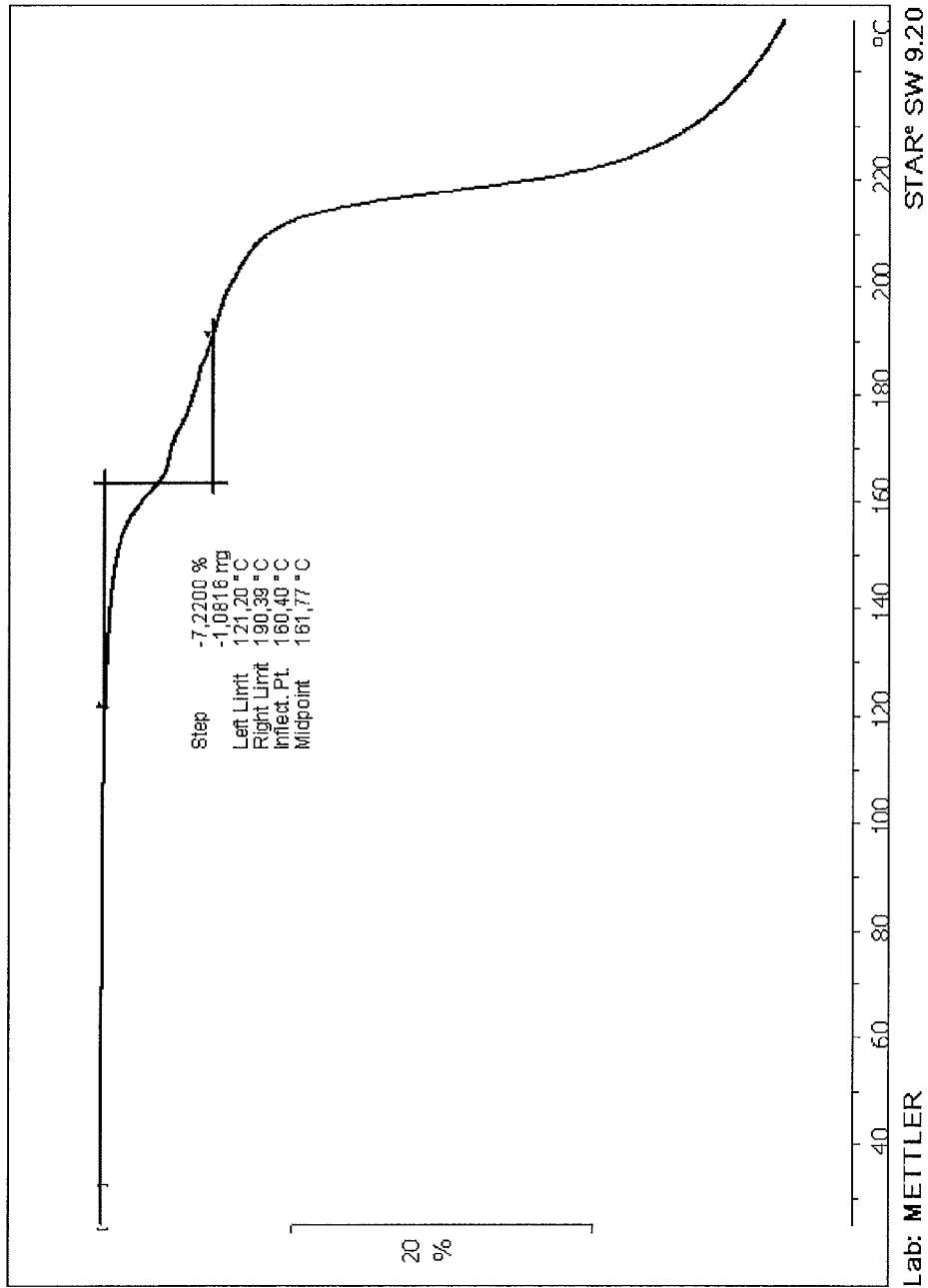
Figure 14 shows a Thermogravimetric analysis ("TGA") thermogram for crystalline Cabazitaxel form IV.

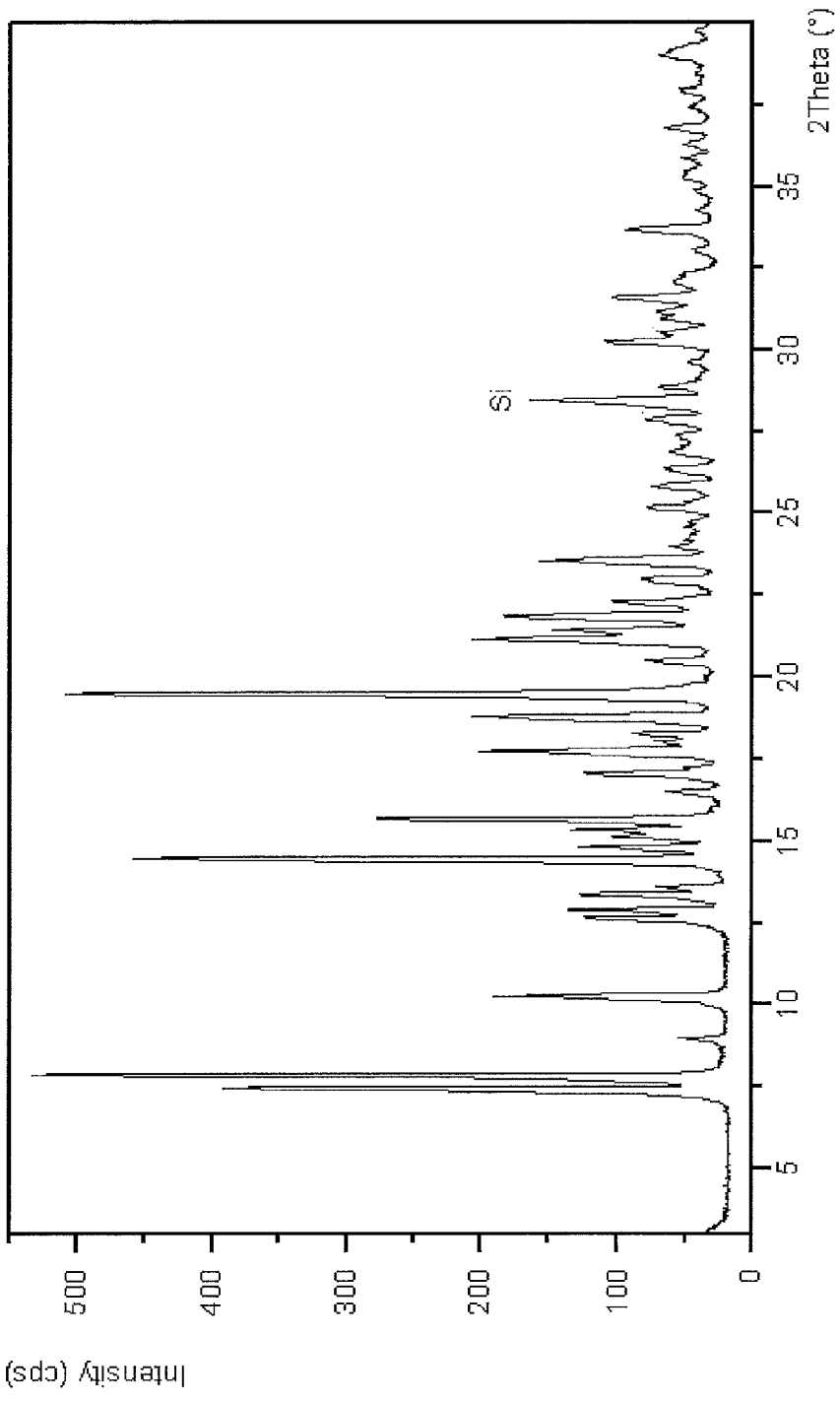
Figure 15 shows a powder X-ray diffraction pattern for crystalline Cabazitaxel form V. The peak marked "Si" corresponds to the silicon internal standard.

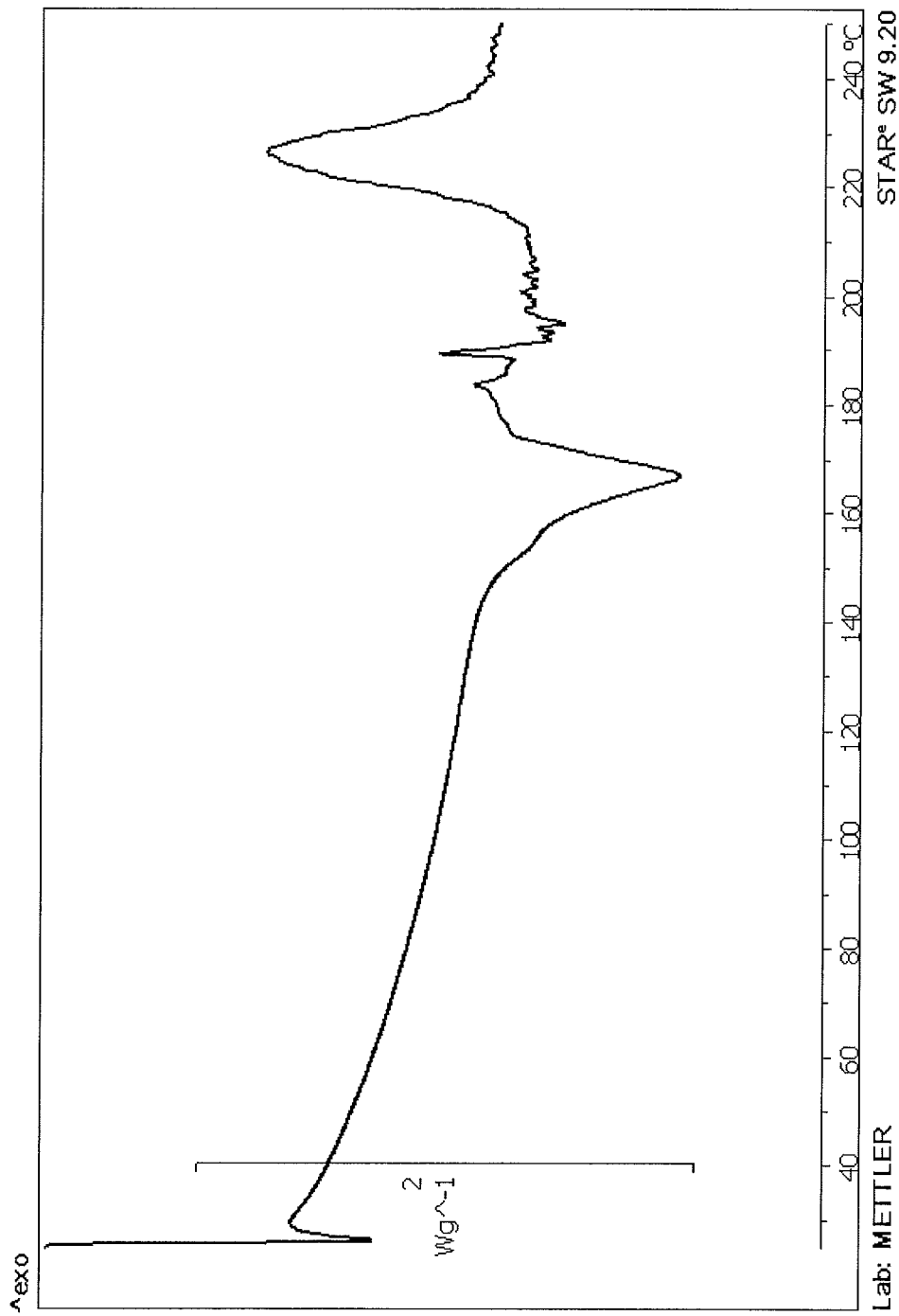

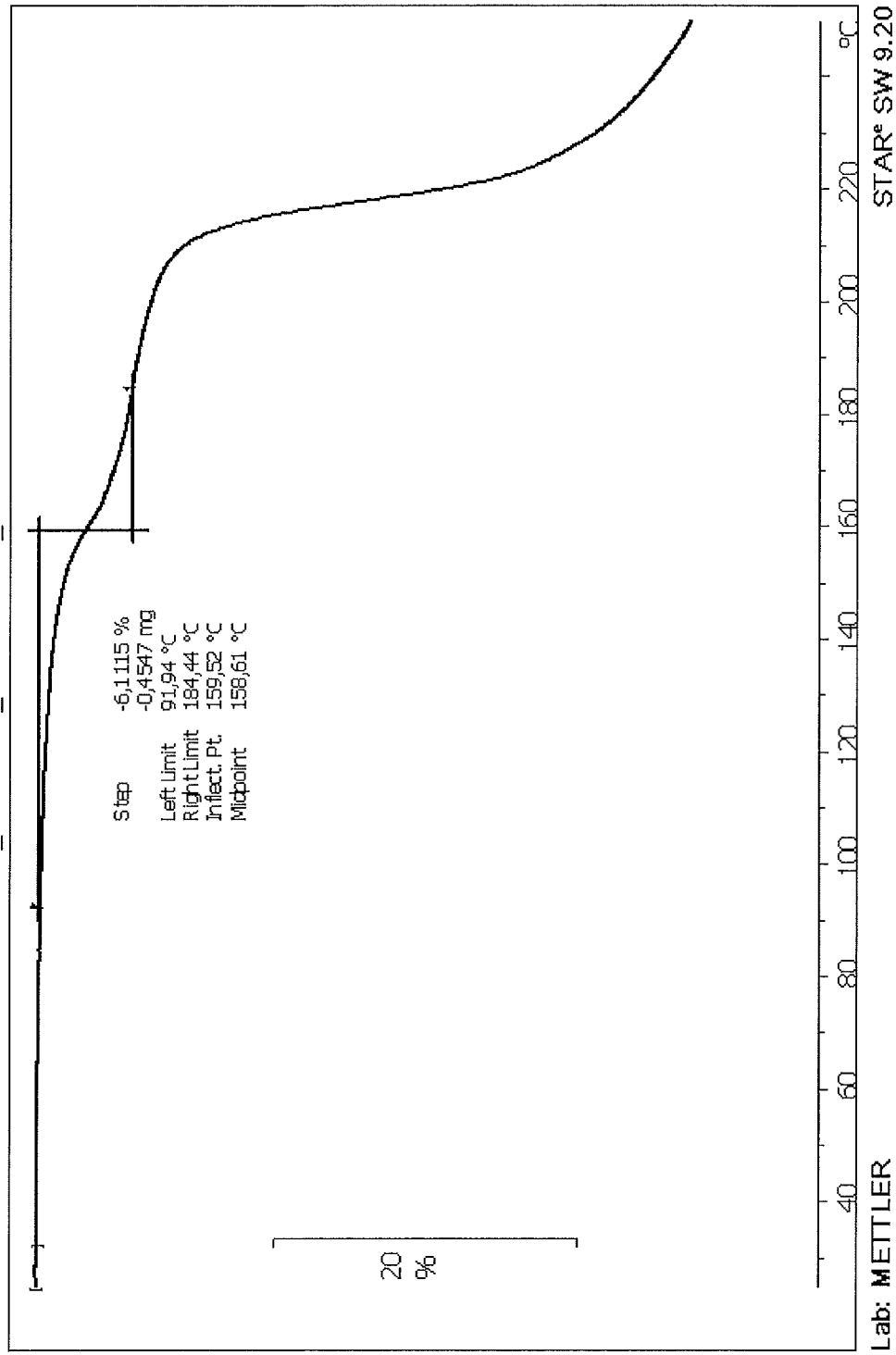
Figure 17 shows a Thermogravimetric analysis ("TGA") thermogram for crystalline Cabazitaxel form V.

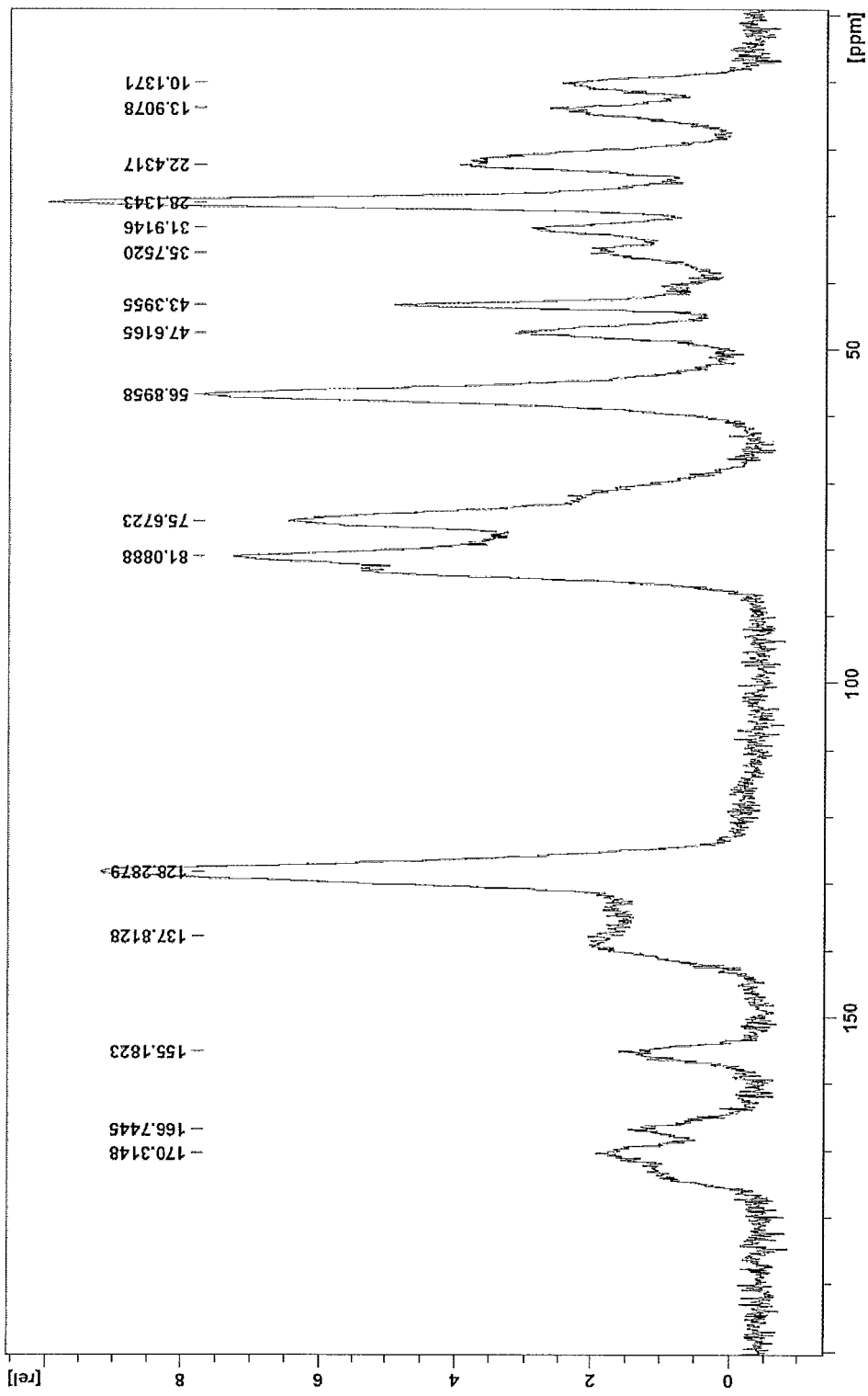
Figure 18 shows a full-width solid state 13C NMR spectrum for amorphous Cabazitaxel.

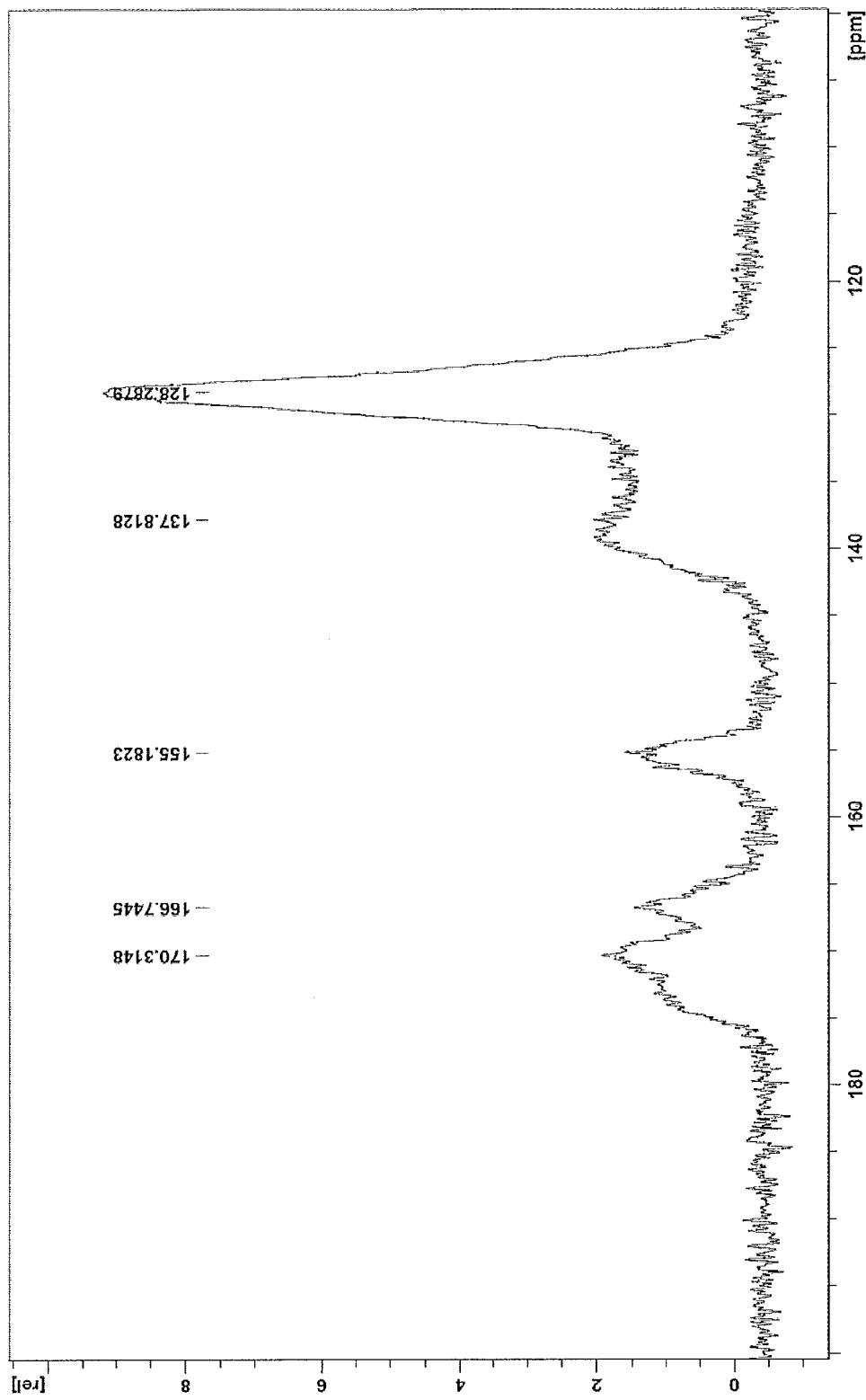
Figure 19 shows a detailed solid state 13C NMR spectrum for amorphous Cabazitaxel in range 200 – 100 ppm

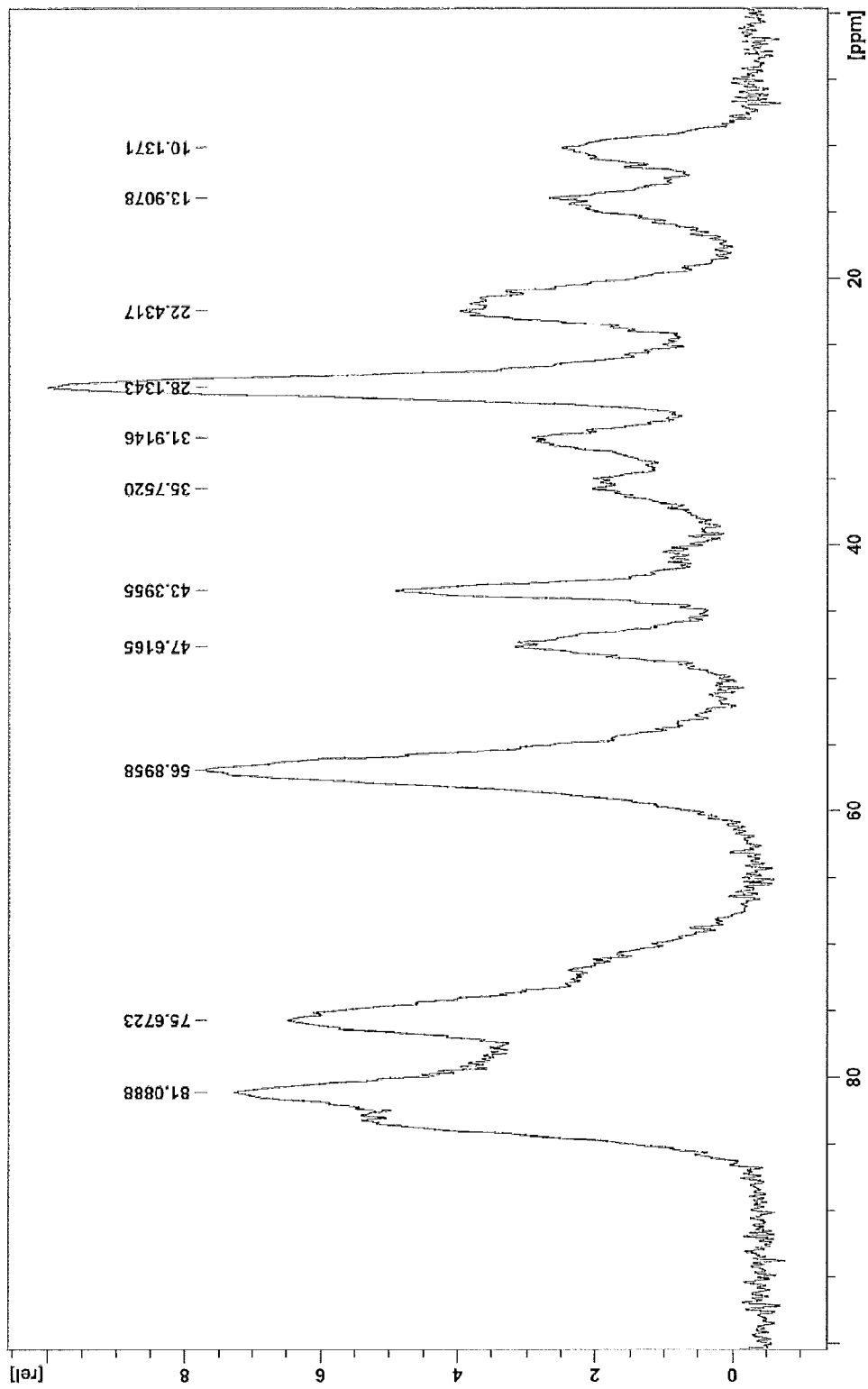
Figure 20 shows a detailed solid state $^{13}$C NMR spectrum for amorphous Cabazitaxel in range 100 – 0 ppm.

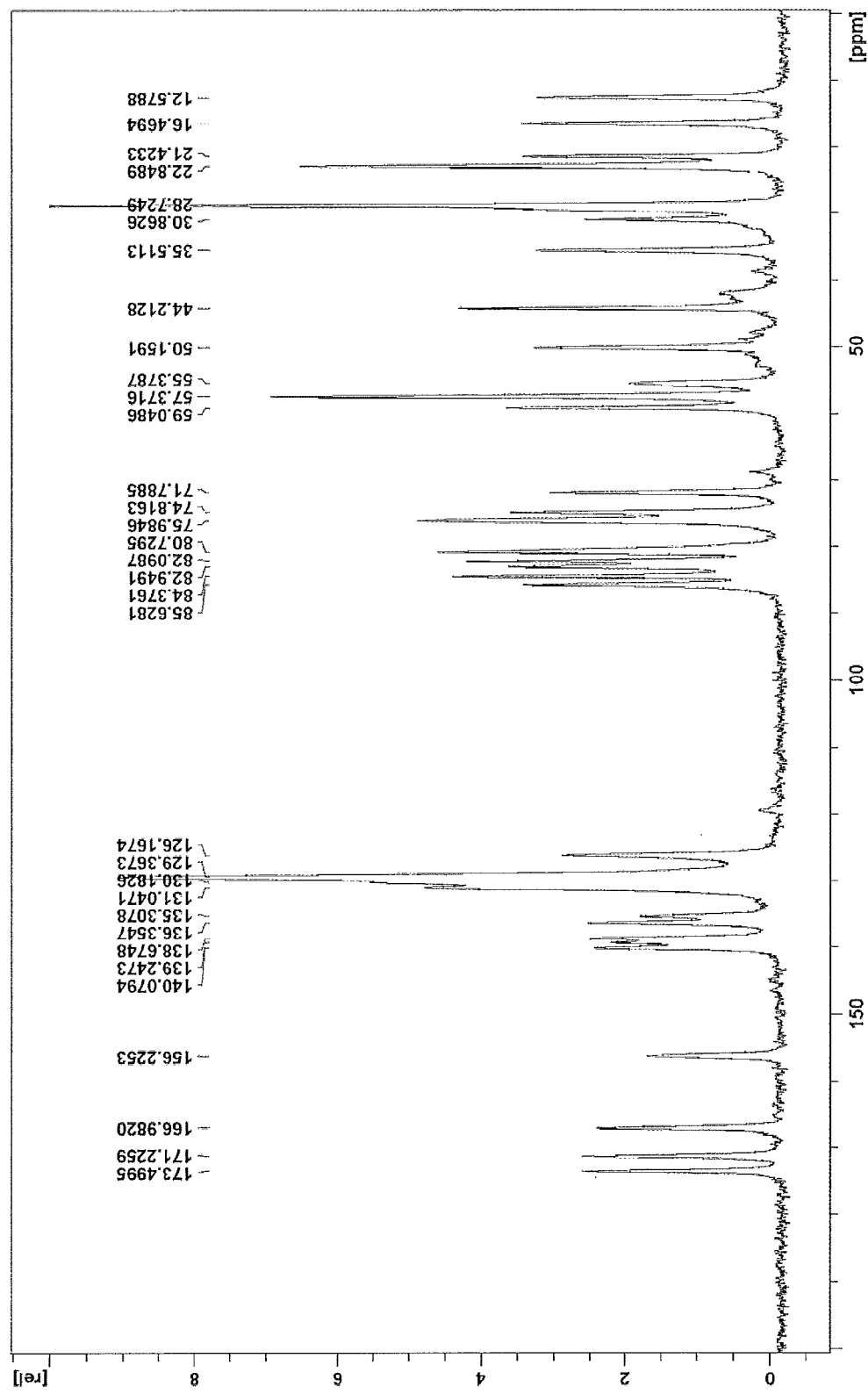
Figure 21 shows a full-width solid state $^{13}$C NMR spectrum for crystalline Cabazitaxel form I.

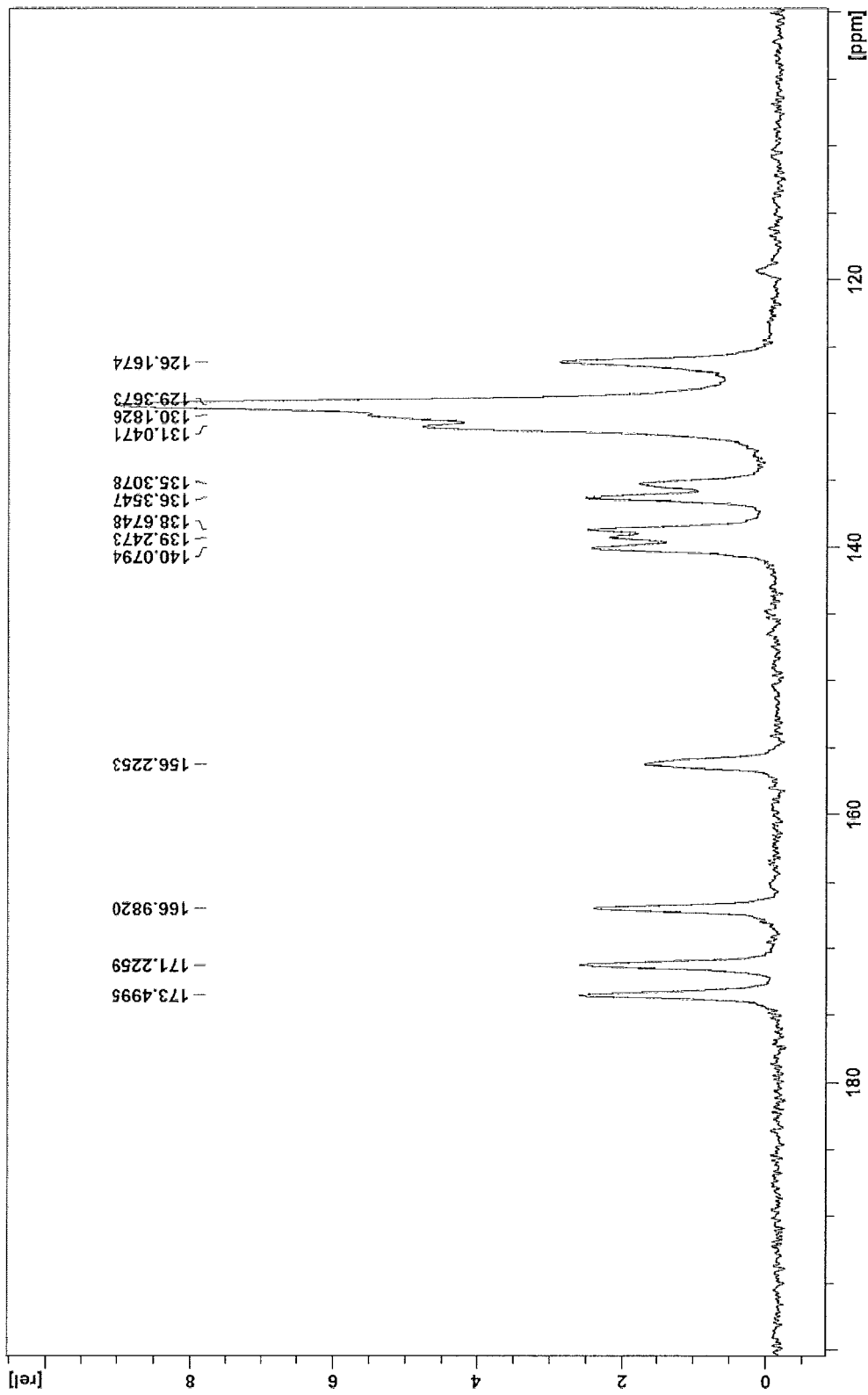
Figure 22 shows a detailed solid state $^{13}$C NMR spectrum for crystalline Cabazitaxel form I in range 200 – 100 ppm.

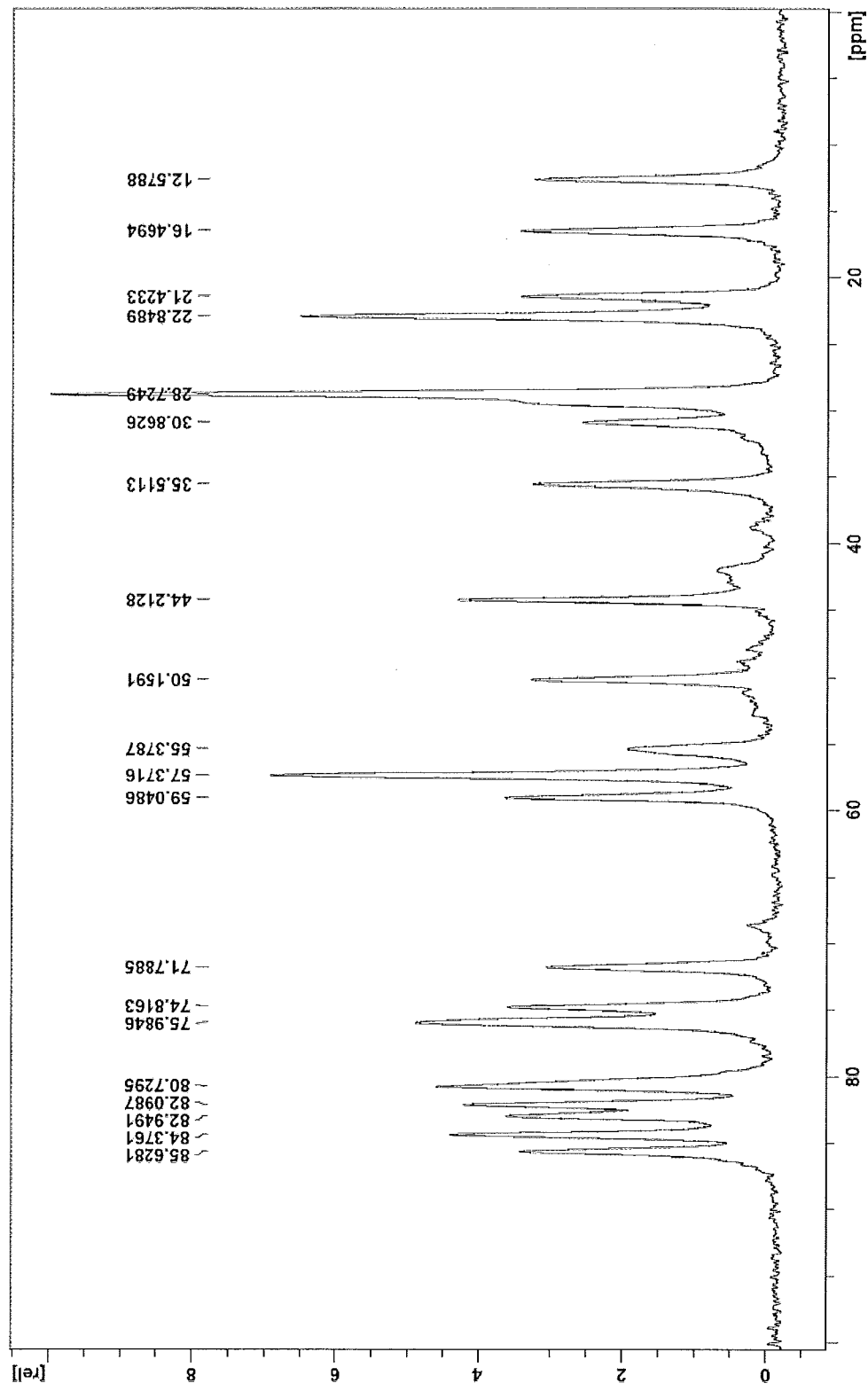
Figure 23 shows a detailed solid state $^{13}$C NMR spectrum for crystalline Cabazitaxel form I in range 100 – 0 ppm.

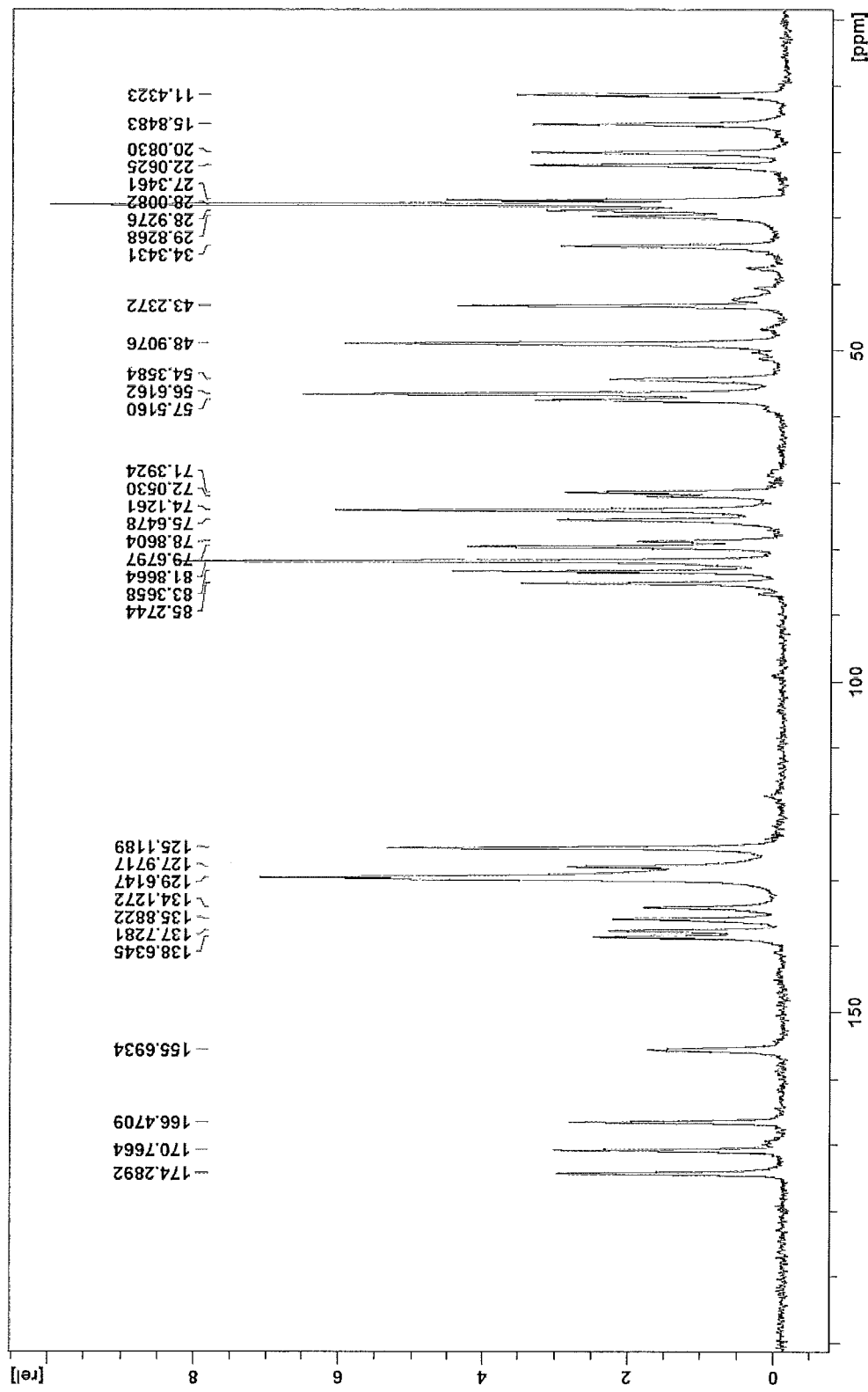
Figure 24 shows a full-width solid state $^{13}$C NMR spectrum for crystalline Cabazitaxel form II.

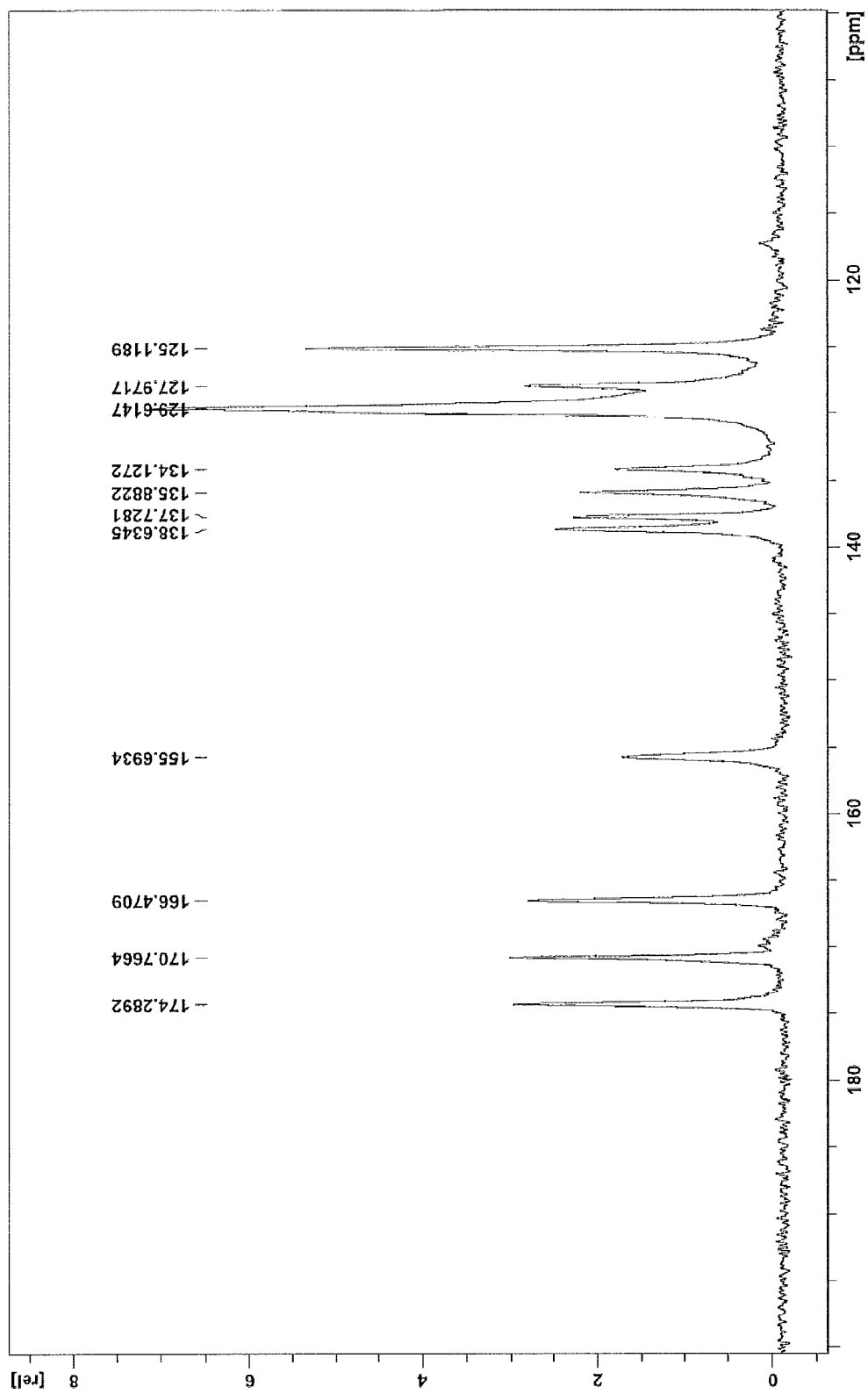
Figure 25 shows a detailed solid state ¹³C NMR spectrum for crystalline Cabazitaxel form II in range 200 – 100 ppm.

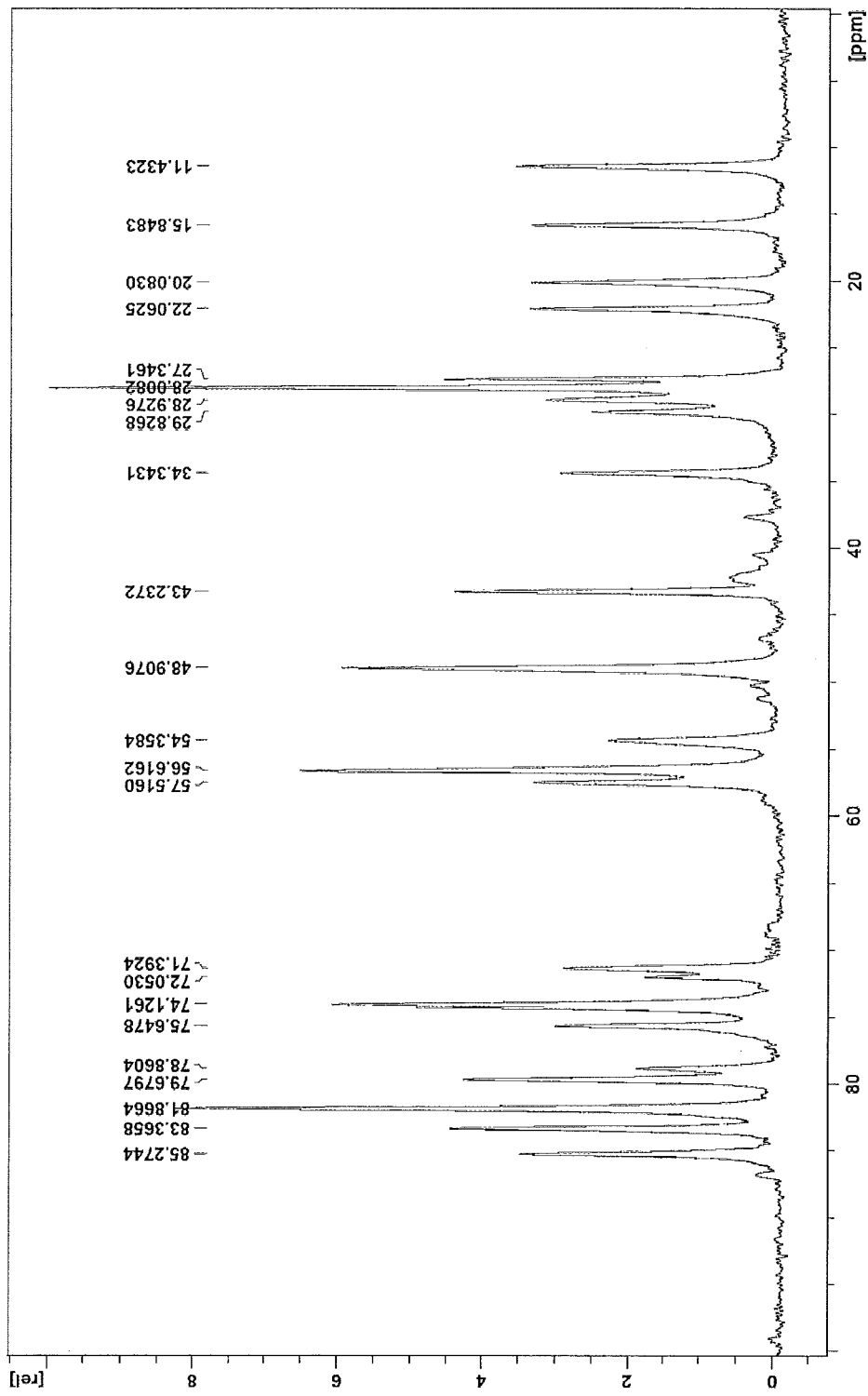
Figure 26 shows a detailed solid state $^{13}$C NMR spectrum for crystalline Cabazitaxel form II in range 100 – 0 ppm.

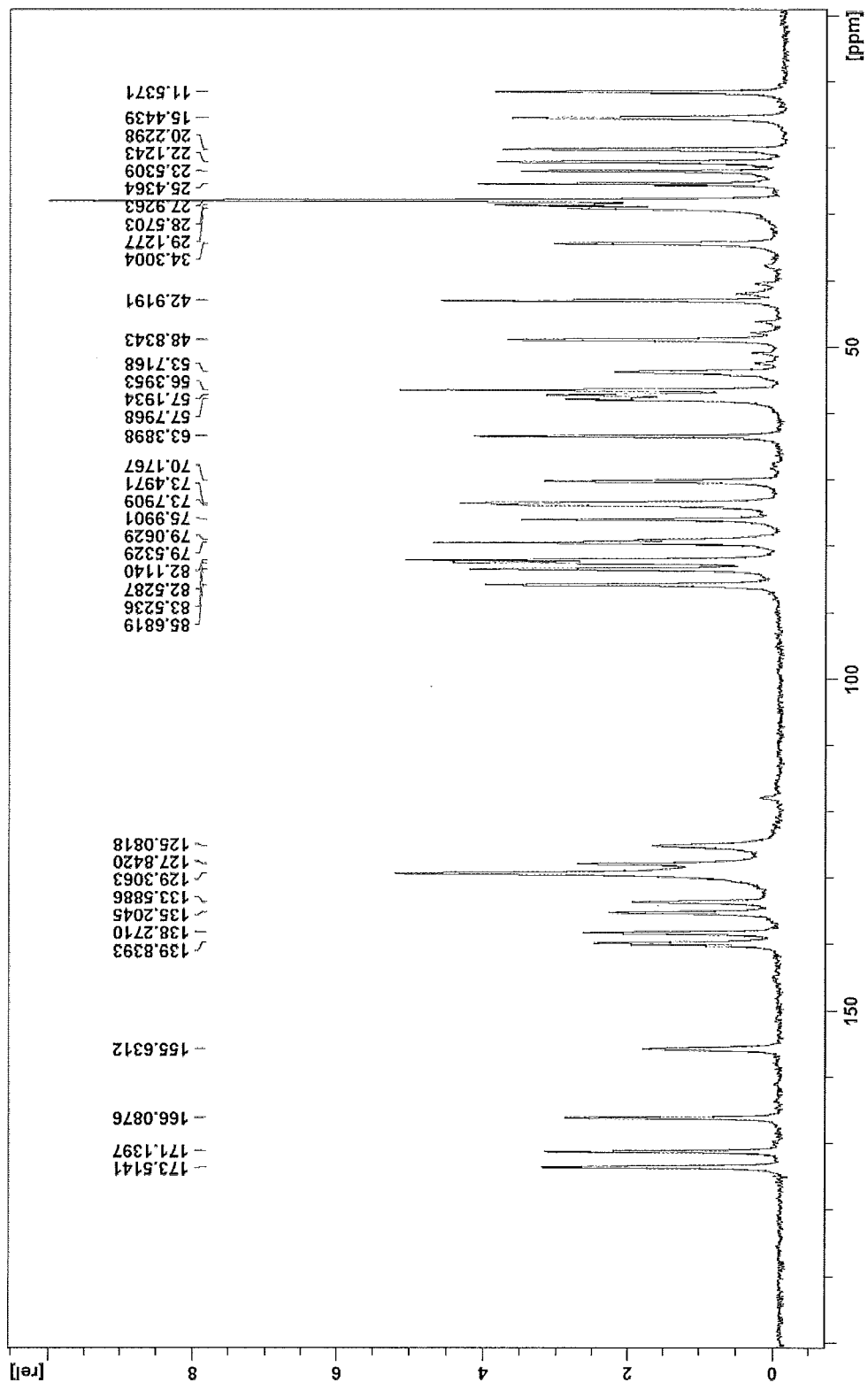
Figure 27 shows a full-width solid state $^{13}$C NMR spectrum for crystalline Cabazitaxel form III.

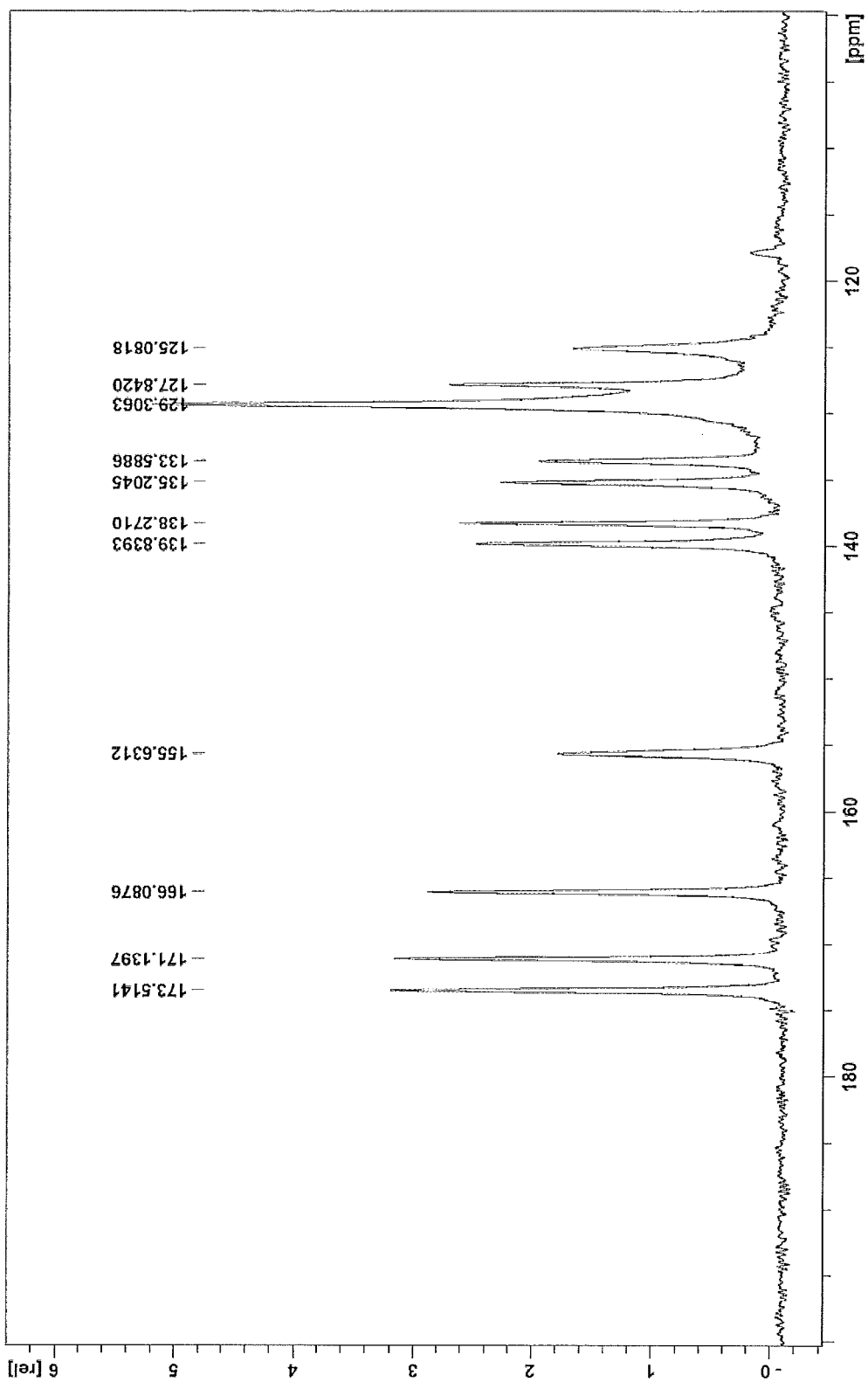
Figure 28 shows a detailed solid state $^{13}$C NMR spectrum for crystalline Cabazitaxel form III in range 200 – 100 ppm.

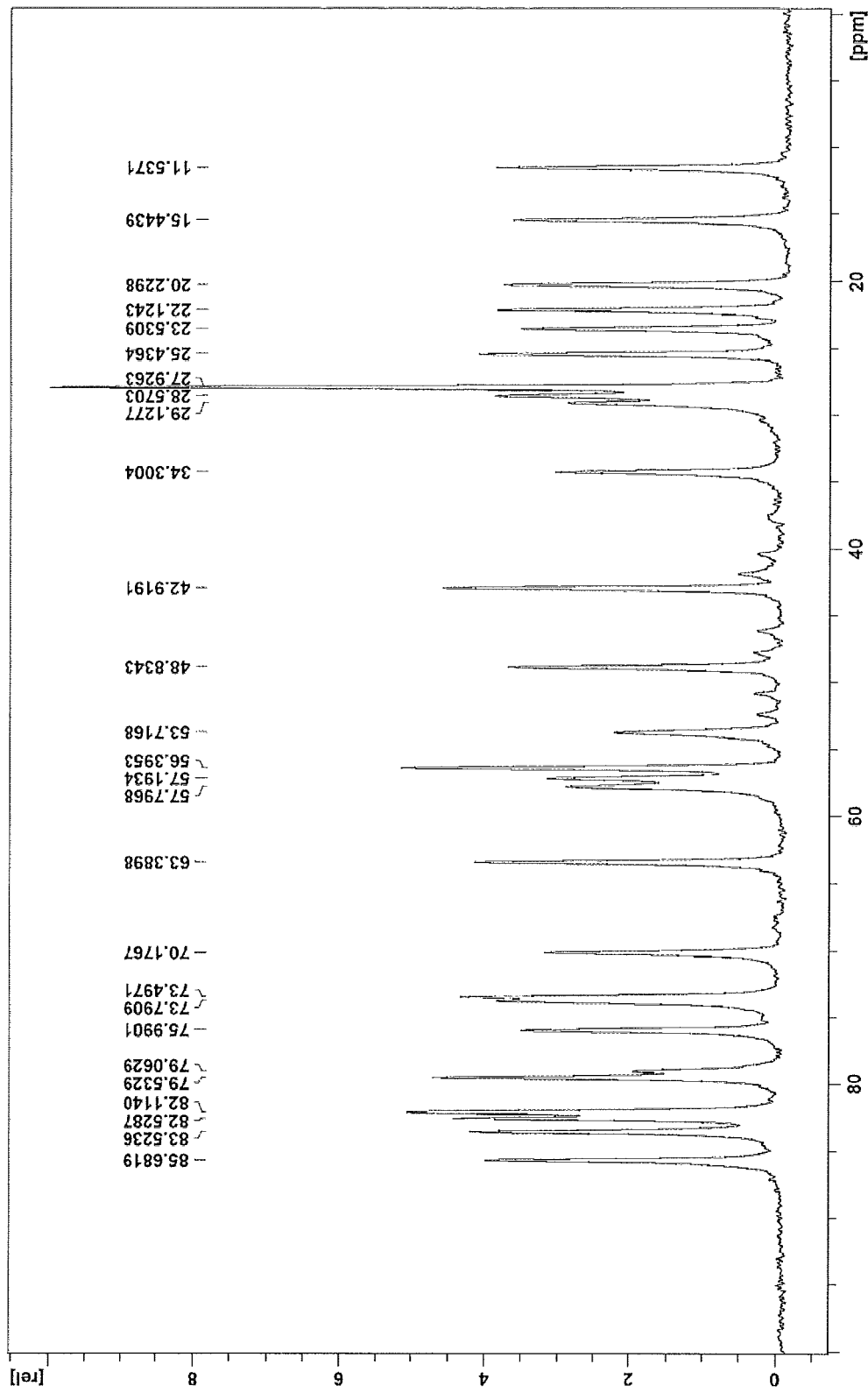
Figure 29 shows a detailed solid state $^{13}$C NMR spectrum for crystalline Cabazitaxel form III in range 100 – 0 ppm.

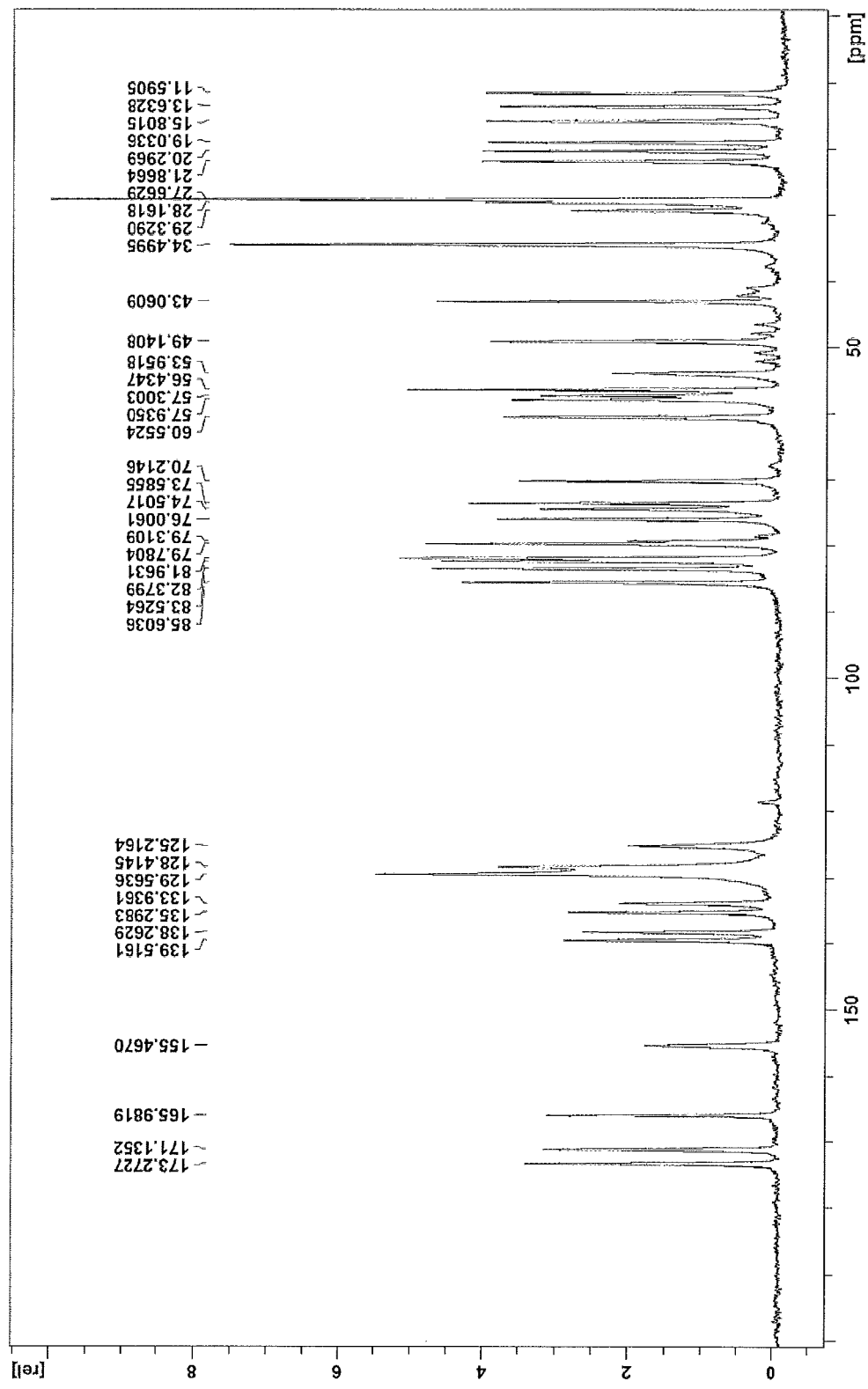
Figure 30 shows a full-width solid state $^{13}$C NMR spectrum for crystalline Cabazitaxel form IV.

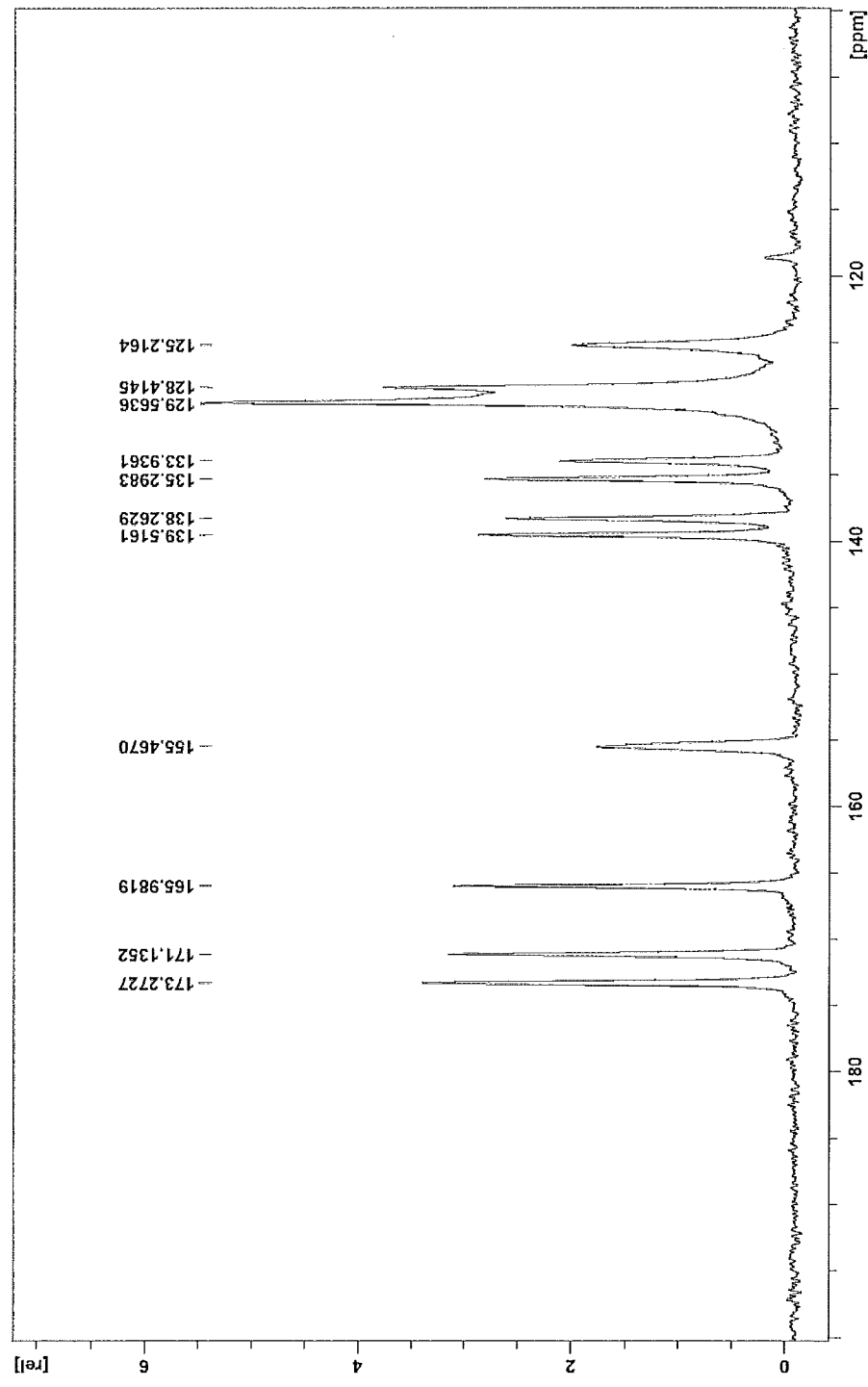
Figure 31 shows a detailed solid state $^{13}$C NMR spectrum for crystalline Cabazitaxel form IV in range 200 – 100 ppm.

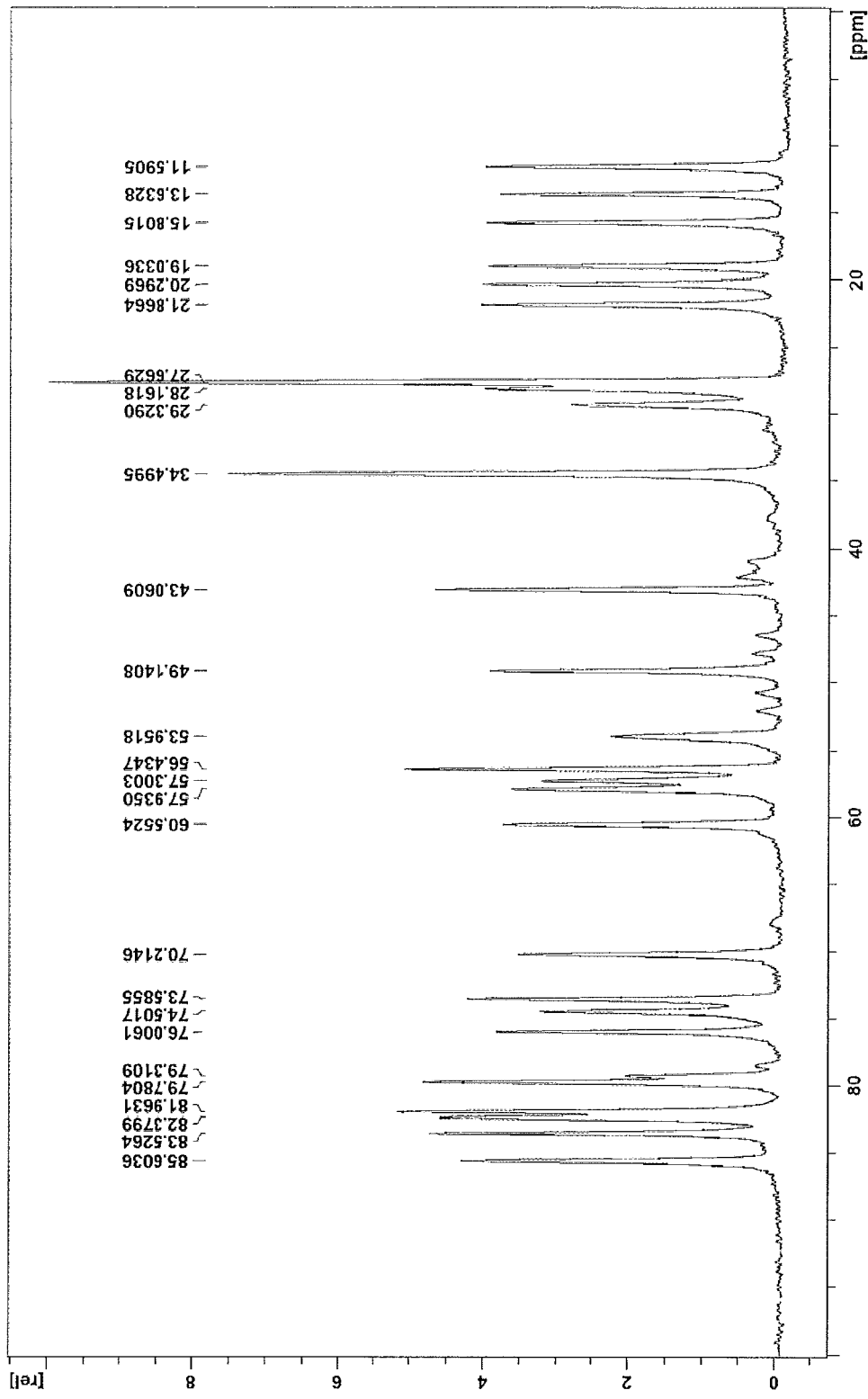
Figure 32 shows a detailed solid state $^{13}$C NMR spectrum for crystalline Cabazitaxel form IV in range 100 – 0 ppm.

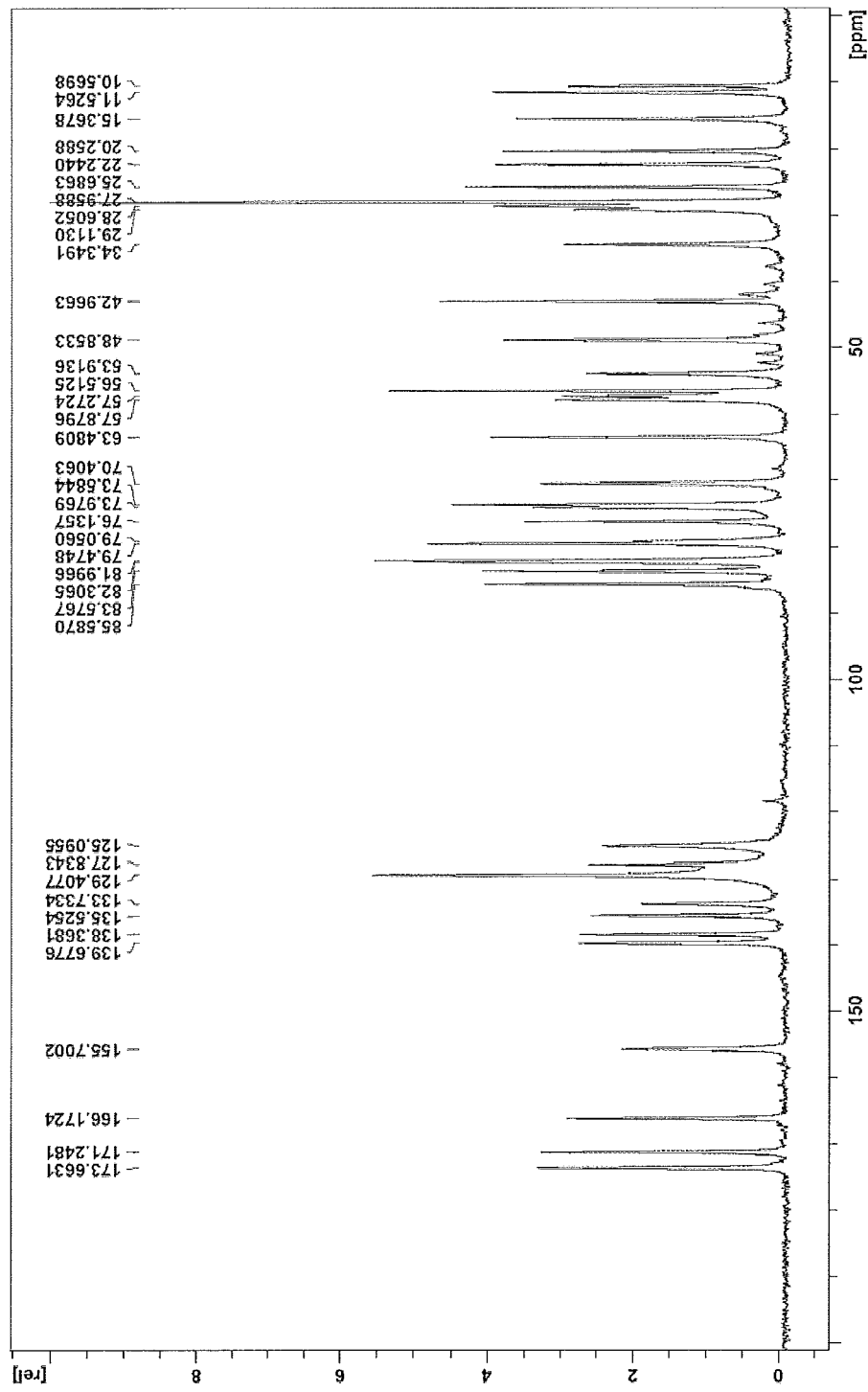
Figure 33 shows a full-width solid state $^{13}$C NMR spectrum for crystalline Cabazitaxel form V.

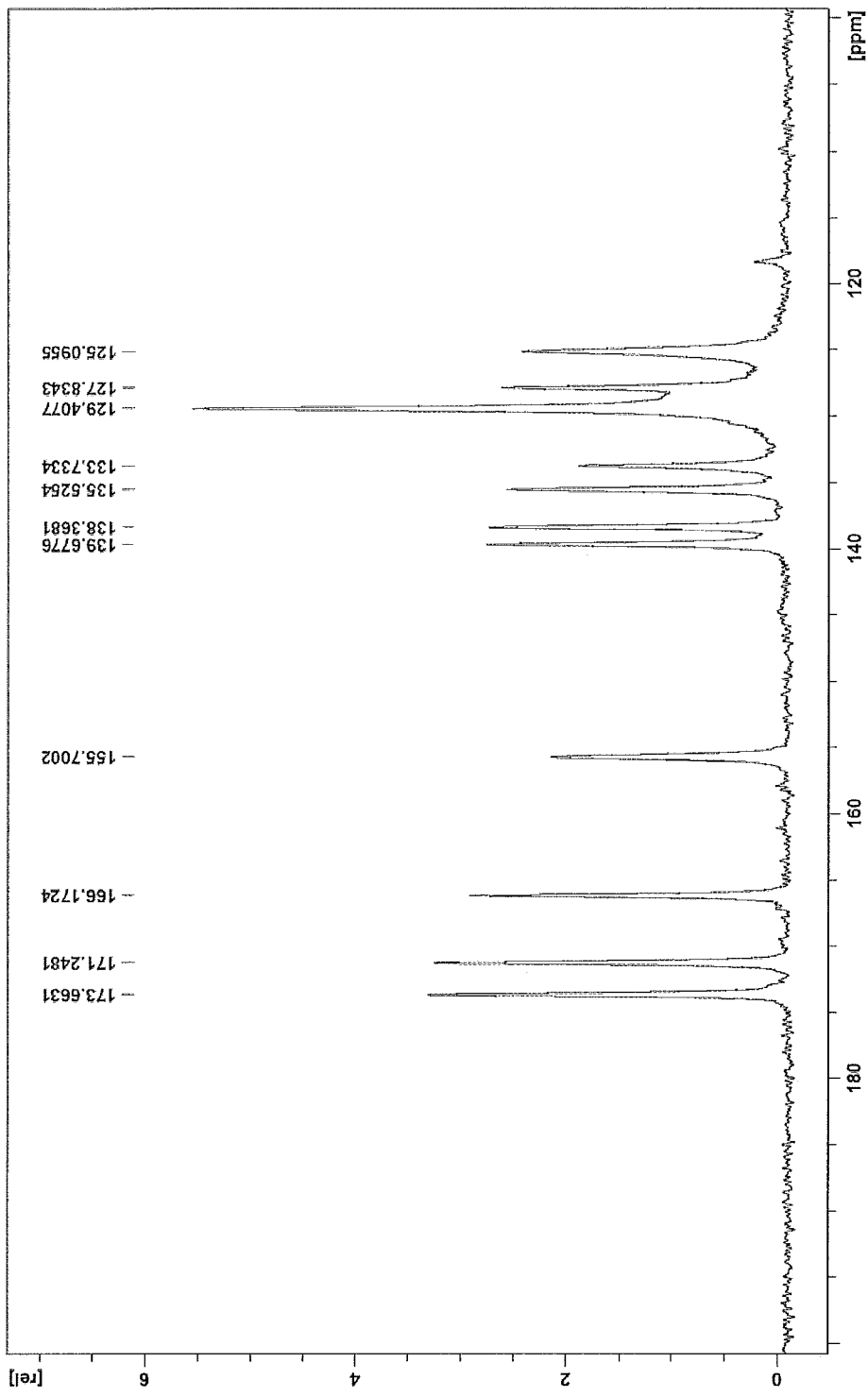
Figure 34 shows a detailed solid state $^{13}$C NMR spectrum for crystalline Cabazitaxel form V in range 200 – 100 ppm.

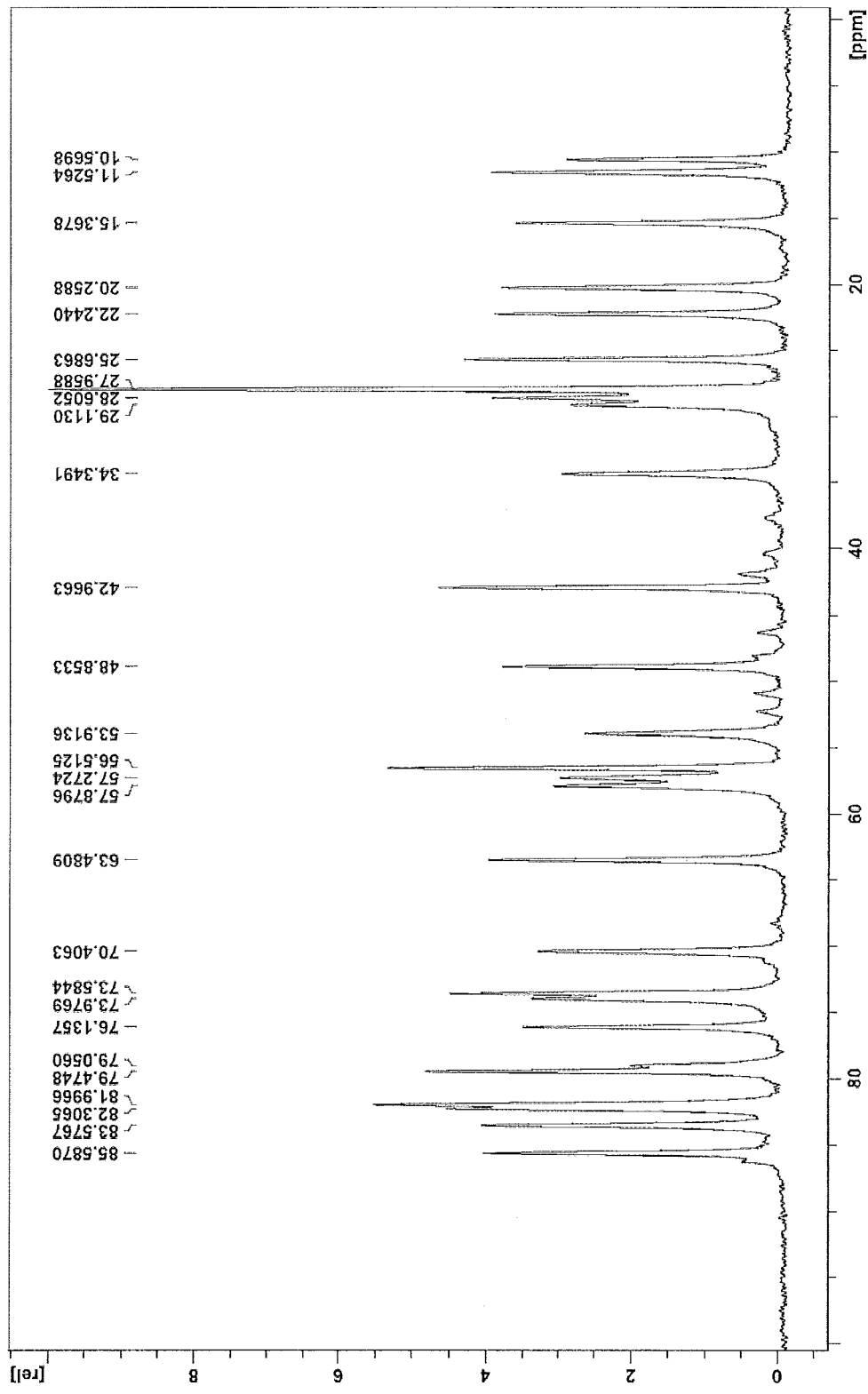
Figure 35 shows a detailed solid state $^{13}$C NMR spectrum for crystalline Cabazitaxel form V in range 100 – 0 ppm.

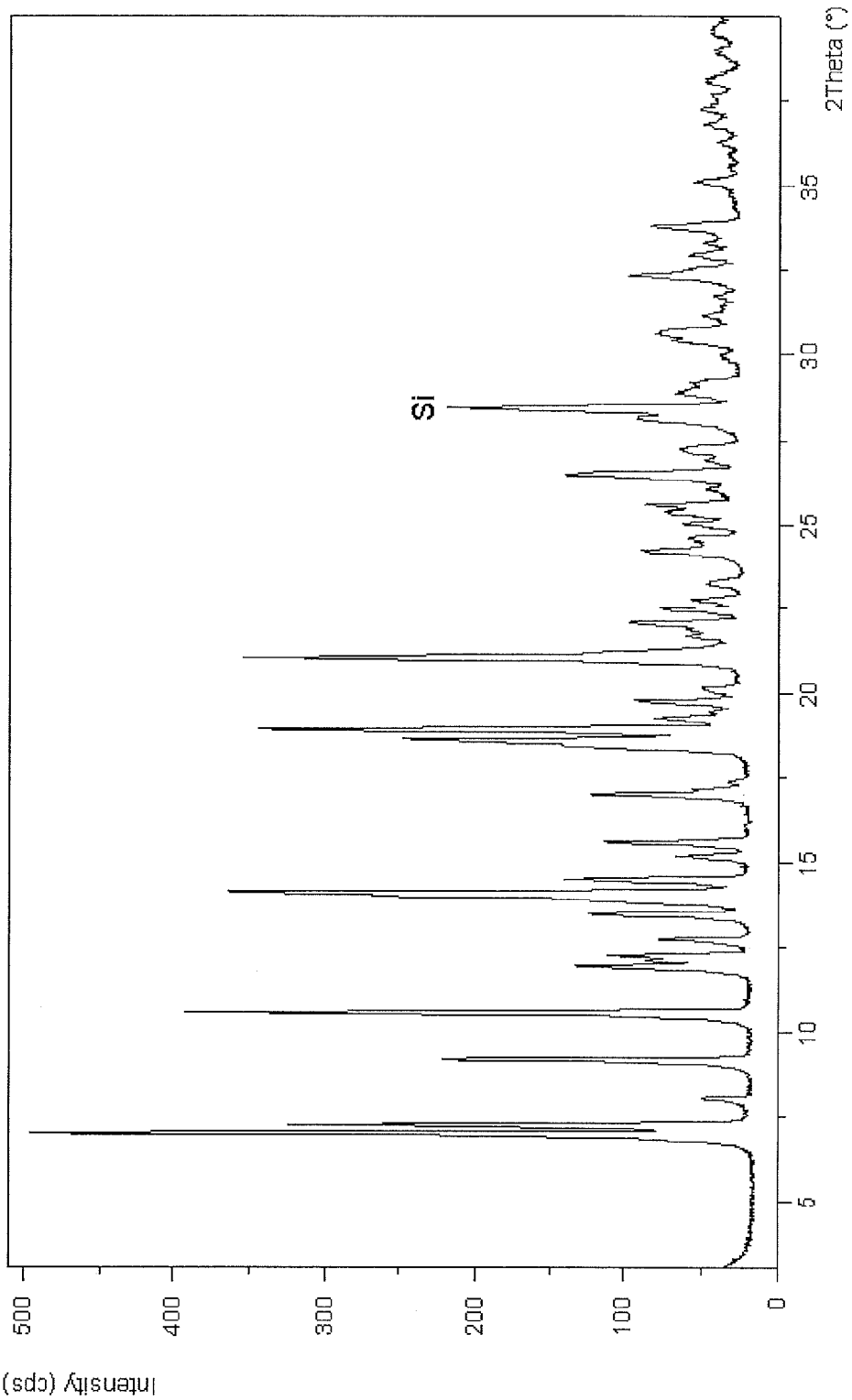
Figure 36 shows a PXRD pattern for crystalline triethylsilyl Cabazitaxel. The peak marked "Si" corresponds to the silicon internal standard

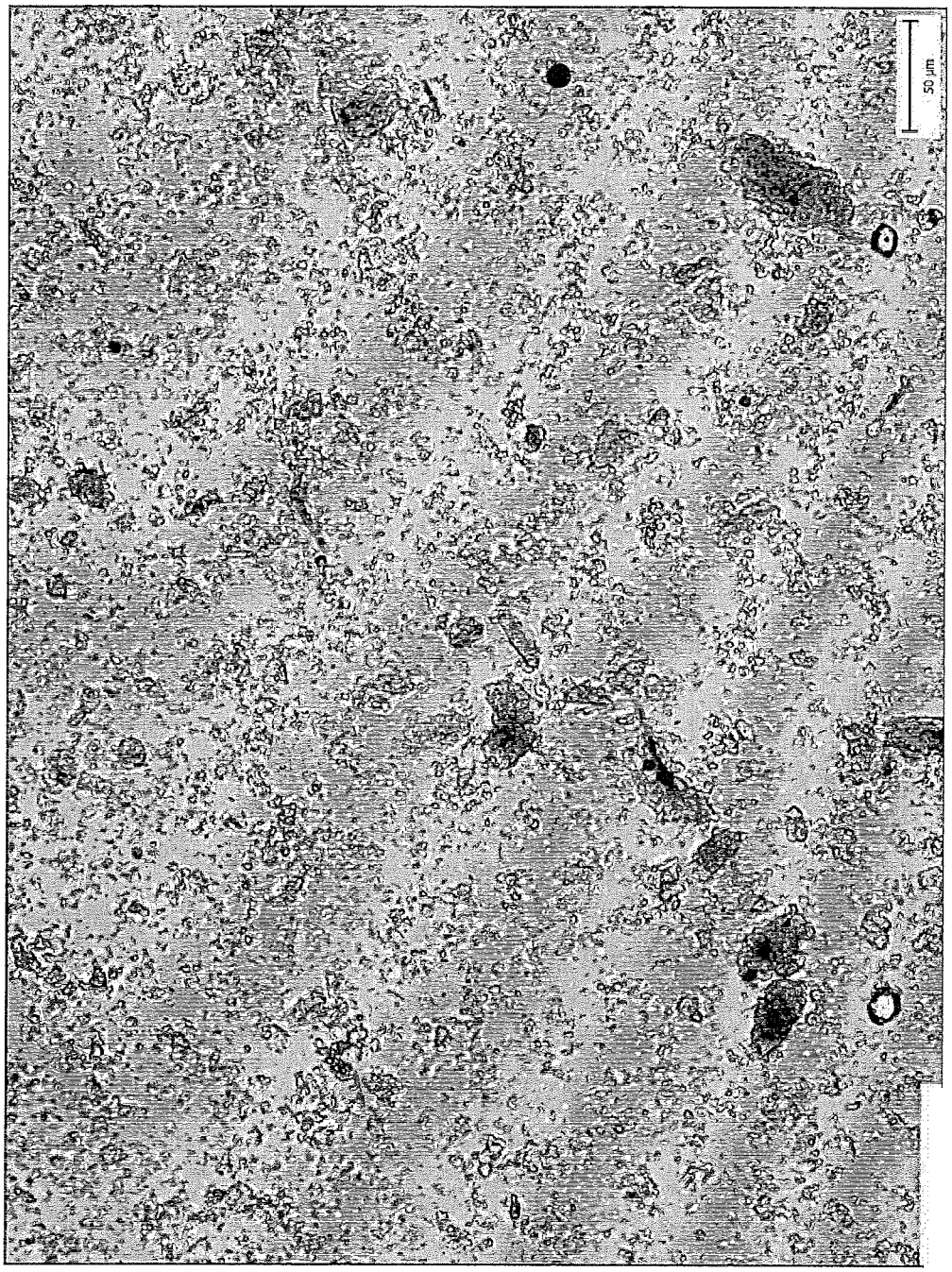
Figure 37 shows a microscopic image of amorphous Cabazitaxel in a powdery, non-foam form (The scale represents 50 μm).

SOLID STATE FORMS OF CABAZITAXEL AND PROCESSES FOR PREPARATION THEREOF

CROSS REFERENCE TO RELATED APPLICATIONS

This application is a continuation of International Application No. PCT/US2012/033061, filed Apr. 11, 2012, which claims the benefit of U.S. Provisional Application Nos. 61/474,572, filed Apr. 12, 2011; 61/517,954, filed Apr. 27, 2011; 61/486,894, filed May 17, 2011; 61/598,473, filed Feb. 14, 2012; and 61/607,875, filed Mar. 7, 2012; all of which are herein incorporated by reference in their entirety.

FIELD OF THE INVENTION

The present invention relates to solid state forms of Cabazitaxel, processes for preparation thereof and formulation thereof. Also provided herein is a process for preparing Cabazitaxel, via certain novel synthetic intermediates.

BACKGROUND OF THE INVENTION

Cabazitaxel, (αR,βS)-α-hydroxy-β-[[(1,1-dimethylethoxy)carbonyl]amino]-benzenepropanoic acid (2aR,4S,4aS,6R,9S,11S,12S,12aR,12bS)-12b-(acetyloxy)-12-(benzoyloxy)-2a,3,4,4a,5,6,9,10,11,12,12a,12b-dodecahydro-11-hydroxy-4,6-dimethoxy-4a,8,13,13-tetramethyl-5-oxo-7,11-methano-1H-cyclodeca[3,4]benz[1,2-b]oxet-9-yl ester, has the following chemical structure:

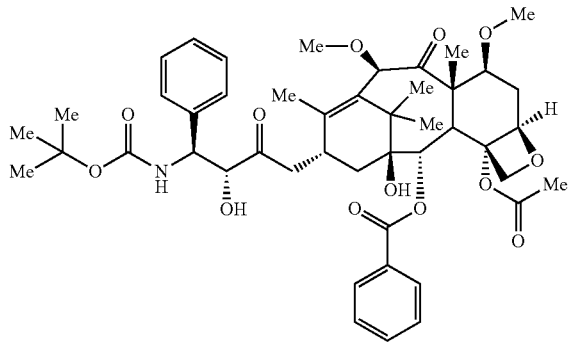 [SMILES: CO[C@H]1C(=O)[C@@]2(C)C([C@H](OC(=O)c3ccccc3)[C@]3(O)C[C@H](CC(=O)[C@H](O)[C@@H](NC(=O)OC(C)(C)C)c4ccccc4)C(C)=C1C3(C)C)[C@]1(OC(C)=O)CO[C@@H]1C[C@@H]2OC]

Cabazitaxel is a semi-synthetic taxoid derivative. It is marketed under the trade name JEVTANA® for the treatment of hormone-refractory prostate cancer.

Cabazitaxel and a process for its preparation are disclosed in U.S. Pat. No. 5,847,170. Cabazitaxel acetone solvate is disclosed in U.S. Pat. No. 7,241,907. Several solid state forms of Cabazitaxel are disclosed in WO 2009/115655.

Polymorphism, the occurrence of different crystal forms, is a property of some molecules and molecular complexes. A single molecule, like Cabazitaxel, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic finals. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life.

SUMMARY OF THE INVENTION

The present invention provides solid state forms of Cabazitaxel, processes for preparation thereof, and formulations comprising one or more of the solid state forms of Cabazitaxel.

The present invention also provides solid state forms of Cabazitaxel for use for preparing pharmaceutical compositions. The present invention further provides a pharmaceutical composition comprising one or more of the solid state forms of Cabazitaxel of the present invention. This pharmaceutical composition may additionally comprise at least one pharmaceutically acceptable excipient.

The present invention also provides a method of treating hormone-refractory prostate cancer by administering a therapeutically effective amount of a pharmaceutical composition comprising one or more of the solid state forms of Cabazitaxel of the present invention and optionally at least one pharmaceutically acceptable excipient to a patient in need thereof.

BRIEF DESCRIPTION OF THE FIGURES

FIG. 1 shows a powder X-ray diffraction pattern ("Powder XRD" or "PXRD") for crystalline Cabazitaxel form I.

FIG. 2 shows a Differential Scanning calorimetry ("DSC") thermogram for crystalline Cabazitaxel form I.

FIG. 3 shows a Thermogravimetric analysis ("TGA") thermogram for crystalline Cabazitaxel form I.

FIG. 4 shows a PXRD pattern for amorphous Cabazitaxel.

FIG. 5 shows a PXRD pattern for 7,10-dimethoxy-10-DAB (Compound 5).

FIG. 6 shows a PXRD pattern for crystalline Cabazitaxel form II.

FIG. 7 shows a DSC thermogram for crystalline Cabazitaxel form II.

FIG. 8 shows a TGA thermogram for crystalline Cabazitaxel form II.

FIG. 9 shows a PXRD pattern for crystalline Cabazitaxel form III.

FIG. 10 shows a DSC thermogram for crystalline Cabazitaxel form III.

FIG. 11 shows a TGA thermogram for crystalline Cabazitaxel form III.

FIG. 12 shows a PXRD pattern for crystalline Cabazitaxel form IV.

FIG. 13 shows a DSC thermogram for crystalline Cabazitaxel form IV.

FIG. 14 shows a TGA thermogram for crystalline Cabazitaxel form IV.

FIG. 15 shows a PXRD pattern for crystalline Cabazitaxel form V.

FIG. 16 shows a DSC thermogram for crystalline Cabazitaxel form V.

FIG. 17 shows a TGA thermogram for crystalline Cabazitaxel form V.

FIG. 18 shows a full-width solid state $^{13}$C NMR spectrum for amorphous Cabazitaxel.

FIG. 19 shows a solid state $^{13}$C NMR spectrum for amorphous Cabazitaxel in the range 200-100 ppm.

FIG. 20 shows a solid state $^{13}$C NMR spectrum for amorphous Cabazitaxel in the range 100-0 ppm.

FIG. 21 shows a full-width solid state $^{13}$C NMR spectrum for crystalline Cabazitaxel form I.

FIG. 22 shows a solid state $^{13}$C NMR spectrum for crystalline Cabazitaxel form I in the range 200-100 ppm.

FIG. 23 shows a solid state $^{13}$C NMR spectrum for crystalline Cabazitaxel form I in the range 100-0 ppm.

FIG. 24 shows a full-width solid state $^{13}$C NMR spectrum for crystalline Cabazitaxel form II.

FIG. 25 shows a solid state $^{13}$C NMR spectrum for crystalline Cabazitaxel form II in the range 200-100 ppm.

FIG. 26 shows a solid state $^{13}$C NMR spectrum for crystalline Cabazitaxel form II in the range 100-0 ppm.

FIG. 27 shows a full-width solid state $^{13}$C NMR spectrum for crystalline Cabazitaxel form III.

FIG. 28 shows a solid state $^{13}$C NMR spectrum for crystalline Cabazitaxel form III in the range 200-100 ppm.

FIG. 29 shows a solid state $^{13}$C NMR spectrum for crystalline Cabazitaxel form III in the range 100-0 ppm.

FIG. 30 shows a full-width solid state $^{13}$C NMR spectrum for crystalline Cabazitaxel form IV.

FIG. 31 shows a solid state $^{13}$C NMR spectrum for crystalline Cabazitaxel form IV in the range 200-100 ppm.

FIG. 32 shows a solid state $^{13}$C NMR spectrum for crystalline Cabazitaxel form IV in the range 100-0 ppm.

FIG. 33 shows a full-width solid state $^{13}$C NMR spectrum for crystalline Cabazitaxel form V.

FIG. 34 shows a detailed solid state $^{13}$C NMR spectrum for crystalline Cabazitaxel form V in range 200-100 ppm.

FIG. 35 shows a detailed solid state $^{13}$C NMR spectrum for crystalline Cabazitaxel form V in range 100-0 ppm.

FIG. 36 shows a PXRD pattern for crystalline triethylsilyl Cabazitaxel.

FIG. 37 shows a microscopic image of amorphous Cabazitaxel in a powdery, non-foamy form.

DETAILED DESCRIPTION OF THE INVENTION

The present invention provides solid state forms of Cabazitaxel, processes for preparation thereof and formulations thereof. Also provided herein is a process for preparing Cabazitaxel, said process proceeding via certain novel synthetic intermediates.

The solid state forms of the present invention have advantageous properties selected from at least one of: chemical purity, flowability, solubility, morphology or crystal habit, stability—such as storage stability, stability to dehydration, stability to polymorphic conversion, low hygroscopicity, and low content of residual solvents.

A crystal form may be referred to herein as being characterized by graphical data substantially "as depicted in" a figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A solid state form may be referred to herein as being characterized by data selected from two or more different data groupings, for example, by a powder XRD pattern having a group of specific peaks; or by a powder XRD pattern as shown in a figure depicting a diffractogram, or by "a combination thereof" (or "combinations thereof," or "any combination thereof"), These expressions, e.g., "any combination thereof" contemplate that the skilled person may characterize a crystal form using any combination of the recited characteristic analytical data. For example, the skilled person may characterize a crystal form using a group of four or five characteristic powder XRD peaks, and supplement that characterization with one or more additional features observed in the powder X-ray diffractogram, e.g., an additional peak, a characteristic peak shape, a peak intensity, or even the absence of a peak at some position in the powder XRD pattern. Alternatively, the skilled person may in some instances characterize a crystal form using a group of four or five characteristic powder XRD peaks and supplement that characterization with one or more additional features observed using another analytical method, for example, using one or more characteristic peaks in a solid state NMR spectrum, or characteristics of the DSC thermogram of the crystal form that is being characterized.

A solid state form may be referred to herein as being characterized by having powder XRD peaks and also, optionally by having no peak in a certain specific and defined range. The term optionally will be understood as both options, i.e. 1) having powder XRD peaks; and also 2) having powder XRD peaks and also having no peaks at said certain specific and defined, are considered as embodiments of the present invention.

As used herein, the expression "chemical shift difference" refers to the difference in chemical shifts between a reference peak and another peak in the same NMR spectrum. These chemical shift differences serve to provide an additional analytical measurement for a substance, for example a Cabazitaxel crystal form of the present invention, which will compensate for a phenomenon that may occur in NMR spectroscopy wherein a shift in the entire solid-state NMR "fingerprint" is observed. Such a shift in the NMR peaks may occur, for example as a result of variations in the instrumentation, the temperature, or the calibration method used in the NMR analysis. This shift in the solid-state NMR "fingerprint", having chemical shift resonances at a certain positions, is such that even though the individual chemical shifts of the peaks have moved, all the peaks in the spectrum are moved be the same amount, such that the difference between chemical shifts of each peak and a reference peak in the spectrum is retained. Thus, this shift may be used as a reliable characterization of the material being analyzed.

In the present patent application the chemical shift differences were calculated by subtracting the chemical shift value of the peak exhibiting the lowest chemical shift (reference peak) in the solid state $^{13}$C NMR spectrum in the range of 100 to 180 ppm from chemical shift value of another (observed) peak in the same $^{13}$CNMR spectrum in the range of 0 to 180 ppm.

A crystal form (or polymorph) may be referred to herein as substantially free of any other crystalline (or polymorphic) forms. As used herein in this context, the expression "substantially free of any other forms" will be understood to mean that the crystalline form contains 20% or less, 10% or less, 5% or less, 2% or less, or 1% or less of any other forms of the subject compound as measured, for example, by PXRD.

Thus, polymorphs of Cabazitaxel described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Cabazitaxel. Accordingly, in some embodiments of the invention, the described polymorphs of Cabazitaxel may contain from 1% to 20% (w/w), from 5% to 20% (w/w), or from 5% to 10% (w/w) of one or more other crystal forms of Cabazitaxel.

As used herein, the expression "room temperature" refers to a temperature from about 20° C. to about 30° C. Usually, room temperature ranges from about 20° C. to about 25° C.

As used herein, the term "overnight" refers to a period of from about 15 to about 20 hours, typically from about 16 to about 20 hours.

As used herein, the expression "wet crystalline form" refers to a polymorph that was not dried using any conventional techniques to remove residual solvent. Such conventional techniques include, but are not limited to, evaporation, vacuum drying, oven drying, drying under nitrogen flow etc.

As used herein, the expression "dry crystalline form" refers to a polymorph that was dried using any conventional techniques to remove residual solvent. Such conventional techniques include, but are not limited to, evaporation, vacuum drying, oven drying, drying under nitrogen flow, etc.

As used herein, and unless stated otherwise, the term "anhydrous" in relation to crystalline Cabazitaxel relates to a crystalline Cabazitaxel which contains not more than 1% (w/w) of either water or organic solvents as measured, for example, by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless stated otherwise, the terms "powder" or "powdery" refer to a solid compound in the forms of particles or granules, wherein the particles or granules can be poured. Preferably, the powders are solid, loose and dry particles.

As used herein, and unless indicated otherwise, the term "polymorphic stability" in relation to the crystalline forms of Cabazitaxel means that there is less than 20%, 10%, 5%, 1%, 0.5% or 0.1% conversion of crystalline Cabazitaxel to any other solid state form of Cabazitaxel under the specified conditions, as measured by PXRD. In some embodiments, the conversion is 0.5%-20%, 0.5%-10% or 0.5%-5% or 0.5%-1% or 0.1%-1%, or 0.1%-0.5%.

As used herein and unless indicated otherwise, the term non-hygroscopic in relation to solid state forms of Cabazitaxel refers to an absorption of less than 0.2% (w/w) of atmospheric water to the crystalline forms of Cabazitaxel in the above specified conditions, as measured by suitable analytical methods, such as TGA or Karl-Fischer coulometric titration.

In one embodiment the present invention encompasses crystalline Cabazitaxel designated as form I. Form I can be characterized by a solid state $^{13}$C NMR spectrum with peaks at 167.0, 59.0, 50.2, 44.2 and 35.5 ppm 0.2 ppm; or by a solid state $^{13}$C NMR spectrum having chemical shift differences between said characteristic peaks at 167.0, 59.0, 50.2, 44.2 and 35.5 ppm±0.2 ppm and a reference peak at 126.2±0.2 ppm of: 40.8, −67.1, −76.0, −82.0 and −90.7 ppm±0.1 ppm, respectively; or by a solid state $^{13}$C NMR spectrum substantially as depicted in any one of FIGS. 21-23; or by a combination thereof.

Form I, as characterized by the NMR data above, can be further characterized by data selected from: a solid state $^{13}$C NMR spectrum with peaks at 136.4, 84.4, 80.7, 30.9 and 16.5 ppm±0.2 ppm; a solid state $^{13}$C NMR spectrum having chemical shift differences between said characteristic peaks at 136.4, 84.4, 80.7, 30.9 and 16.5 ppm±0.2 ppm and a reference peak at 126.2±0.2 ppm of 10.2, −41.8, −45.4, −95.3 and −109.7 ppm±0.1 ppm, respectively; and combinations thereof.

The above form I can be a toluene solvate.

Form I toluene solvate can be characterized by data selected from: a powder X-ray diffraction pattern having peaks at 7.6, 8.0, 8.6, 10.1 and 14.2 degrees two theta±0.1 degrees two theta, and optionally having no peak in the area from 10.4 to 12.4 degrees two theta; by a powder X-ray diffraction pattern substantially as depicted in FIG. 1; by a solid state $^{13}$C NMR data as described above; and combinations thereof.

The Form I toluene solvate, as characterized above, can be further characterized by data selected from: an X-ray powder diffraction pattern having peaks at 7.6, 8.0, 8.6, 10.1 and 14.2 degrees two theta±0.1 degrees two theta and optionally having no peak in the area from 10.4 to 12.4 degrees two theta, and also having an additional one, two, three, four or five peaks selected from 13.2, 14.8, 17.4, 20.4 and 23.9 degrees 2-theta±0.1 degrees 2-theta; a solid state $^{13}$C NMR spectrum with peaks at 136.4, 84.4, 80.7, 30.9 and 16.5 ppm±0.2 ppm; a solid state $^{13}$C NMR spectrum having chemical shift differences between said characteristic peaks at 136.4, 84.4, 80.7, 30.9 and 16.5 ppm±0.2 ppm and a reference peak at 126.2±0.2 ppm of 10.2, −41.8, −45.4, −95.3 and −109.7 ppm±0.1 ppm, respectively; a DSC thermogram substantially as depicted in FIG. 2; a DSC melting peak at about 163° C.±4° C., or 163.2° C. and DSC melting onset at about 155° C.±4° C., or 154.6° C.; a TGA thermogram substantially as depicted in FIG. 3; residual toluene content of 11.0%±2%, preferably about 11%, w/w as determined by GC; and combinations thereof. The theoretical content of toluene for monosolvate of cabazitaxel is about 9.9% w/w.

Alternatively, the above Form I toluene solvate can be characterized by a powder X-ray diffraction pattern having peaks at 7.6, 8.0, 8.6, 10.1, 12.6, 12.8, 13.2, 13.9, 14.2, 14.8, 15.1, 15.2, 15.6, 15.9, 16.0, 16.7, 16.9, 17.1, 17.4, 17.9, 18.8, 19.7, 19.9, 20.2, 20.4, 20.8, 21.1, 21.7, 22.1, 22.5, 22.7, 22.9, 23.4, 23.9, 24.4, 24.7, 25.0, 25.3, 26.0, 26.5, 27.0, 27.5, 27.8, 27.9, 28.3, 28.9, 30.1, 30.4, 30.7, 31.1, 31.4, 31.8, 32.1, 32.4, 33.1, 34.3, 35.1, 36.2, 36.5, 37.2, 37.9 and 38.4 degrees theta±0.1 degrees 2-theta and having no peak in the area from 10.4 to 12.4 degrees two theta.

Form I can be characterized by any combination of the above data.

Form I has advantageous properties including at least one of: chemical purity, flowability, solubility, morphology or crystal habit, stability—such as storage stability, stability to dehydration, stability to polymorphic conversion, low hygroscopicity, low content of residual solvents. Particularly, the crystalline Cabazitaxel Form I of the present invention is a low-hygroscopicity form, and it does not convert to any other forms of Cabazitaxel in various relative humidity (RH) conditions, such as normal atmospheric humidity, 60%, 80% and 100% RH and at a temperature of about room temperature.

In another embodiment the present invention encompasses amorphous Cabazitaxel.

The amorphous form can be characterized by a powder X-ray diffraction pattern substantially as depicted in FIG. 4. The amorphous Cabazitaxel can be further characterized by data selected from: a solid state $^{13}$C NMR spectrum with peaks at 128.3, 81.1, 75.7, 56.9, 47.6, 31.9 and 28.1 ppm±0.2 ppm; a solid state $^{13}$C NMR spectrum substantially as depicted in any one of FIGS. 18-20; and combinations thereof.

Particularly, the present invention also encompasses amorphous Cabazitaxel in a powdery, non-foamy form. This amorphous form can be characterized by the powder X-ray diffraction pattern substantially as depicted in FIG. 4.

FIG. 37 provides a microscopic image of amorphous Cabazitaxel in a powdery, non-foamy form The above amorphous Cabazitaxel in a powdery, non-foamy form can be easily used to obtain a fine powder. This allows for easy processability (i.e. better handling, filtration, drying and transferring the material off the filter) and better storage of the final active ingredient ("API"), in comparison to a foamy matter which creates crust upon drying and is difficult to handle. Additionally, as opposed to a foamy material, amorphous Cabazitaxel in a powdery, non-foamy form is preferred for use in preparation of pharmaceutical formulation, as it can be used in common formulation techniques, such as compression and granulation, it allows better handling of the API during the formulation steps and better quantification of the API.

The amorphous Cabazitaxel in a powdery, non-foamy form of the present invention can be prepared by a process comprising precipitating Cabazitaxel from a mixture of a solvent and an antisolvent. The process comprises dissolving Cabazitaxel in a solvent such as toluene or tetrahydrofuran ("THF"), and combining the resulting solution with an antisolvent, like heptane or hexane, to obtain a suspension from which amorphous Cabazitaxel precipitates.

Alternatively, the process can be done by precipitating Cabazitaxel from a two phase system. The process comprises combining a solution of Cabazitaxel with a mixture of water and a water-immiscible organic solvent, for example water and hexane, to obtain a two phase system from which the amorphous Cabazitaxel precipitates. The starting solution of Cabazitaxel can be concentrated, i.e. a Cabazitaxel in a form of a syrup can be used.

In another embodiment the present invention encompasses crystalline Cabazitaxel designated as form II. Form II can be characterized by data selected from: a solid state $^{13}$C NMR spectrum with peaks at 174.3, 170.8, 166.5, 137.7, and 135.9 ppm 0.2 ppm; a solid state $^{13}$C NMR spectrum having chemical shift differences between said characteristic peaks at 174.3, 170.8, 166.5, 137.7, and 135.9 ppm±0.2 ppm and a reference peak at 125.1±0.2 ppm of 49.2, 45.7, 41.4, 12.6 and 10.8 ppm 0.1 ppm, respectively; a solid state $^{13}$C NMR spectrum substantially as depicted in any one of FIGS. 24-26; and combinations thereof.

From II, as characterized above, can be further characterized by data selected from: a solid state $^{13}$C NMR spectrum with peaks at 138.6, 74.1, 72.1 and 71.4 ppm±0.2 ppm; a solid state $^{13}$C NMR spectrum having chemical shift differences between said characteristic peaks at 138.6, 74.1, 72.1 and 71.4 ppm±0.2 ppm and a reference peak at 125.1±0.2 ppm of 13.5, −51.0, −53.1 and −53.7 ppm±0.1 ppm, respectively; and combinations thereof.

The above form II can be a methyl tert-butyl ether ("MTBE") solvate.

Foam II MTBE solvate can be characterized by data selected from: a powder X-ray diffraction pattern having peaks at 7.4, 7.7, 8.9, 12.1 and 13.2 degrees two theta±0.1 degrees two theta and optionally having no peak in the area from 10.4 to 11.9 degrees two theta; a powder X-ray diffraction pattern substantially as depicted in FIG. 6; a solid state $^{13}$C NMR data as described above; and combinations thereof.

The above Form II MTBE solvate can be further characterized by data selected from: an X-ray powder diffraction pattern having peaks at 7.4, 7.7, 8.9, 12.1 and 13.2 degrees two theta±0.1 degrees two theta and optionally having no peak in the area from 10.4 to 11.9 degrees two theta, and also having an additional one, two, three, four or five peaks selected from 10.1, 12.6, 12.7, 16.1 and 19.3 degrees 2-theta±0.1 degrees 2-theta; a solid state $^{13}$C NMR spectrum with peaks at 138.6, 74.1, 72.1 and 71.4 ppm±0.2 ppm; a solid state $^{13}$C NMR spectrum having chemical shift differences between said characteristic peaks at 138.6, 74.1, 72.1 and 71.4 ppm±0.2 ppm and a reference peak at 125.1±0.2 ppm of 13.5, −51.0, −53.1 and −53.7 ppm±0.1 ppm, respectively; a DSC thermogram substantially as depicted in FIG. 7; a DSC melting peak at about 163° C.±4° C., or 163.3° C. and a DSC melting onset at about 153° C.±4° C., or 153.0° C.; a TGA thermogram substantially as depicted in FIG. 8; a residual MTBE content of 9.7%±2%, preferably about 9.7%, w/w as determined by GC; and combinations thereof. The theoretical content of MTBE for monosolvate of cabazitaxel is about 9.5% w/w.

Alternatively, Form II MTBE solvate an be characterized by a powder X-ray diffraction pattern having peaks at 7.4, 7.7, 8.9, 10.1, 12.1, 12.6, 12.7, 13.2, 13.5, 14.5, 14.8, 15.3, 15.6, 16.1, 16.9, 17.7, 18.0, 18.4, 18.6, 18.6, 19.3, 20.3, 21.1, 21.2, 21.5, 21.8, 22.2, 22.6, 23.1, 23.5, 23.8, 24.4, 25.2, 25.7, 26.2, 26.8, 27.7, 28.8, 29.5, 29.9, 30.3, 30.9, 31.2, 31.7, 33.5, 34.1, 34.6, 34.8, 35.4, 35.8, 36.6, 37.5, 38.4, 39.0 and 39.2 degrees two theta±0.1 degrees 2-theta and having no peak in the area from 10.4 to 11.9 degrees two theta.

Form II MTBE solvate can be characterized by any combination of the above data.

The above Form II has advantageous properties including at least one of: chemical purity, flowability, solubility, morphology or crystal habit, stability—such as storage stability, stability to dehydration, stability to polymorphic conversion, low hygroscopicity, low content of residual solvents. Particularly, the crystalline Cabazitaxel Form II of the present invention is low-hygroscopicity form and it does not convert to any other forms of Cabazitaxel in various relative humidly (RH) conditions, such as normal atmospheric humidy, 60%, 80% and 100% RH and at a temperature of about room temperature.

In yet another embodiment the present invention encompasses crystalline Cabazitaxel designated as form III. Form III can be characterized by data selected from: a solid state $^{13}$C NMR spectrum with peaks at 139.8 127.8, 63.4, 25.4 and 23.5 ppm±0.2 ppm; a solid state $^{13}$C NMR spectrum having chemical shift differences between said characteristic peaks at 139.8 127.8, 63.4, 25.4 and 23.5 ppm±0.2 ppm and a reference peak at 125.1±0.2 ppm of 14.8, 2.8, −61.7, −99.6 and −101.6 ppm±0.1 ppm, respectively; a solid state $^{13}$C NMR spectrum substantially as depicted in any one of FIGS. 27-29; and combinations thereof.

Form III, as characterized above, can be further characterized by data selected from: a solid state $^{13}$C NMR spectrum with peaks at 173.5, 133.6, 129.3 and 15.4 ppm±0.2 ppm; a solid state $^{13}$C NMR spectrum having chemical shift differences between said characteristic peaks at 173.5, 133.6, 129.3 and 15.4 ppm±0.2 ppm and a reference peak at 125.1±0.2 ppm of 48.4, 8.5, 4.2 and −109.6 ppm±0.1 ppm, respectively; and by combinations thereof.

The above form III can be a 2-propanol solvate.

Form III 2-propanol solvate can be characterized by data selected from: a powder X-ray diffraction pattern having peaks at 7.4, 9.0, 10.3, 13.3 and 13.6 degrees two theta±0.1 degrees two theta and optionally having no peak in the area from 10.5 to 12.1 degrees two theta; by a powder X-ray diffraction pattern substantially as depicted in FIG. 9; by a solid state $^{13}$C NMR data as described above; and combinations thereof.

The above Form III 2-propanol solvate can be further characterized by data selected from: an X-ray powder diffraction pattern having peaks at 7.4, 9.0, 10.3, 13.3 and 13.6 degrees two theta+0.1 degrees two theta and optionally having no peak in the area from 10.5 to 12.1 degrees two theta and also having an additional one, two, three, four or five peaks selected from 7.9, 12.9, 15.2, 15.3 and 19.5 degrees 2-theta±0.1 degrees 2-theta; a solid state $^{13}$C NMR spectrum with peaks at 173.5, 133.6, 129.3 and 15.4 ppm 0.2 ppm; a solid state $^{13}$C NMR spectrum having chemical shift differences between said characteristic peaks at 173.5, 133.6, 129.3 and 15.4 ppm±0.2 ppm and a reference peak at 125.1±0.2 ppm of 48.4, 8.5, 4.2 and −109.6 ppm±0.1 ppm, respectively; a DSC thermogram substantially as depicted in FIG. 10; a DSC melting peak at about 166.0° C. 4° C. and a DSC melting onset at about 149° C.±4° C., or about 148.8° C.; a TGA thermogram substantially as depicted in FIG. 11; a residual 2-propanol content of 7.0%±1.5% w/w, preferably about 7.0% w/w as determined by GC; and combinations thereof. The theoretical content of 2-propanol for monosolvate of cabazitaxel is about 6.7% w/w.

Alternatively, Form III 2-propanol solvate can be characterized by a powder X-ray diffraction pattern having peaks at 7.4, 7.9, 9.0, 10.2, 10.3, 12.6, 12.9, 13.3, 13.6, 14.4, 14.8, 15.2, 15.3, 15.6, 15.8, 16.0, 16.6, 17.0, 17.2, 17.7, 18.0, 18.3, 18.8, 19.5, 19.7, 20.5, 20.7, 21.1, 21.4, 21.8, 21.9, 22.2, 22.8, 23.1, 23.5, 23.7, 24.0, 24.3, 24.8, 25.2, 25.3, 25.8, 26.3, 26.9, 27.1, 27.5, 27.8, 28.8, 29.0, 29.6, 30.2, 30.7, 30.9, 31.2, 31.6, 32.3, 33.0, 33.6, 34.2, 34.9, 35.2, 35.5, 35.8, 36.2, 36.7, 37.1, 37.8, 38.1, 38.5, 38.9, 39.2, 39.3 and 39.7 degrees two theta±0.1 degrees 2-theta and having no peak in the area from 10.5 to 12.1 degrees two theta.

Alternatively, form III 2-propanol solvate can be characterized by the following unit cell data:

| | |
|---|---|
| Cell length a | 11.72 Å |
| Cell length b | 17.23 Å |
| Cell length c | 12.57 Å |
| Cell angle alpha | 90° |
| Cell angle beta | 107.80° |
| Cell angle gamma | 90° |
| Cell volume | 2417 Å$^3$ |

-continued

| | |
|---|---|
| Temperature | 190 K |
| Symmetry cell setting | Monoclinic |
| Symmetry space group | P2$_1$ |

Form III 2-propanol solvate can be characterized by any combination of the above data.

The above form III has advantageous properties including at least one of: chemical purity, flowability, solubility, morphology or crystal habit, stability—such as storage stability, stability to dehydration, stability to polymorphic conversion, low hygroscopicity, low content of residual solvents.

Particularly, the crystalline Cabazitaxel form III of the present invention is polymorphically stable for a period of at least 6 months at either (1) a temperature of about 25° C. and 60% relative humidity (RH) or (2) at a temperature of about 40° C. and 75% RH. In addition, the crystalline Cabazitaxel Form III of the present invention is a low-hygroscopicity form, and it does not convert to any other solid state forms of Cabazitaxel in various relative humidly (RH) conditions, such as normal atmospheric humidy, 60%, 80% and 100% RH and at a temperature of about room temperature.

In one embodiment the present invention encompasses crystalline Cabazitaxel designated as foam IV. Form IV can be characterized by data selected from: a solid state $^{13}$C NMR spectrum with peaks at 128.4, 60.6, 19.0 and 13.6 ppm±0.2 ppm; by a solid state $^{13}$C NMR spectrum having chemical shift differences between said characteristic peaks at 128.4, 60.6, 19.0 and 13.6 ppm±0.2 ppm and a reference peak at 125.2±0.2 ppm of 3.2, −64.7, −106.2 and −111.6 ppm±0.1 ppm, respectively; by a solid state $^{13}$C NMR spectrum substantially as depicted in any one of FIGS. 30-32; and by combinations thereof.

Form IV, as characterized above, can be further characterized by data selected from: a solid state $^{13}$C NMR spectrum with peaks at 173.3, 139.5, 133.9 and 74.5 ppm±0.2 ppm; a solid state $^{13}$C NMR spectrum having chemical shift differences between said characteristic peaks at 173.3, 139.5, 133.9 and 74.5 ppm±0.2 ppm and a reference peak at 125.2±0.2 ppm of 48.1, 14.3, 8.7 and −50.7 ppm 10.1 ppm, respectively; and by combinations thereof.

The above form IV can be a n-butanol solvate.

Form IV n-butanol solvate can be characterized by data selected from: a powder X-ray diffraction pattern having peaks at 7.4, 7.9, 8.8, 12.9 and 13.5 degrees two theta±0.1 degrees two theta and optionally having no peak in the area from 10.4 to 12.2 degrees two theta; a powder X-ray diffraction pattern substantially as depicted in FIG. 12; a solid state $^{13}$C NMR data as described above; and combinations thereof.

Form IV n-butanol solvate can be further characterized by data selected from: an X-ray powder diffraction pattern having peaks at 7.4, 7.9, 8.8, 12.9 and 13.5 degrees two theta±0.1 degrees two theta and optionally having no peak in the area from 10.4 to 12.2 degrees two theta, and also having an additional one, two, three, four or five peaks selected from 10.2, 12.6, 19.0, 19.7 and 26.6 degrees 2-theta±0.1 degrees 2-theta; a solid state $^{13}$C NMR spectrum with peaks at 173.3, 139.5, 133.9 and 74.5 ppm±0.2 ppm; a solid state $^{13}$C NMR spectrum having chemical shift differences between said characteristic peaks at 173.3, 139.5, 133.9 and 74.5 ppm±0.2 ppm and a reference peak at 125.2±0.2 ppm of 48.1, 14.3, 8.7 and −50.7 ppm±0.1 ppm, respectively; a DSC thermogram substantially as depicted in FIG. 13; a DSC melting peak at about 168° C.±4° C., or 167.9° C. and a DSC melting onset at about 160° C.±4° C., or 159.8° C.; a TGA thermogram substantially as depicted in FIG. 14; a residual n-butanol content of 8.3%±2.0% w/w, preferably about 8.3% w/w as determined by GC; and combinations thereof. The theoretical content of n-butanol for monosolvate of cabazitaxel is about 7.9% w/w.

Alternatively, Form IV n-butanol solvate can be characterized by a powder X-ray diffraction pattern having peaks at 7.4, 7.9, 8.8, 10.2, 12.6, 12.9, 13.5, 14.3, 14.9, 15.0, 15.2, 15.7, 16.5, 17.0, 17.2, 17.6, 18.1, 18.3, 18.7, 19.0, 19.7, 20.5, 21.0, 21.6, 22.1, 22.3, 22.8, 23.2, 23.4, 23.6, 23.9, 24.2, 24.5, 24.8, 25.0, 25.4, 25.8, 26.1, 26.6, 27.1, 27.6, 28.1, 28.7, 29.5, 30.1, 30.4, 30.8, 31.3, 31.7, 31.9, 32.5, 32.7, 33.8, 34.2, 35.1, 35.7, 37.0, 37.6, 37.9, 38.4, 39.0 and 39.6 degrees two theta±0.1 degrees 2-theta and having no peak in the area from 10.4 to 12.2 degrees two theta.

Form IV n-butanol solvate can be characterized by any combination of the above data.

The above form IV has advantageous properties including at least one of: chemical purity, flowability, solubility, morphology or crystal habit, stability—such as storage stability, stability to dehydration, stability to polymorphic conversion, low hygroscopicity, low content of residual solvents. Particularly, the crystalline Cabazitaxel Form IV of the present invention is low-hygroscopicity form and it does not convert to any other forms of Cabazitaxel in various relative humidly (RH) conditions, such as normal atmospheric humidy, 60%, 80% and 100% RH and at a temperature of about room temperature.

In one embodiment the present invention encompasses crystalline Cabazitaxel designated as form V. Form V can be characterized by data selected from: a solid state $^{13}$C NMR spectrum with peaks at 135.5, 70.4, 25.7 and 10.6 ppm±0.2 ppm; by a solid state $^{13}$C NMR spectrum having chemical shift differences between said characteristic peaks at 135.5, 70.4, 25.7 and 10.6 ppm±0.2 ppm and a reference peak at 125.1±0.2 ppm of 10.4, −54.7, −99.4 and −114.5 ppm±0.1 ppm, respectively; by a solid state $^{13}$C NMR pattern substantially as depicted in any one of FIGS. 33-35; and by combinations thereof.

Form V, as characterized above, can be further characterized by data selected from; a solid state $^{13}$C NMR spectrum with peaks at 173.7, 166.2, 79.5 and 73.6 ppm±0.2 ppm; a solid state $^{13}$C NMR spectrum having chemical shift differences between said characteristic peaks at 173.7, 166.2, 79.5 and 73.6 ppm±0.2 ppm and a reference peak at 125.1±0.2 ppm of 48.6, 41.1, −45.6 and −51.5 ppm±0.1 ppm, respectively; and by combinations thereof.

The above form V can be a 1-propanol solvate.

Form V 1-propanol solvate can be characterized by data selected from: a powder X-ray diffraction pattern having peaks at 7.8, 9.0, 10.2, 15.1 and 15.3 degrees two theta±0.1 degrees two theta and optionally having no peak in the area from 10.5 to 12.1 degrees two theta; a powder X-ray diffraction pattern substantially as depicted in FIG. 15; a powder X-ray diffraction pattern substantially as depicted in FIG. 12; a solid state $^{13}$C NMR as described above; and combinations thereof.

Form V 1-propanol solvate, as characterized above, can be further characterized by data selected from: an X-ray powder diffraction pattern having peaks at 7.8, 9.0, 10.2, 15.1 and 15.3 degrees two theta±0.1 degrees two theta and optionally having no peak in the area from 10.5 to 12.1 degrees two theta; and also having additional one, two, three, four or five peaks selected from 7.4, 12.9, 13.3, 13.6 and 18.2 degrees 2-theta±0.1 degrees 2-theta; by a solid state $^{13}$C NMR spectrum with peaks at 173.7, 166.2, 79.5 and 73.6 ppm±0.2 ppm; by a solid state $^{13}$C NMR spectrum having chemical shift differences between said characteristic peaks at 173.7, 166.2, 79.5 and 73.6 ppm±0.2 ppm and a reference peak at 125.1±0.2 ppm of 48.6, 41.1, −45.6 and −51.5 ppm±0.1 ppm, respectively; a DSC thermogram substantially as depicted in FIG. 16; DSC melting peak at about 167° C.±4° C., or 166.6° C. and DSC melting onset at about 156° C.±4° C., or 156.0° C.; a TGA thermogram substantially as depicted in FIG. 17; a residual 1-propanol content of 6.4% 1.5% w/w, preferably about 6.4%, w/w as determined by GC; and combinations thereof. The theoretical content of 1-propanol for a monosolvate of cabazitaxel is about 6.7% w/w.

Alternatively, Form V 1-propanol solvate can be characterized by a powder X-ray diffraction pattern having peaks at 7.4, 7.8, 9.0, 10.2, 10.3, 12.6, 12.9, 13.3, 13.6, 14.4, 14.8, 15.1, 15.3, 15.7, 16.5, 17.0, 17.2, 17.7, 18.0, 18.3, 18.8, 19.5, 19.7, 20.5, 21.1, 21.4, 21.8, 22.9, 23.0, 23.5, 24.0, 24.6, 24.7, 25.2, 25.4, 25.8, 26.4, 26.9, 27.4, 27.9, 28.4, 28.8, 29.6, 30.2, 30.5, 30.9, 31.2, 31.6, 32.1, 32.2, 33.1, 33.7, 34.3, 34.9, 35.3, 35.8, 36.3, 36.8, 37.4, 37.9 and 39.0 degrees two theta±0.1 degrees 2-theta and having no peak in the area from 10.5 to 12.1 degrees two theta.

Form V 1-propanol solvate can be characterized by any combination of the above data.

The above V has advantageous properties including at least one of: chemical purity, flowability, solubility, morphology or crystal habit, stability—such as storage stability, stability to dehydration, stability to polymorphic conversion, low hygroscopicity, low content of residual solvents. Particularly, the crystalline Cabazitaxel Form V of the present invention is low-hygroscopicity form and it does not convert to any other forms of Cabazitaxel in various relative humidly (RH) conditions, such as normal atmospheric humidy, 60%, 80% and 100% RH and at a temperature of about room temperature.

The above solid state forms can be used to prepare other solid state forms of Cabazitaxel and Cabazitaxel salts and solid state forms thereof.

The above solid state forms can be used to prepare pharmaceutical compositions.

The present invention further encompasses 1) a pharmaceutical composition comprising one or more of the solid state forms, as described above, and at least one pharmaceutically acceptable excipient; 2) the use of one or more of the above-described solid state forms, in the manufacture of a pharmaceutical composition, and 3) a method of treating prostate cancer, e.g., hormone refractory prostate cancer. The pharmaceutical composition can be useful for preparing a medicament. The present invention also provides crystalline forms as described above for use as a medicament.

The present invention also describes novel intermediates for the synthesis of Cabazitaxel, and processes for preparing the novel intermediates, and for preparing Cabazitaxel via those intermediates. The process described in the present invention avoids the direct methylation of the hydroxyl groups in positions 7 and 10 of the baccatine derivative of the following formula:

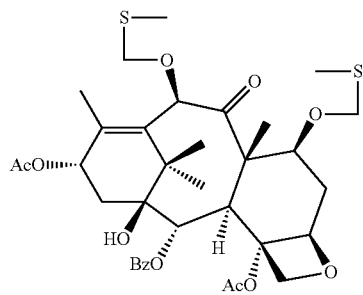

Direct methylation of the above compound by common methylating agents is usually done while using strong bases (for example, as described in U.S. Pat. No. 5,847,170, U.S. Pat. No. 5,962,705). The use of these strong bases is undesirable and leads to decomposition of the product. The present invention provides a process wherein all the reaction steps can be done under mild conditions and the product is obtained in good yield.

The present invention provides 13-acetyl-7,10-methylthiomethyl-10-DAB, referred to herein as Compound 3, of the following formula:

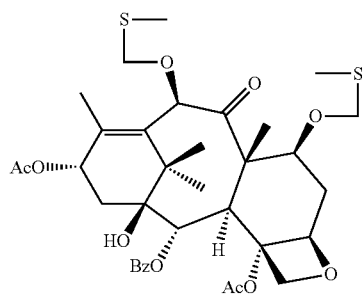

and 7,10-methylthiomethyl-10-DAB, referred to herein as Compound 4, of the following formula:

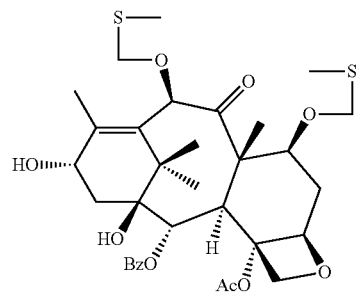

Compound 3 can be prepared by acetylation of 10-DAB, referred to herein as 10-DAB, of the following formula:

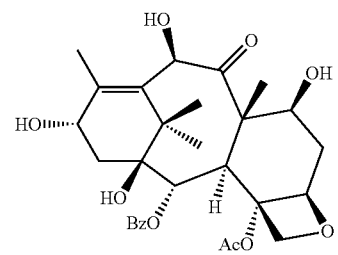

on positions 7, 10 and 13, followed by selective de-acetylation of positions 7 and 10 and then methylthiomethylation of those positions, to obtain compound 3. Compound 4 can be obtained by de-acetylation of position 13 of compound 3. Compound 4 can then be subjected to desulphurization with RaNi to produce Compound 5. Alternatively, the desulphurization/methylation on positions 7 and 10 can be done on Compound 3 (prior to the de-acetylation of position 13), thus leading to compound 6, and Compound 6 can subsequently be de-acetylated to provide compound 5.

The above described process can be illustrated by the following scheme:

Scheme 1:

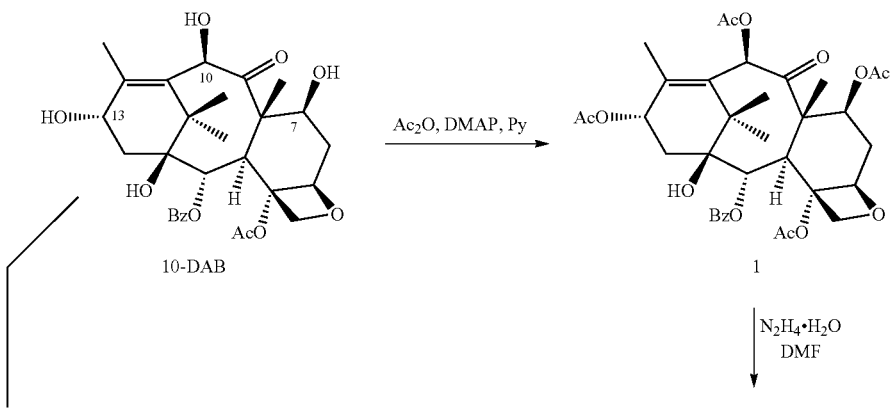

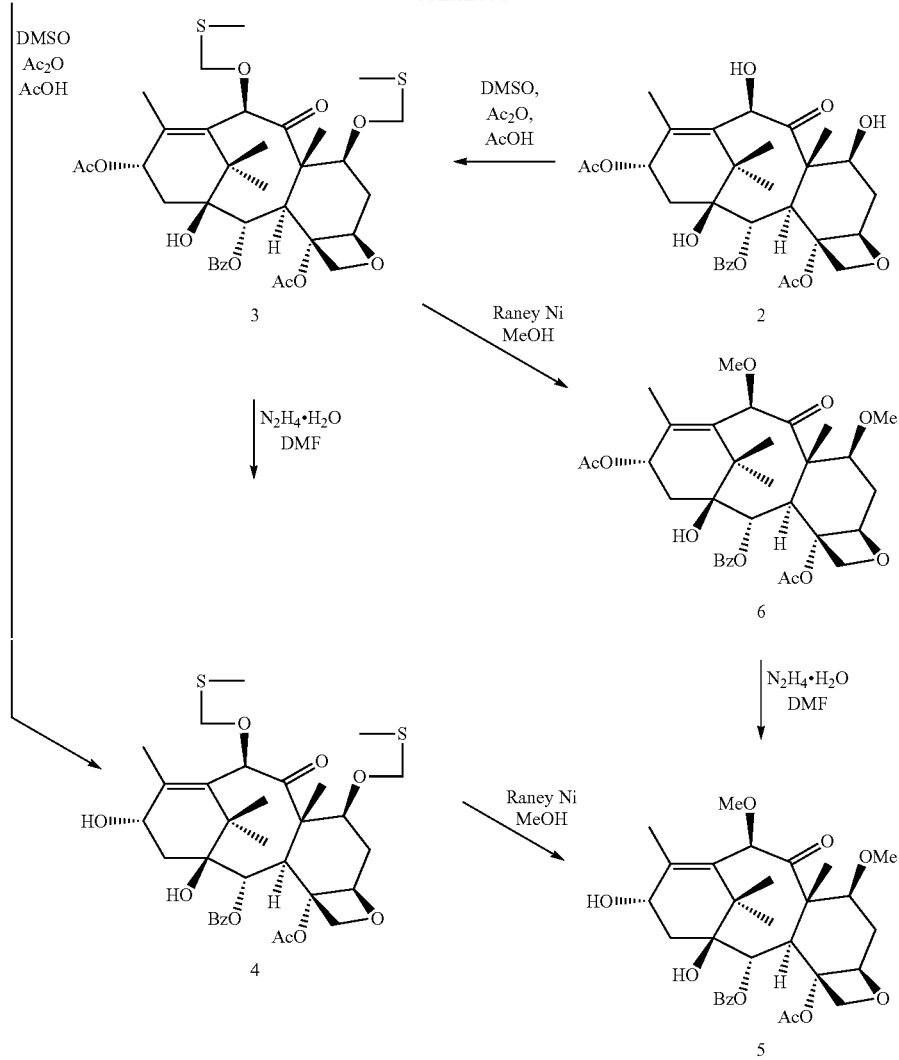

Compound 5 can be converted to Cabazitaxel, for example, according to a process described in U.S. Pat. No. 5,847,170.

The present invention also provides an alternative process for preparation of Cabazitaxel, using a novel intermediate, referred to herein as Compound 8, or formula 8, or protected Cabazitaxel (8):

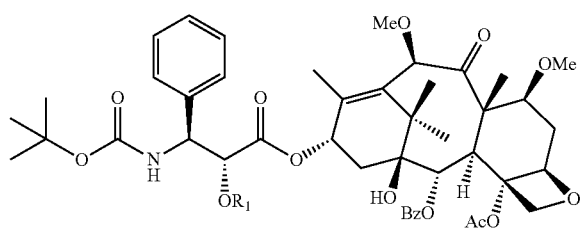

wherein $R_1$ is ethoxyethyl or triethylsilyl.

When $R_1$ is ethoxyethyl, the compound is ((αR,βS)-α-(1-ethoxyethoxy)-β-[[(1,1-dimethylethoxy) carbonyl]amino] benzenepropanoic acid (2aR,4S,4aS,6R,9S,11S,12S,12aR, 12bS)-12b-(acetyloxy)-12-(benzoyloxy)-2a,3,4,4a,5,6,9,10, 11,12,12a,12b-dodecahydro-11-hydroxy-4,6-dimethoxy-4-a,8,13,13-tetramethyl-5-oxo-7,11-methano-1H-cyclodeca [3,4]benz[1,2-b]oxet-9-yl ester), referred to herein as Compound 8a, formula 8a or protected Cabazitaxel (8a).

When $R_1$ is triethylsilyl, the compound is ((αR,βS)-α-triethylsilyloxy-β-[[(1,1-dimethylethoxy)carbonyl]amino] benzenepropanoic acid (2aR,4S,4aS,6R,9S,11S,12S,12aR, 12bS)-12b-(acetyloxy)-12-(benzoyloxy)-2a,3,4,4a,5,6,9,10, 11,12,12a,12b-dodecahydro-11-hydroxy-4,6-dimethoxy-4-a,8,13,13-tetramethyl-5-oxo-7,11-methano-1H-cyclodeca [3,4]benz[1,2-b]oxet-9-yl ester), referred to herein as Compound 8b, formula 8b or protected Cabazitaxel (8b).

The process comprises reacting 2aR,4S,4aS,6R,9S,11S, 12S,12aR,12b5)-12b-acetyloxy-12-benzoyloxy-9,11-dihydroxy-4,6-dimethoxy-1,2a,3,4,4a,6,9,10,11,12,12a,12b-dodecahydro-4-a,8,13,13-tetramethyl-7,11-methano-5H-cyclodeca(3,4)benz(1,2-b)oxet-5-one (referred to herein as 7,10-dimethoxy-10-DAB, or compound 5, or simply 5) of the following formula:

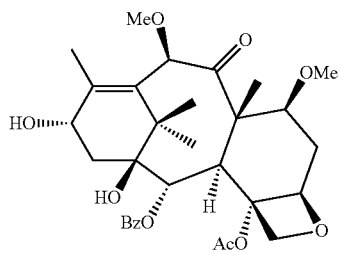

7,10-dimethoxy-10-DAB (5)

acterized by data selected from: a powder X-ray diffraction pattern having peaks at 9.4, 9.9, 10.5, 13.5 and 20.3 degrees two theta±0.2 degrees two theta; a powder X-ray diffraction pattern substantially as depicted in FIG. 5; and by combinations thereof. Crystalline 7,10-dimethoxy-10-DAB can be further characterized by a powder X-ray diffraction pattern having peaks at 9.4, 9.9, 10.5, 13.5 and 20.3, and also having additional one, two, three, four or five peaks selected from 10.9, 16.0, 16.4, 17.6 and 21.3 degrees two theta±0.2 degrees two theta.

The above described process can be illustrated by the following scheme 2:

Scheme 2:

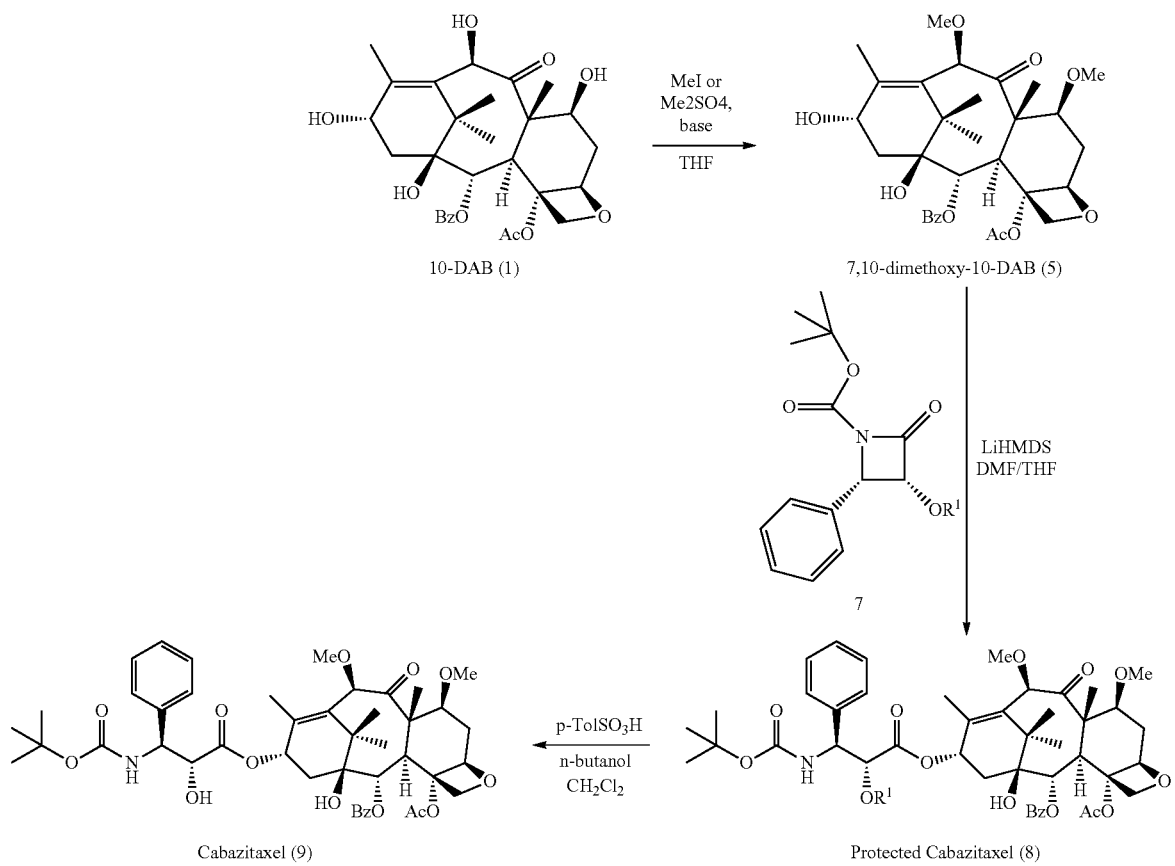

and a protected beta lactam of the following formula:

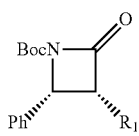

wherein $R_1$ is ethoxyethyl or triethylsilyl; to obtain the compound of formula 8, and de-protecting the compound of formula 8, to obtain Cabazitaxel.

7,10-Dimethoxy-10-DAB (compound 5) can be in a crystalline form. Crystalline 7,10-dimethyl-10-DAB can be charwherein $R^1$ is ethoxyethyl or triethylsilyl When $R^1$ is ethoxyethyl, EE-Cabazitaxel is obtained as the protected Cabazitaxel compound 8.

When $R^1$ is triethylsilyl, TES-Cabazitaxel is obtained as the protected Cabazitaxel compound 8.

TES-Cabazitaxel can be obtained in a crystalline form. Crystalline TES-Cabazitaxel can be characterized by data selected from: a powder X-ray diffraction pattern having peaks at 7.0, 7.3, 9.2, 10.6 and 14.0 degrees two theta±0.1 degrees two theta; a powder X-ray diffraction pattern substantially as depicted in FIG. 36; and combinations thereof. Crystalline TES—Cabazitaxel, as characterized above, can be further characterized by a powder X-ray diffraction pattern having peaks at 7.0, 7.3, 9.2, 10.6 and 14.0, and also having additional one, two, three, four or five peaks selected from 8.0, 11.9, 18.6, 18.9 and 21.0 degrees two theta±0.1 degrees two theta.

The reaction of 7,10-dimethoxy-10-DAB (5) and the protected beta lactam can be done in the presence of base, such as an amide base, like lithium bis(trimethylsilyl)-amide or an alkyl lithium, like butyl lithium, and a solvent, such as a polar aprotic solvent. For example, the reaction can be done in the presence of dimethylformamide ("DMF") or tetrahydrofuran ("THF") or mixtures thereof.

The above reaction is performed at a suitable temperature, for example from about 0° C. to about 30° C., or at about room temperature; for a suitable period of time, such as from about 30 min to about 10 h.

The de-protection of the compound of formula 8 can be done by acidic hydrolysis of the $R_1$ protecting group. Suitable acids include strong acids such as aryl or alkyl sulfonic acids, e.g., methane sulfonic acid, and p-toluenesulfonic acid. This step can be performed in the presence of a suitable solvent. Suitable solvents for this reaction include alcohols (e.g., $C_{1-4}$ alcohols and polar aprotic solvents (e.g., DMF, DMSO, THF) and mixtures thereof. For example the de-protection can be done in the presence of n-butanol, or a mixture of methanol and THF.

The above de-protection step is performed at a suitable temperature such as from about 0° C. to about 30° C. For example, it can be done at about room temperature. The reaction is carried out for a suitable period of time, such as from about 30 min to about 10 h.

The obtained Cabazitaxel can be recovered, for example by a process comprising filtering, washing and drying. The obtained product can be further purified, for example by recrystallization.

The starting 7,10-dimethyl-10-DAB (5) can be prepared according to the process described above and illustrated in scheme 1. Alternatively, the starting 10-dimethyl-10-DAB (5) can be prepared by direct methylation of 10-DAB of the following formula:

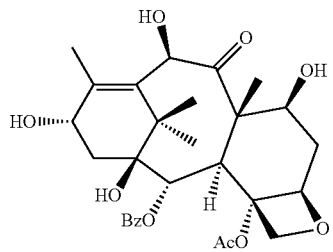

in the presence of an alkali hydroxide base, for example potassium or sodium hydroxide (or a mixture thereof) or in a mixture of one or both of these bases with potassium carbonate or sodium carbonate.

The methylating agent can be, for example, dimethyl sulfate or methyl iodide.

The methylation may be done in the presence of suitable solvent. Suitable solvents for this reaction include, for example, polar aprotic solvents such as THF and DMF. For example the reaction can be done in the presence of dimethylformamide ("DMF"), tetrahydrofuran ("THF") or a mixture thereof.

The above reaction is performed at a suitable temperature such as from about 0° C. to about 50° C. For example it can be done at about room temperature. The reaction is carried out for a suitable period of time, such as from about 1 h to about 48 h.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Powder X-Ray Diffraction (PXRD) Method

Powder X-ray Diffraction was performed on an X-Ray powder diffractometer: PanAlytical X' pert Pro; CuKα radiation (λ=1.5418 Å); X'Celerator detector with active length 2.122 degrees 2-theta; laboratory temperature 22-25° C.; zero background sample holders. Prior to analysis, the samples were gently ground using a mortar and pestle to obtain a fine powder. The ground sample was adjusted into a cavity of the sample holder and the surface of the sample was smoothed using a cover glass.

A silicon powder internal standard was used to calibrate the peak positions and to eliminate an effect of the sample preparation. The internal standard possesses a diffraction pattern with defined position at 28.44 degrees 2-theta. The internal standard powder can be mixed with a sample The PXRD diffractogram is then acquired and the current position of the aforementioned internal standard diffraction peak is determined. The difference between the current position of the diffraction and its nominal value of 28.44 degrees 2-theta is calculated. The current positions of all relevant sample peaks are then corrected using the above difference to obtain the true positions of the sample diffractions. The confidence interval for the peak positions was determined to be ±0.1 degrees 2-theta.

Measurement Parameters:
Scan range: 3-40 degrees 2-theta;
Scan mode: continuous;
Step size: 0.0167 degrees;
Time per step: 42 s;
Sample spin: 16 rpm;
Sample holder: zero background silicon plate.

Differential Scanning Calorimetry (DSC) Method

DSC measurements were performed on a Differential Scanning calorimeter DSC823e (Mettler Toledo). Aluminum crucibles 40 μl with pin-holed lids were used for sample preparation. Typical sample weight was between 1 and 5 mg. Program parameters: temperature range at least 30-250° C.; heating rate 10° C./min; nitrogen flow 50 ml/min.

Thermogravimetric Analysis (TGA) Method

TGA measurements were performed on a Thermogravimetric analyzer TGA851e (Mettler Toledo). Alumina crucibles 70 μl were used for sample preparation. Usual weight of sample was between 7 and 13 mg.

Program parameters: temperature range at least 30-250° C.; heating rate 10° C./min; nitrogen flow 50° C./min.

Gas Chromatography (GC) Method

Residual solvents were determined by gas chromatography using head-space sampling. Head-space instrument HP7694 coupled with gas chromatograph A6890 equipped with FID detector (Agilent technologies) were used for the analyses.

$^{13}$C Solid State NMR

Solid-state $^{13}$C NMR spectra were recorded with variable amplitude cross polarization, magic angle spinning and high power proton decoupling using a BRUKER Avance II+ spectrometer operating at 125 MHz and ambient temperature (about 25° C.—not controlled). A probe using 4 mm o d zirconia rotors was employed. The operation conditions were: contact time: 2 ms; acquisition time, recycle delay: 2s, 2048 scans; spin rate: 11 kHz. Chemical shifts were referenced via a replacement sample of glycine (carboxyl carbon chemical shift assigned as 176.03 ppm relative to the signal of tetramethylsilane).

Single Crystal Analysis

Data was collected on Xcalibur PX, Cu $K_\alpha$ using combined $\phi$ and $\omega$ scans, data collection runs were optimized for absolute configuration analysis. Positional and anisotropical thermal parameters of all non-hydrogen atoms were refined.

Hygroscopicity Test Procedure:

About 100 mg of a sample was placed to a cell with controlled relative humidity. The samples were exposed to 60%, 80% and 100% relative humidity, at a temperature of about room temperature, for a period of about two days. XRPD analysis and water content by Karl-Fischer coulometric titration were carried out before and after the exposure to the defined relative humidity.

Karl-Fischer Coulometric titration:

Water was determined by KF Oven method (832 KF Thermoprep connected to 831 KF Coulometer). Water from the sample (50 mg of cabazitaxel) was released by nitrogen stream at 130° C. Extraction time was 10 minutes.

EXAMPLES

Example 1

Preparation of 7,10-dimethoxy-10-DAB

10-DAB (100 g, 0.184 mol) was suspended in THF (500 ml) with dimethyl sulfate (57.9 g, 0.46 mol) was added. Sodium hydride (60% dispersion in oil, 22.8 g, 0.57 mol) was added portionwise. The suspension was heated to 45° C. while stirring. After the reaction was complete (HPLC monitoring), the mixture was cooled to 10° C., and HCl (500 ml of 2% sol.) was added into the cooled mixture, forming an off-white suspension. The suspension was cooled to below 10° C. and vacuum filtered through a filter funnel. The white product was washed with water (2×175 ml) and THF (2×100 ml) and dried in a vacuum oven at 45° C. to give 63.54 g (0.111 mol, 60%) of a white product (HPLC purity 87%). Recrystallization from hot DMF improved the purity to above 96% (50.41 g).

Example 2

Preparation of 7,10-dimethoxy-10-DAB

10-DAB (1 g, 1.84 mmol) was suspended in THF (5 ml) and dimethyl sulfate (0.53 g, 4.22 mmol) was added. The resulting white suspension was heated to 45° C. while stirring. After reaching 45° C., potassium carbonate (0.15 g, 0.6 mmol) was added followed by sodium hydroxide (0.29 g, 4 mmol) in the form of pearls. The resulting suspension was stirred at 45° C. for 2 h and then was vacuum filtered through a filter funnel. The resulting white product was washed with water (2×) and THF (2×) and dried in a stream of air to give 0.37 g (35%) of white crystals Example 3

Preparation of Cabazitaxel Via Ethoxyethyl-Cabazitaxel

A solution of lithium bis(trimethylsilyl)amide ("LH-MDS", 1 M/THF, ethylbenzene, 7 ml, 7 mmol) was added dropwise over 5 min to a stirred suspension of 7,10-dimethoxy-10-DAB (11.45 g, 20 mmol) and ethoxyethyl ("EE")-beta lactam (8.72 g, 26 mmol) in DMF (30 ml) and THF (30 ml) at room temperature under nitrogen. The reaction mixture was stirred at room temperature for 1 h. Acetic acid (4 M solution in water, 3.5 ml, 14 mmol) was added and the reaction was stirred for 5 min. The reaction mixture was then partitioned between MTBE (200 ml) and water (150 ml). The organic layer was separated, extracted with water (3×100 ml) and filtered through $MgSO_4$. n-BuOH (50 ml) was added to the MTBE filtrate and the mixture was concentrated under reduced pressure at 30° C. p-Toluene sulfonic acid (571 mg, 3 mmol) and n-BuOH (130 ml) were added to the concentrate, and the mixture was stirred at 50° C. for 1 h. The reaction mixture was cooled to room temperature, seeded with n-BuOH solvate of Cabazitaxel and stirred overnight. The product was filtered off, washed with n-BuOH and hexane and dried to give Cabazitaxel (11.8 g, 65%).

Example 4

Preparation of Cabazitaxel via triethylsilyl-Cabazitaxel

A solution of LHMDS (1 M/THF, ethylbenzene, 7 ml, 7 mmol) was added dropwise over 5 min to a stirred suspension of 7,10-dimethoxy-10-DAB (11.45 g, 20 mmol) and triethylsilyl ("TES")-beta lactam (11.3 g, 30 mmol) in DMF (26 ml) and THF (34 ml) at room temperature under nitrogen. The reaction mixture was stirred at room temperature for 1.5 h. The reaction mixture was then partitioned between MTBE (200 ml) and 5% aqueous citric acid (104 ml). The organic layer was separated and extracted with water (3×100 ml). The organic layer was then evaporated to a small volume under reduced pressure at 50° C. Fresh MTBE (50 ml) was added to the concentrate and the mixture was evaporated again. The addition of MTBE and its evaporation was repeated two more times to remove residual water. MTBE (10 ml) was added to the resulting syrup so that the overall estimated volume of MTBE was 30 ml and the mixture was heated to 60° C. Hot n-heptane (60° C., 60 ml) was added, and the mixture was stirred at 60° C. for 5 min and then allowed to cool to 15-20° C. The cooled mixture was stirred at 15-20° C. for 2 h. The product was then filtered off, washed with a mixture of MTBE/heptane 1:2 (2×), and dried to give TES-Cabazitaxel (15.4 g, 80%). A solution of p-toluenesulfonic acid (114 mg, 0.6 mmol) in MeOH (2 ml) was added to a solution of TES-Cabazitaxel (1.90 g, 2 mmol) in THF (4 ml) and MeOH (4 ml) at 0-5° C. The reaction mixture was stirred at 0-5° C. for 1 h. The reaction was then neutralized by adding a solution of TEA/toluene (1 M, 0.63 ml). The mixture was then warmed to room temperature. Toluene (5 ml) was added and the mixture was stirred under vacuum for 1 h. Another portion of toluene (5 ml) was added and the stirring under vacuum was continued, first at room temperature and after 30 min at 30° C. The mixture was then allowed to cool to room temperature over 1 h and stirred at room temperature for an additional 30 min. The product was filtered off, washed with toluene (2×) and dried to give Cabazitaxel (1.65 g, 90%).

Example 5

General Procedure for the Preparation of Crude Cabazitaxel

A solution of lithium bis(trimethylsilyl)amide (LHMDS, 23% in THF, 8.73 g, 12 mmol) was added to a stirred suspension of 7,10-dimethoxy-10-DAB (5.73 g, 10 mmol) and N-Boc-O-EE-beta-lactam (4.02 g, 12 mmol) in dry THF (30 ml) at room temperature over 20 min. When the reaction was complete (about 3 h), formic acid (20 ml) was added and the resulting mixture was stirred for 20 h. The reaction mixture was then partitioned between methyl-tert-butyl ether (MTBE) (80 ml) and water (100 ml). The separated organic phase was extracted with water (2×50 ml), separated, and concentrated to provide a syrup.

Example 6

Preparation of Cabazitaxel Form I

Cabazitaxel (8 g) was dissolved in a mixture containing 10% MTBE in toluene (150 ml) and slowly concentrated under slightly reduced pressure at 45-50° C. When the product started to precipitate, the vacuum was disconnected, and the mixture was stirred at 45-50° C. for 1 h, then cooled to 22° C., and stirred for 3 h and then filtered. The collected product was washed twice with toluene and dried on the filter.

Solid state NMR peaks: 173.50, 171.23, 166.98, 156.23, 140.08, 139.25, 138.67, 136.35, 135.31, 131.05, 130.18, 129.37, 126.17, 85.63, 84.38, 82.95, 82.10, 80.73, 75.98, 74.82, 71.79, 59.05, 57.37, 55.38, 50.16, 44.21, 35.51, 30.86, 28.72, 22.85, 21.42, 16.47, and 12.58 ppm 0.2 ppm.

Example 7

Preparation of Cabazitaxel Amorphous

Crude cabazitaxel (a syrup, as prepared in Example 5) was dissolved in a small amount of 5% MTBE in toluene and purified by column chromatography (silica gel, 5-25% MTBE gradient in toluene). All of the desired fractions were combined and concentrated and the resulting residue was dissolved in toluene at 60° C. Heptane (an equal amount relative to the toluene) was added and the resulting solution was cooled to 40° C. The product started to precipitate. This mixture was stirred at 40° C. for 2 hours and then stirred overnight at 22° C. The product was then filtered, washed with heptane (2×) and dried on the filter.

Solid state NMR peaks: 170.31, 166.74, 155.18, 137.81, 128.29, 81.09, 75.67, 56.9, 47.62, 43.4, 35.75, 31.91, 28.13, 22.43, 13.91, and 10.14 ppm±0.2 ppm.

Example 8

Preparation of Cabazitaxel Amorphous

Crude cabazitaxel (a syrup, as prepared in Example 5) was mixed with water (150 ml) and hexane (150 ml) and stirred for 24 h at room temperature. The product was then filtered, washed with water and dried on the filter. Yield: 10.0 g

Example 9

Preparation of 7,10,13-triacetyl-10-DAB (Compound 1)

Acetic anhydride (43.8 ml, 462 mmol) was added over 10 minutes to a stirred solution of 10-DAB (32.7 g, 60 mmol) and DMAP (733 mg, 6 mmol) in pyridine (120 ml) under nitrogen. The resulting reaction mixture was stirred at 23° C. for 20 h. The reaction mixture was then partitioned between ethyl acetate and water. The organic phase was separated and washed with water (3×) and then concentrated to dryness. Heptane was added to the residue, and this mixture was stirred for 30 min and then filtered. The resulting crude product was washed with heptane and dried (38.6 g, 96%).

Example 10

Preparation of 13-acetyl-10-DAB (Compound 2)

Hydrazine hydrate (8.35 ml, 172 mmol) was added to a stirred solution of 7,10,13-triacetyl-10-DAB (1) (36 g, 53.7 mmol) in DMF (65 mmol) under nitrogen at 0° C. The resulting reaction mixture was allowed to stand at 0° C. for 20 h. The reaction mixture was then admixed to a stirred mixture of MTBE and water and vigorously stirred for 1 h. The product was recovered from this reaction mixture by filtration, and was then washed with water (3×) and dried. The dry product was washed with MTBE (3×) and dried (26.8 g, 85%).

Example 11

Preparation of 13-acetyl-7,10-methylthiomethyl-10-DAB (Compound 3)

A mixture of acetic anhydride (75.5 ml, 0.8 mol) and acetic acid (23.0 ml, 0.4 mol) was added to a stirred solution of 13-acetyl-10-DAB 2 (14.7 g, 25 mmol) in DMSO (100 ml) under nitrogen. The resulting reaction mixture was stirred for 5 days at 23° C. The reaction mixture was then admixed with a stirred mixture containing ethyl acetate (1 l), water (2 l) and NaHCO$_3$ (202 g, 2.4 mol) and this mixture was stirred for 1 h. The organic phase was separated, washed with water (3×), and concentrated. The product was precipitated by adding ethanol. The resulting suspension was stirred for 2 h in an ice bath, and the product was then filtered, washed with ethanol and dried.

Example 12

Preparation of 7,10-methylthiomethyl-10-DAB (Compound 4)

Hydrazine hydrate (2.90 ml, 60 mmol) was added to a stirred solution of 13-acetyl-7,10-methylthiomethyl-10-DAB (3) (4.24 g, 6 mmol) in DMF (10 ml) under nitrogen. The resulting reaction mixture was stirred at 23° C. for 18 h. The reaction mixture was partitioned between MTBE and 5% NaCl. The organic phase was separated, washed with water (3×), and concentrated to dryness.

Example 13

Preparation of 7,10-methylthiomethyl-10-DAB (Compound 4)

A mixture of acetic anhydride (15.1 ml, 160 mmol) and acetic acid (4.6 ml, 80 mmol) was added to a stirred suspension of 10-DAB (2.72 g, 5 mmol) in DMSO (20 ml) under nitrogen. The resulting reaction mixture was stirred for 5 days at 23° C., and then partitioned between ethyl acetate and saturated NaHCO$_3$. The organic phase was extracted with water (2×), separated, and concentrated to dryness. The product was purified by column chromatography (10-15% THF/EtOAc).

Example 14

Preparation of 13-acetyl-7,10-dimethoxy-10-DAB (Compound 6)

Raney Nickel (slurry in water, 100 g) was added to a suspension of 13-acetyl-7,10-methylthiomethyl-10-DAB (3) (3.53 g, 5 mmol) in methanol (150 ml) and the mixture was stirred at 23° C. overnight. The methanol was evaporated under reduced pressure. THF (150 ml) was added, and the resulting mixture was stirred for 20 min and then filtered through diatomaceous earth (Celite), and the filtrate was concentrated to a small volume. The product was then precipitated by adding methanol, and the precipitate was filtered, washed with methanol and dried (1.48 g, 48%).

Example 15

Preparation of 7,10-dimethoxy-10-DAB (Compound 5)

Raney Nickel (slurry in water, 20 g) was added to a solution of 7,10-methylthiomethyl-10-DAB (4) (665 mg, 1 mmol) in methanol (30 ml) and the mixture was stirred at 23° C. overnight. The methanol was evaporated under reduced pressure. THF (50 ml) was added and the mixture was stirred for 20 min and filtered through Celite, and then the filtrate was concentrated to small volume. The product was precipitated by adding methanol, and precipitate was then filtered, washed with methanol and dried (350 mg, 61%).

Example 16

Preparation of 7,10-dimethoxy-10-DAB (Compound 5)

Hydrazine hydrate (0.97 ml, 20 mmol) was added to a stirred mixture of 13-acetyl-7,10-dimethoxy-10-DAB (6) (1.23 g, 2 mmol) in DMF (3.3 ml) under nitrogen, and the resulting reaction mixture was stirred at 23° C. for 18 h. The reaction mixture was then partitioned between EtOAc and water. The organic phase was extracted with water (2×), and concentrated under reduced pressure and the product was precipitated by adding methanol. The precipitated product was filtered, washed with methanol and dried (607 mg, 53%).

Example 17

Preparation of Cabazitaxel Form II

Crude Cabazitaxel (Prepared according to example 5) was evaporated and dissolved in ethanol ("EtOH"). The solution was evaporated, the residue dissolved in EtOH, the solution evaporated again, the residue dissolved in EtOH, and then this solution was evaporated to dryness. The residue was dissolved in MTBE and evaporated to dryness, then dissolved in MTBE again, warmed to 50° C. and concentrated under slightly reduced pressure. After evaporation of about one third of the volume, a pale solid material started to precipitate. The vacuum was disconnected and the mixture was allowed to cool to room temperature and was maintained for 60 hours. The product was filtered, washed with MTBE and dried on filter.

Solid state $^{13}$C NMR peaks: 174.29, 170.77, 166.47, 155.69, 138.63, 137.73, 135.88, 134.13, 129.61, 127.97, 125.12, 85.27, 83.37, 81.87, 79.68, 78.86, 75.65, 74.13, 72.05, 71.39, 57.52, 56.62, 54.36, 48.91, 43.24, 34.34, 29.83, 28.93, 28.01, 27.35, 22.06, 20.08, 15.85 and 11.43 ppm±0.2 ppm.

Example 18

Preparation of Cabazitaxel Form III

Cabazitaxel (toluene solvate form I, 1.2 g) was dissolved in isopropanol ("i-PrOH") (20 ml) at reflux, and the solution was then allowed to cool. The product started to precipitate at 35-40° C. The mixture was cooled to 22° C. and was maintained for 20 h. The product was then separated by filtering, washed with i-PrOH and dried on filter.

Solid state $^{13}$C NMR peaks: 173.51, 171.14, 166.09, 155.63, 139.84, 138.27, 135.20, 133.59, 129.31, 127.84, 125.08, 85.68, 83.52, 82.53, 82.11, 79.53, 79.06, 75.99, 73.79, 73.5, 70.18, 63.39, 57.80, 57.19, 56.4, 53.72, 48.83, 42.92, 34.30, 29.13, 28.57, 27.93, 25.44, 23.53, 22.12, 20.23, 15.44 and 11.54 ppm±0.2 ppm.

Example 19

Preparation of Cabazitaxel form IV

Cabazitaxel (toluene solvate form I, 1.2 g) was dissolved in n-butanol ("n-BuOH") (20 ml) at reflux and the solution was allowed to cool. The product started to precipitate at 50° C. The mixture was cooled to 22° C. and stirred for 20 h. The product was then separated by filtering, washed with n-BuOH and dried on the filter.

Solid state $^{13}$C NMR peaks: 173.27, 171.14, 165.98, 155.47, 139.52, 138.26, 135.30, 133.94, 129.56, 128.41, 125.22, 85.60, 83.53, 82.38, 81.96, 79.78, 79.31, 76.01, 74.5, 73.59, 70.21, 60.55, 57.94, 57.30, 56.43, 53.95, 49.14, 43.06, 34.50, 29.33, 28.16, 27.66, 21.87, 20.3, 19.03, 15.80, 13.63 and 11.59 ppm±0.2 ppm.

Example 20

Preparation of Cabazitaxel Form V

Cabazitaxel (form I, toluene solvate, 1 g) was dissolved in 1-propanol (15 ml) at reflux and the solution was allowed to cool to room temperature. The product started to precipitate after 2 hrs of stirring at 22° C. The mixture was stirred for 3 more hours at 22° C. The product was then separated by filtering, washed with 1-propanol and dried on the filter.

Example 21

Preparation of Cabazitaxel Amorphous

Cabazitaxel (268 mg) was dissolved in THF (1 ml) and the solution was slowly added to vigorously stirred n-heptane 50 ml) at 20° C. The resulting suspension was stirred for additional 10 minutes, and the solid matter was recovered by filtration, washed with petrolether (10 ml), and dried in nitrogen stream.

Example 22

Preparation of Cabazitaxel Form III (Isopropanol Solvate) for Single Crystal Analysis Cabazitaxel (180 mg) was dissolved in isopropanol (18 ml) by heating to 50° C. for 5 min. The solution was allowed to cool to 20° C. and crystallized at 20° C. for 24 hours. A single crystal of cabazitaxel isopropanol solvate (1:1) was directly mounted on goniometer head for the crystal structure determination.

Example 23

Preparation of Cabazitaxel Amorphous

Cabazitaxel (180 mg, isopropanol solvate form III) was dissolved in 1,3-dimethyl-2-imidazolidinone (0.36 mL) at ambient temperature, and water (0.8 mL) was added over 30 min at 10° C. The resulting suspension was stirred at 10° C. for 2 hours followed by filtration.

TABLE 1

Hygroscopicity and stability test
The hygroscopicity was measured as described above,
and the crystalline structure was determined by PXRD.

| % RH | % water content | Form |
|---|---|---|
| Form I | | |
| Atmospheric | 0.05 | Form I |
| 60 | 0.13 | Form I |
| 80 | 0.14 | Form I |
| 100 | 0.14 | Form I |
| Form II | | |
| Atmospheric | 0.02 | Form II |
| 60 | 0.07 | Form II |
| 80 | 0.09 | Form II |
| 100 | 0.11 | Form II |
| Form III | | |
| Atmospheric | 0.05 | Form III |
| 60 | 0.14 | Form III |
| 80 | 0.23 | Form III |
| 100 | 0.19 | Form III |
| Form IV | | |
| Atmospheric | 0.01 | Form IV |
| 60 | 0.07 | Form IV |
| 80 | 0.09 | Form IV |
| 100 | 0.09 | Form IV |
| Form V | | |
| Atmospheric | 0.08 | Form V |
| 60 | 0.21 | Form V |
| 80 | 0.30 | Form V |
| 100 | 0.68 | Form V |

What is claimed is:

1. Crystalline cabazitaxel, wherein the crystalline cabazitaxel is
    crystalline cabazitaxel designated as form III, characterized by:
        a solid state $^{13}$C NMR spectrum with peaks at 139.8 127.8, 63.4, 25.4 and 23.5 ppm±0.2 ppm;
        a solid state $^{13}$C NMR spectrum having chemical shift differences between said characteristic peaks at 139.8 127.8, 63.4, 25.4 and 23.5 ppm±0.2 ppm and a reference peak at 125.1±0.2 ppm of 14.8, 2.8, −61.7, −99.6 and −101.6 ppm±0.1 ppm, respectively;
        a solid state $^{13}$C NMR spectrum substantially as depicted in any one of FIGS. 27-29; and combinations thereof;
    crystalline cabazitaxel designated as form II, characterized by:
        a solid state $^{13}$C NMR spectrum with peaks at 174.3, 170.8, 166.5, 137.7, and 135.9 ppm±0.2 ppm;
        a solid state $^{13}$C NMR spectrum having chemical shift differences between said characteristic peaks at 174.3, 170.8, 166.5, 137.7, and 135.9 ppm±0.2 ppm and a reference peak at 125.1±0.2 ppm of 49.2, 45.7, 41.4, 12.6 and 10.8 ppm±0.1 ppm, respectively;
        a solid state $^{13}$C NMR spectrum substantially as depicted in any one of FIGS. 24-26; and combinations thereof;
    crystalline cabazitaxel form IV, characterized by:
        a solid state $^{13}$C NMR spectrum with peaks at 128.4, 60.6, 19.0 and 13.6 ppm±0.2 ppm;
        a solid state $^{13}$C NMR spectrum having chemical shift differences between said characteristic peaks at 128.4, 60.6, 19.0 and 13.6 ppm±0.2 ppm and a reference peak at 125.2±0.2 ppm of 3.2, −64.7, −106.2 and −111.6 ppm±0.1 ppm, respectively;
        a solid state $^{13}$C NMR spectrum substantially as depicted in any one of FIGS. 30-32; and combinations thereof; or
    crystalline cabazitaxel form V, characterized by:
        a solid state $^{13}$C NMR spectrum with peaks at 135.5, 70.4, 25.7 and 10.6 ppm±0.2 ppm;
        a solid state $^{13}$C NMR spectrum having chemical shift differences between said characteristic peaks at 135.5, 70.4, 25.7 and 10.6 ppm±0.2 ppm and a reference peak at 125.1±0.2 ppm of 10.4, −54.7, −99.4 and −114.5 ppm±0.1 ppm, respectively;
        a solid state $^{13}$C NMR pattern substantially as depicted in any one of FIGS. 33-35; and combinations thereof.

2. The crystalline cabazitaxel form III of claim 1, further characterized by:
    a solid state $^{13}$C NMR spectrum with peaks at 139.8 127.8, 63.4, 25.4 and 23.5 ppm±0.2 ppm and also at 173.5, 133.6, 129.3 and 15.4 ppm±0.2 ppm;
    a solid state $^{13}$C NMR spectrum having chemical shift differences between said characteristic peaks at 173.5, 133.6, 129.3 and 15.4 and a reference peak at 125.1±0.2 ppm of 48.4, 8.5, 4.2 and −109.6 ppm±0.1 ppm, respectively; and
    combinations thereof.

3. The crystalline cabazitaxel form III of claim 1, wherein the crystalline form is a 2-propanol solvate.

4. The crystalline cabazitaxel form III of claim 2, wherein the crystalline form is a 2-propanol solvate.

5. The crystalline cabazitaxel form II of claim 1, further characterized by:
    a solid state $^{13}$C NMR spectrum with peaks at 174.3, 170.8, 166.5, 137.7, and 135.9 ppm and also at 138.6, 74.1, 72.1 and 71.4 ppm±0.2 ppm;
    a solid state $^{13}$C NMR spectrum having chemical shift differences between said characteristic peaks at 138.6, 74.1, 72.1 and 71.4 ppm±0.2 ppm and a reference peak at 125.1±0.2 ppm of 13.5, −51.0, −53.1 and −53.7 ppm±0.1 ppm, respectively; and combinations thereof.

6. The crystalline cabazitaxel form II of claim 1, wherein the crystalline form is a methyl tert-butyl ether ("MTBE") solvate.

7. The crystalline cabazitaxel form II of claim 5, wherein the crystalline form is a methyl tert-butyl ether ("MTBE") solvate.

8. The crystalline cabazitaxel form IV of claim 1, further characterized by:
    a solid state $^{13}$C NMR spectrum with peaks at 128.4, 60.6, 19.0 and 13.6 ppm and also at 173.3, 139.5, 133.9 and 74.5 ppm±0.2 ppm;
    a solid state $^{13}$C NMR spectrum having chemical shift differences between said characteristic peaks at 173.3, 139.5, 133.9 and 74.5 ppm±0.2 ppm and a reference peak at 125.2±0.2 ppm of 48.1, 14.3, 8.7 and −50.7 ppm±0.1 ppm, respectively; and combinations thereof.

9. The crystalline cabazitaxel form IV of claim 1, wherein the crystalline form is a n-butanol solvate.

10. The crystalline cabazitaxel form IV of claim 8, wherein the crystalline form is a n-butanol solvate.

11. The crystalline cabazitaxel form V of claim 1, further characterized by:
  a solid state $^{13}$C NMR spectrum with peaks at 135.5, 70.4, 25.7 and 10.6 ppm±0.2 ppm and also at 173.7, 166.2, 79.5 and 73.6 ppm±0.2 ppm;
  a solid state $^{13}$C NMR spectrum having chemical shift differences between said characteristic peaks at 173.7, 166.2, 79.5 and 73.6 ppm±0.2 ppm and a reference peak at 125.1±0.2 ppm of 48.6, 41.1, −45.6 and −51.5 ppm±0.1 ppm, respectively; and combinations thereof.

12. The crystalline cabazitaxel form V of claim 1, wherein the crystalline form is a 1-propanol solvate.

13. The crystalline cabazitaxel form V of claim 11, wherein the crystalline form is a 1-propanol solvate.

14. Crystalline cabazitaxel, wherein the crystalline cabazitaxel is
  crystalline cabazitaxel form III 2-propanol solvate, characterized: a powder X-ray diffraction pattern having peaks at 7.4, 9.0, 10.3, 13.3 and 13.6 degrees two theta±0.1 degrees two theta and optionally having no peak in the area from 10.5 to 12.1 degrees two theta;
  crystalline cabazitaxel form II MTBE solvate, characterized by: a powder X-ray diffraction pattern having peaks at 7.4, 7.7, 8.9, 12.1 and 13.2 degrees two theta±0.1 degrees two theta and optionally having no peak in the area from 10.4 to 11.9 degrees two theta;
  crystalline cabazitaxel form IV n-butanol solvate, characterized by: a powder X-ray diffraction pattern having peaks at 7.4, 7.9, 8.8, 12.9 and 13.5 degrees two theta±0.1 degrees two theta and optionally having no peak in the area from 10.4 to 12.2 degrees two theta; or
  crystalline cabazitaxel form V 1-propanol solvate characterized by: a powder X-ray diffraction pattern having peaks at 7.8, 9.0, 10.2, 15.1 and 15.3 degrees two theta±0.1 degrees two theta and optionally having no peak in the area from 10.5 to 12.1 degrees two theta.

15. The crystalline cabazitaxel form III 2-propanol solvate of claim 14, further characterized by:
  an X-ray powder diffraction pattern having peaks at 7.4, 9.0, 10.3, 13.3 and 13.6 degrees two theta±0.1 degrees two theta and optionally having no peak in the area from 10.5 to 12.1 degrees two theta, and also having an additional one, two, three, four or five peaks selected from 7.9, 12.9, 15.2, 15.3 and 19.5 degrees 2-theta±0.1 degrees 2-theta;
  a powder X-ray diffraction pattern substantially as depicted in FIG. 9;
  a solid state $^{13}$C NMR spectrum with peaks at 139.8 127.8, 63.4, 25.4 and 23.5 ppm±0.2 ppm;
  a solid state $^{13}$C NMR spectrum having chemical shift differences between said characteristic peaks at 139.8 127.8, 63.4, 25.4 and 23.5 ppm±0.2 ppm and a reference peak at 125.1±0.2 ppm of 14.8, 2.8, −61.7, −99.6 and −101.6 ppm±0.1 ppm, respectively;
  a solid state $^{13}$C NMR spectrum substantially as depicted in any one of FIGS. 27-29;
  a solid state $^{13}$C NMR spectrum with peaks at 139.8 127.8, 63.4, 25.4 and 23.5 ppm±0.2 ppm and also at 173.5, 133.6, 129.3 and 15.4 ppm±0.2 ppm;
  a solid state $^{13}$C NMR spectrum having chemical shift differences between said characteristic peaks at 173.5, 133.6, 129.3 and 15.4 ppm±0.2 ppm and a reference peak at 125.1±0.2 ppm of 48.4, 8.5, 4.2 and −109.6 ppm±0.1 ppm, respectively;
  a DSC thermogram substantially as depicted in FIG. 10; a DSC melting peak at about 166.0° C.±4° C. or 166.0° C. and a DSC melting onset at about 149±4° C., or 148.8° C.;
  a TGA thermogram substantially as depicted in FIG. 11; a residual 2-propanol content of 7.0%±1.5% w/w, preferably about 7.0% w/w as determined by GC; and
  combinations thereof.

16. The crystalline cabazitaxel form II MTBE solvate of claim 14, further characterized by:
  an X-ray powder diffraction pattern having peaks at 7.4, 7.7, 8.9, 12.1 and 13.2 degrees two theta±0.1 degrees two theta and optionally having no peak in the area from 10.4 to 11.9 degrees two theta, and also having an additional one, two, three, four or five peaks selected from 10.1, 12.6, 12.7, 16.1 and 19.3 degrees 2-theta±0.1 degrees 2-theta;
  a powder X-ray diffraction pattern substantially as depicted in FIG. 6;
  a solid state $^{13}$C NMR spectrum with peaks at 174.3, 170.8, 166.5, 137.7, and 135.9 ppm±0.2 ppm; a solid state $^{13}$C NMR spectrum having chemical shift differences between said characteristic peaks at 174.3, 170.8, 166.5, 137.7, and 135.9 ppm±0.2 and a reference peak at 125.1±0.2 ppm of 49.2, 45.7, 41.4, 12.6 and 10.8 ppm±0.1 ppm, respectively;
  a solid state $^{13}$C NMR spectrum substantially as depicted in any one of FIGS. 24-26;
  a solid state $^{13}$C NMR spectrum with peaks at 174.3, 170.8, 166.5, 137.7, and 135.9 ppm and also at 138.6, 74.1, 72.1 and 71.4 ppm±0.2 ppm;
  a solid state $^{13}$C NMR spectrum having chemical shift differences between said characteristic peaks at 138.6, 74.1, 72.1 and 71.4 ppm±0.2 ppm and a reference peak at 125.1±0.2 ppm of 13.5, −51.0, −53.1 and −53.7 ppm±0.1 ppm, respectively;
  a DSC thermogram substantially as depicted in FIG. 7; a DSC melting peak at about 163° C.±4° C., or 163.3° C. and a DSC melting onset at about 153° C.±4° C., or 153.0° C.;
  a TGA thermogram substantially as depicted in FIG. 8; a residual MTBE content of 9.7%±2%, preferably about 9.7%, w/w as determined by GC; and combinations thereof.

17. The crystalline cabazitaxel form IV n-butanol solvate of claim 14, further characterized by:
  an X-ray powder diffraction pattern having peaks at 7.4, 7.9, 8.8, 12.9 and 13.5 degrees two theta±0.1 degrees two theta and optionally having no peak in the area from 10.4 to 12.2 degrees two theta, and also having an additional one, two, three, four or five peaks selected from 10.2, 12.6, 19.0, 19.7 and 26.6 degrees 2-theta±0.1 degrees 2-theta; a powder X-ray diffraction pattern substantially as depicted in FIG. 12;
  a solid state $^{13}$C NMR spectrum with peaks at 128.4, 60.6, 19.0 and 13.6 ppm±0.2 ppm;
  a solid state $^{13}$C NMR spectrum having chemical shift differences between said characteristic peaks at 128.4, 60.6, 19.0 and 13.6 ppm±0.2 ppm and a reference peak at 125.2±0.2 ppm of 3.2, −64.7, −106.2 and −111.6 ppm±0.1 ppm, respectively;

a solid state $^{13}$C NMR spectrum substantially as depicted in any one of FIGS. 30-32;
a solid state $^{13}$C NMR spectrum with peaks at 128.4, 60.6, 19.0 and 13.6 ppm±0.2 ppm and also at 173.3, 139.5, 133.9 and 74.5 ppm±0.2 ppm;
a solid state $^{13}$C NMR spectrum having chemical shift differences between said characteristic peaks at 173.3, 139.5, 133.9 and 74.5 ppm±0.2 ppm and a reference peak at 125.2±0.2 ppm of 48.1, 14.3, 8.7 and −50.7 ppm±0.1 ppm, respectively;
a DSC thermogram substantially as depicted in FIG. 13; a DSC melting peak at about 168° C.±4° C., or 167.9° C. and a DSC melting onset at about 160° C.±4° C., or 159.8° C.;
a TGA thermogram substantially as depicted in FIG. 14; a residual n-butanol content of 8.3%±2.0% w/w, preferably about 8.3% w/w as determined by GC; and combinations thereof.

18. The crystalline cabazitaxel form V 1-propanol solvate of claim 14, further characterized by:
an X-ray powder diffraction pattern having peaks at 7.8, 9.0, 10.2, 15.1 and 15.3 degrees two theta±0.1 degrees two theta and optionally having no peak in the area from 10.5 to 12.1 degrees two theta, and also having additional one, two, three, four or five peaks selected from 7.4, 12.9, 13.3, 13.6 and 18.2 degrees 2-theta±0.1 degrees 2-theta;
a powder X-ray diffraction pattern substantially as depicted in FIG. 15;
a solid state $^{13}$C NMR spectrum with peaks at 173.7, 166.2, 79.5 and 73.6 ppm±0.2 ppm;
a solid state $^{13}$C NMR spectrum having chemical shift differences between said characteristic peaks at 173.7, 166.2, 79.5 and 73.6 ppm±0.2 ppm and a reference peak at 125.1±0.2 ppm of 48.6, 41.1, −45.6 and −51.5 ppm±0.1 ppm, respectively;
a solid state $^{13}$C NMR spectrum with peaks at 135.5, 70.4, 25.7 and 10.6 ppm±0.2 ppm and also at 173.7, 166.2, 79.5 and 73.6 ppm±0.2 ppm;
a solid state $^{13}$C NMR spectrum having chemical shift differences between said characteristic peaks at 173.7, 166.2, 79.5 and 73.6 ppm±0.2 ppm and a reference peak at 125.1±0.2 ppm of 48.6, 41.1, −45.6 and −51.5 ppm±0.1 ppm, respectively;
a DSC thermogram substantially as depicted in FIG. 16; DSC melting peak at about 167° C.±4° C., or 166.6° C. and DSC melting onset at about 156° C.±4° C., or 156.0° C.;
a TGA thermogram substantially as depicted in FIG. 17; a residual 1-propanol content of 6.4%±1.5% w/w, preferably about 6.4%, w/was determined by GC; and combinations thereof.

19. A solid pharmaceutical composition comprising one or more crystals of the crystalline cabazitaxel according to claim 1, and at least one pharmaceutically acceptable excipient.

20. A solid pharmaceutical composition comprising one or more crystals of the crystalline cabazitaxel according to claim 14, and at least one pharmaceutically acceptable excipient.

21. A process for preparing a pharmaceutical composition comprising one or more crystalline or amorphous cabazitaxel that is:
crystalline cabazitaxel designated as form III, characterized by:
a solid state $^{13}$C NMR spectrum with peaks at 139.8 127.8, 63.4, 25.4 and 23.5 ppm±0.2 ppm;
a solid state $^{13}$C NMR spectrum having chemical shift differences between said characteristic peaks at 139.8 127.8, 63.4, 25.4 and 23.5 ppm±0.2 ppm and a reference peak at 125.1±0.2 ppm of 14.8, 2.8, −61.7, −99.6 and −101.6 ppm±0.1 ppm, respectively;
a solid state $^{13}$C NMR spectrum substantially as depicted in any one of FIGS. 27-29; and combinations thereof;
crystalline cabazitaxel designated as form II, characterized by:
a solid state $^{13}$C NMR spectrum with peaks at 174.3, 170.8, 166.5, 137.7, and 135.9 ppm±0.2 ppm;
a solid state $^{13}$C NMR spectrum having chemical shift differences between said characteristic peaks at 174.3, 170.8, 166.5, 137.7, and 135.9 ppm±0.2 ppm and a reference peak at 125.1±0.2 ppm of 49.2, 45.7, 41.4, 12.6 and 10.8 ppm±0.1 ppm, respectively;
a solid state $^{13}$C NMR spectrum substantially as depicted in any one of FIGS. 24-26; and combinations thereof;
crystalline cabazitaxel form IV, characterized by:
a solid state $^{13}$C NMR spectrum with peaks at 128.4, 60.6, 19.0 and 13.6 ppm±0.2 ppm;
a solid state $^{13}$C NMR spectrum having chemical shift differences between said characteristic peaks at 128.4, 60.6, 19.0 and 13.6 ppm±0.2 ppm and a reference peak at 125.2±0.2 ppm of 3.2, −64.7, −106.2 and −111.6 ppm±0.1 ppm, respectively;
a solid state $^{13}$C NMR spectrum substantially as depicted in any one of FIGS. 30-32; and combinations thereof; or
crystalline cabazitaxel form V, characterized by:
a solid state $^{13}$C NMR spectrum with peaks at 135.5, 70.4, 25.7 and 10.6 ppm±0.2 ppm;
a solid state $^{13}$C NMR spectrum having chemical shift differences between said characteristic peaks at 135.5, 70.4, 25.7 and 10.6 ppm±0.2 ppm and a reference peak at 125.1±0.2 ppm of 10.4, −54.7, −99.4 and −114.5 ppm±0.1 ppm, respectively;
a solid state $^{13}$C NMR pattern substantially as depicted in any one of FIGS. 33-35; and combinations thereof;
crystalline cabazitaxel form III 2-propanol solvate, characterized by:
a powder X-ray diffraction pattern having peaks at 7.4, 9.0, 10.3, 13.3 and 13.6 degrees two theta±0.1 degrees two theta and optionally having no peak in the area from 10.5 to 12.1 degrees two theta;
crystalline cabazitaxel form II MTBE solvate, characterized by:
a powder X-ray diffraction pattern having peaks at 7.4, 7.7, 8.9, 12.1 and 13.2 degrees two theta±0.1 degrees two theta and optionally having no peak in the area from 10.4 to 11.9 degrees two theta;
crystalline cabazitaxel form IV n-butanol solvate, characterized by:
a powder X-ray diffraction pattern having peaks at 7.4, 7.9, 8.8, 12.9 and 13.5 degrees two theta±0.1 degrees two theta and optionally having no peak in the area from 10.4 to 12.2 degrees two theta;
crystalline cabazitaxel form V 1-propanol solvate characterized by:
a powder X-ray diffraction pattern having peaks at 7.8, 9.0, 10.2, 15.1 and 15.3 degrees two theta±0.1 degrees two theta and optionally having no peak in the area from 10.5 to 12.1 degrees two theta; or
the process comprising combining the one or more crystalline cabazitaxel with at least one pharmaceutically acceptable excipient.

22. A method of treating a person suffering from prostate cancer, comprising administering a therapeutically effective amount of a pharmaceutical composition according to claim 19.

23. A method of treating a person suffering from prostate cancer, comprising administering a therapeutically effective amount of a pharmaceutical composition according to claim 20.

24. A process for preparing a solution comprising cabazitaxel comprising combining the crystalline cabazitaxel of claim 1 or claim 14 with a solvent.

25. The process of claim 24, wherein the solvent is water, an organic solvent, or a combination thereof.

26. A solution prepared according to the process of claim 24.

* * * * *